US008008431B2

(12) United States Patent
Weinschenk et al.

(10) Patent No.: US 8,008,431 B2
(45) Date of Patent: Aug. 30, 2011

(54) TUMOR-ASSOCIATED PEPTIDES THAT BIND TO MHC-MOLECULES

(75) Inventors: Toni Weinschenk, Aichwald (DE); Claudia Lemmel, Tübingen (DE); Hans-Georg Rammensee, Tübingen-Unterjesingen (DE); Stefan Stevanovic, Tübingen (DE)

(73) Assignee: Immatics Biotechnologies GmbH, Tuebingen (DE)

( * ) Notice: Subject to any disclaimer, the term of this patent is extended or adjusted under 35 U.S.C. 154(b) by 611 days.

(21) Appl. No.: 11/596,802

(22) PCT Filed: May 24, 2005

(86) PCT No.: PCT/EP2005/005619
§ 371 (c)(1),
(2), (4) Date: Nov. 3, 2008

(87) PCT Pub. No.: WO2005/116051
PCT Pub. Date: Dec. 8, 2005

(65) Prior Publication Data
US 2010/0029573 A1  Feb. 4, 2010

(30) Foreign Application Priority Data

May 25, 2004  (DE) .......................... 10 2004 026 135

(51) Int. Cl.
*C07K 5/00* (2006.01)
*G01N 33/06* (2006.01)
*C12P 21/06* (2006.01)
(52) U.S. Cl. ........................ 530/300; 436/23.1; 435/69.1
(58) Field of Classification Search .................. None
See application file for complete search history.

(56) References Cited

U.S. PATENT DOCUMENTS

| 5,831,016 A * | 11/1998 | Wang et al. .................. 530/350 |
| 5,955,314 A * | 9/1999 | Hillman et al. .............. 435/69.5 |
| 6,410,240 B1 | 6/2002 | Hodge et al. |
| 2002/0061543 A1 | 5/2002 | Ross |
| 2003/0113733 A1 | 6/2003 | Khan et al. |
| 2005/0063967 A1 | 3/2005 | Young |

FOREIGN PATENT DOCUMENTS

| DE | 102 25 144 A1 | 12/2003 |
| DE | 10225144 | 12/2003 |
| WO | WO2002057420 | * 7/2002 |
| WO | WO 2004015390 | * 2/2004 |
| WO | WO2004031210 | * 4/2004 |

OTHER PUBLICATIONS

Sequence search result , 2010.*
Harig et al, Blood, vol. 98, p. 2999-3005, 2001.*
Sequence search result (Sette) 2010.*
Sequence search result (Moore) 2010.*
Sequence search result (Hillman) 2010.*
Krüge et al Cancer Immunol Immunother vol. 54:826-836, online published Dec. 2004 (R5, IDS filed Jul. 12, 2007).*
Dejgaard, K. et al., "Identification, Molecular Cloning, Expression and Chromosome Mapping of a Family of Transformation Upregulated hnRNP-K Proteins Derived by Alternative Splicing," *J. Mol. Biol.*, 1994, vol. 236, No. 1, pp. 33-48, XP-002963154.
Flad, T. et al., "Direct Identification of Major Histocompatibility Complex Class I-bound Tumor-associated Peptide Antigens of a Renal Carcinoma Cell Line by a Novel Mass Spectrometric Method," *Cancer Research*, Dec. 15, 1998, vol. 58, No. 24, pp. 5803-5811, XP-001161018.
Furuya, M. et al., "Expression of regulator of G protein signalling protein 5 (RGS5) in the tumour vasculature of human renal cell carcinoma," *Journal of Pathology*, Feb. 18, 2004, vol. 203, No. 1, pp. 551-558.
Hofmann, S. et al., "Rapid and sensitive identification of major histocompatibility complex class I-associated tumor peptides by nanoLC MALDI MS/MS," *MCP In Press*, Aug. 19, 2005, XP-002344047.
Krüger, T. et al., "Lessons to be learned from primary renal cell carcinomas: novel tumor antigens and HLA ligands for immunotherapy," *Cancer Immunol. Immunother.*, Sep. 2005, vol. 54, No. 9, pp. 826-836, XP-002344048.
Lemmel, C. "Dissertation: Qualitative und quantitative Analyse krankheitsassoziierter MHC-Klasse-I-Liganden durch massenspektrometrische Verfahren," <http://w210.ub.uni-tuebingen.de/dbt/volltexte/2004/1287/pdf/Lemmel_Dissertation.pdf>, Jun. 24, 2004, XP002344158.
Melief, C. et al., "Peptide-based cancer vaccines," *Current Opinion in Immunology*, 1996, vol. 8, No. 5, pp. 651-657, XP-002344045.
Purcell, A.W. et al., "Immunoproteomics: Mass Spectrometry-Based Methods to Study the Targets of the Immune Response," *Molecular & Cellular Proteomics*, Mar. 2004, vol. 3, No. 3, pp. 193-208, XP-002344046.
Schirle, M. et al., "Identification of tumor-associated MHC class I ligands by a novel T cell-independent approach," *Eur. J. Immunol.*, Aug. 2000, vol. 30, No. 8, pp. 2216-2225, XP-002246625. A.W. Purcell et al.: Immunoproteomics "Mass Spectrometry-Based Methods to Study the Targets of the Immune Response", Molecular & Cellular Proteomics 3.3 2004, pp. 193-208 The American Society and Biochemistry and Molecular Biology. Inc. XP-002344046.
Claudia Lemmel et el. "Differential Quantitative Analysis of MHC Ligands by Mass Spectrometry Using Stable Isotope Labeling". Nature Biotechnology, Nature Publising Group, New York, NY, US, BD.22 NR. 4, Apr. 1, 2004, 450-454, XP002359085, ISSN 1087-0156.
G. Pluschke et al: "Molecular Cloning of a 3, 15 Human Melanoma-Associated Chondroitin Sulfate Proteoglycan" Proceedings of the National Academy of Sciences of USA, National Academy of Science, Washington, DC, US, BD. 93, NR. 18, Sep. 1, 1996, 9710-9715, XP003019023, ISSN: 0027-8424.

(Continued)

*Primary Examiner* — Misook Yu
*Assistant Examiner* — Lei Yao
(74) *Attorney, Agent, or Firm* — Baker, Donelson, Bearman, Caldwell & Berkowitz, PC

(57) ABSTRACT

The invention relates to a tumor-associated peptide with an amino acid sequence selected from the group consisting of SEQ ID NO. 1 to SEQ ID NO. 577 from the attached sequence protocol, the peptide being capable of binding to a molecule of the human major histocompatibilityg complex (MHC) class I. The invention further relates to the use of the peptides for preparation of a drug and for the treatment of tumor diseases and/or adenomatous diseases. Furthermore, a pharmaceutical composition is described comprising at least one of the peptides.

19 Claims, 5 Drawing Sheets

OTHER PUBLICATIONS

Database Geneseq [Online], "Human Brain Expressed Single Exon Probe Encoded Protein Seq Id No: 25597." Nov. 5, 2001, XP002521875, EBI Accession No. GSP:AAM53492, Database Accession No. AAM53492.

Database Geneseq [Online], "Propionibacterium Acnes Immunogenic Protein # 19260" XP002521879, Feb. 27, 2002. EBI Accession No. GSP:AAU58364, Database Accession No. AAU58364.

T. Flad et al: "Direct Identification of Major Histocompatibility Complex Class I-Bound Tumor-Associated Peptide Antigens of a Renal Carcinoma Cell Line by a Novel Mass Spectrometic Method", Cancer Research, American Association for Cancer Research, Baltimore, MD, US, BD. 58, NR. 24, Dec. 15, 1998.

Tobias Krueger et al.: "Lessons to Be Learned From Primary Renal Cell Carcinomas: Novel Tumor Antigens and HLA Ligands for Immunotherapy." Cancer Immunology. Immunotherapy CII. Sep. 2005, BD. 54, NR. 9, 826-836, XP002344048 ISSN: 0340-7004.

Stefan Stevanovic et al.: "Generating Data 1-17 for Databases—The Peptide Repertoire of HLA Molecules". Novartis Foundation Symposium, Wiley, Chester, GB, BD 254, Jan. 1, 2003, 143-252: XP009105681; ISSN: 1528-2511.

Markus Shirle et al. "Identification of 1-17 Tumor-Associated MHC Class I Ligands by a Novel T Cell-Independent Approach" European Journal O Fimmunology. Weinheim DE. BD/3 NR Aug. 8, 2008, 2216-2225, XXP002246625, ISSN: 0014-2980.

Cornelis J.M. Melief. et al.: "Peptide-Based Cancer Vaccines" Current Opinion in Immunology BD. 8, NR. 5, 1996, 651-657, XP002344045, ISSN: 0952-7915.

Search Report for EP 09000315 Dated Mar. 31, 2009.

Rammensee et al., "SYFPEITHI: database for MHC ligands and peptide motifs, Immunogenetics", Nov. 1999, pp. 213-219, Springer-Verlag.

* cited by examiner

US 8,008,431 B2

TUMOR-ASSOCIATED PEPTIDES THAT BIND TO MHC-MOLECULES

CROSS-REFERENCE TO A RELATED APPLICATION

This application is a National Stage Application of International Application Number PCT/EP2005/005619, filed May 24, 2005; which claims priority to German Application No. 10 2004 026 135.0, filed May 25, 2004.

The present invention relates to tumor-associated peptides that are capable of binding to a molecule of the human class I major histocompatibility complex (MHC). Such peptides are, for example, used in the immunotherapy of tumor diseases.

The recognition of tumor-associated antigens (TAA) by immune system components plays a major role in the elimination of tumor cells by the immune system. This mechanism is based on the prerequisite that there are qualitative or quantitative differences between tumor cells and normal cells. In order to achieve an anti-tumor response, the tumor cells have to express antigens that are targets of an immune response sufficient for elimination of the tumor.

Particularly CD8-expressing cytotoxic T lymphocytes (in the following termed CTL) participate in tumor rejection. In order to elicit such an immune reaction by cytotoxic T cells, foreign proteins/peptides must be presented to the T cells. T cells recognize antigens as peptide fragments only if those are presented on cell surfaces by MHC molecules. These MHC ("major histocompatibility complex") molecules are peptide receptors that normally bind peptides within the cell in order to transport them to the cell surface. This peptide/MHC molecule complex can be recognized by T cells. Human MHC molecules are termed human leukocyte antigens (HLA).

There are two classes of MHC molecules: MHC class I molecules, present on most nucleated cells, present peptides that are generated by proteolytic degradation of endogenous proteins. MHC class II molecules are only found on professional antigen presenting cells (APC), and present peptides of exogenous proteins that are engulfed and processed by APC during endocytosis. Complexes formed between peptide and MHC class I are recognized by CD8-positive cytotoxic T cells, complexes formed between peptide and MHC class II are recognized by CD4 T helper cells.

In order for a peptide to elicit a cellular immune response, it needs to bind to an MHC molecule. This process depends on the allele of the MHC molecule and on the amino acid sequence of the peptide. Usually, MHC class I-binding peptides have a length of 8-10 residues, and their sequences contain two conserved residues ("anchors") interacting with the corresponding binding groove of the MHC molecule.

In order for the immune system to be able to elicit an effective CTL response against tumor-derived peptides, such peptides not only have to be able to bind to certain MHC class I molecules being expressed by tumor cells, they also have to be recognized by T cells bearing specific T cell receptors (TCR).

The main purpose for developing a tumor vaccine is the identification and characterization of tumor-associated antigens being recognized by CD8+ CTL.

The antigens, or their epitopes, that are recognized by the tumor-specific cytotoxic T lymphocytes can be molecules from all protein classes, such as enzymes, receptors, transcription factors, etc. Another important class of tumor-associated antigens are tissue-specific structures such as CT ("cancer testis") antigens that are expressed in various types of tumors and in healthy testicular tissue. For the proteins to be recognized as tumor-specific antigens by cytotoxic T lymphocytes, and to be therefore used in a therapy, certain conditions must be met: The antigen should mainly be expressed by tumor cells and not or only in smaller amounts by normal cells in contrast to tumors. Furthermore, it is desirable that the respective antigen is present in high concentration not only in one type of tumor but in other tumor types as well. The presence of epitopes in the amino acid sequence of the antigen is also absolutely mandatory since such peptides that are derived from a tumor-associated antigen ("immunogenic peptides"), should lead to a T cell response, either in vitro or in vivo.

Therefore, TAAs are a starting point for the development of a tumor vaccine. The methods for identifying and characterizing the TAAs are based on the use of CTL that have already been induced in the patients, or they are based on the generation of differential transcription profiles between tumors and normal tissues.

However, the identification of genes overexpressed in tumor tissues or human tumor cell lines, or selectively expressed in such tissues or cell lines, does not provide precise information as to the use of the antigens being transcribed from these genes in the immune therapy. This is because only individual epitopes of these antigens are suitable for such an application since only the antigen epitopes—not the entire antigen—elicit a T cell response through MHC presentation. It is therefore important to select only those peptides from overexpressed or selectively expressed proteins that are presented in connection with MHC molecules, so targets for the specific recognition of primary cells or of tumor cell lines established from primary tumor tissue cells, by cytotoxic T lymphocytes could be obtained.

Based on this background, it is an objective of the present invention to provide at least one novel amino acid sequence for such a peptide that is capable to bind to a molecule of the human major histocompatibility complex (MHC) class I.

According to the invention this objective is addressed by providing a tumor-associated peptide with an amino acid sequence selected from the group consisting of SEQ ID NO. 1 to SEQ ID NO. 577 in the attached sequence protocol, whereby the peptide being capable of binding to a molecule of the human major histocompatibility complex (MHC) class I. In this way, the objective forming the basis of the invention is addressed completely.

It is to be understood that the identified tumor peptides may be synthesized to obtain larger quantities or for the use for the below described purposes, or may be expressed in cells.

The inventors were able to isolate and identify the above mentioned peptides from tumor tissue as specific ligands from MHC class I molecules. The term "tumor-associated" peptides herein refers to peptides that are isolated and identified from tumor material. Thus, these peptides that are presented on true (primary) tumors are subjected to antigen processing in a tumor cell.

The specific ligands could be used in cancer therapy, e.g. to induce an immune response against tumor cells expressing the respective antigens from which the peptides are derived.

Such an immune response in form of an induction of CTL may be obtained in vivo. In order to obtain such an immune response the peptide is administered to a patient suffering from a TAA-associated tumor disease, for example in form of a pharmaceutical composition.

On the other hand, a CTL response against a tumor expressing the antigens from which the peptides are derived may also be elicited ex vivo. In order to do so, the CTL precursor cells are incubated together with antigen presenting cells and the peptides. Then, the thus stimulated CTL are cultivated, and these activated CTL are administered to the patient.

Furthermore, it is possible to load APC with the peptides ex vivo, and to administer these loaded APC to the patient expressing in the tumor tissue the antigens from which the peptide is derived. Then, the APC themselves may present the peptide to the CTL in vivo, and thereby activate them.

However, the peptides according to the invention may also be used as diagnostic reagents.

Thus, using the peptides it could be found out if CTL are present in a CTL population or have been induced by a therapy that are specifically directed against a peptide, The peptides may also be used to test for the increase of precursor T cells with reactivity against the defined peptide.

Furthermore, the peptide may be used as a marker to track the disease course of a tumor expressing the antigen from which the peptide is derived.

The attached Table 1 lists the identified peptides. The table also contains the proteins from which the peptides are derived, and the respective positions of the peptides in the respective proteins which are named or abbreviated by accepted gene symbols according to the "HUGO Gene Nomenclature Committee" The English names of the proteins have been maintained to avoid erroneous translations. Furthermore, the ACC numbers are listed that are used in the gene bank of the "National Center for Biotechnology Information" of the National Institute of Health.

The inventors were able to isolate the peptides (or ligands) from 8 renal cell tumors and 2 glioblastomas from altogether 10 patients, RCC75, RCC98, RCC100, RCC103, RCC112, RCC115, RCC116, RCC130 and NCH359, as well as NCH361, and from a tumor cell line (J-Y).

From the patients' tumors and the cell line J-Y 577 ligands could be identified that were bound to the HLA subtypes A*03, B*07, B*40 (RCC75), A*01, A*03, B*07, B*18 (RCC98), A*02, A*03, B*07, B*18 (RCC100), A*11, A*25, B*15, B*44 (RCC103), A*01, A*31, B*08, B*27 (RCC112), A*02, A*03, B*15, B*18 (RCC115), A*01, A*02, B*27, B*37 (RCC116), A*02, A*24, B*07, B*44 (RCC130), A*03, A*32, B*07, B*35 (NCH359), A*26, B*38 (NCH361) and A*02, B*07 (J-Y).

Some of the ligands are derived from highly expressed so called "housekeeping" genes that are uniformly expressed in most tissues, however, many are characterized by tissue-specific and tumor-specific expression.

Thus, several peptides could be identified that are derived from proteins which are especially overexpressed in tumor tissue. For example, fragments of tenascin-C (GLAPSIRTK, SEQ ID NO. 2) could be identified (Herold-Mende et al., Clinical impact and Functional Aspects of Tenascin-C Expression during Glioma Progression, 2002, Int. J. Cancer, 98: 362-369).

Also, the inventors were able to identify ligands, among others, that are derived from SOX9 (YPHLHNAEL, SEQ ID NO. 7) and RGS5 (LAALPHSCL, SEQ ID NO. 448).

As primary tumor cells are not suited for in vitro culture, the inventors have chosen a human tumor cell line as an example in order to additionally demonstrate that peptides according to the invention identified from this cell line, are suited to activate cytotoxic T lymphocytes in vitro. Particularly, the inventors could show that using a peptide from the established tumor cell line JY as an example, it was possible to generate cytotoxic T lymphocytes (CTL) in vitro that are specific for the selected peptide with the sequence FPSL-REAAL (MAGEA1, position 294-302) and SEQ ID NO. 114 and the HLA allele B*0702. Using these CTL, KM22 target cells loaded with the SEQ ID NO. 114 peptide could be selectively killed, whereas KM22 control target cells not loaded with the SEQ ID NO. 114 peptide were not recognized by the cytotoxic T cells. Thus, it could be shown exemplified that human T cells could be activated in vitro using the peptides according to the invention as epitopes. Furthermore, it could be demonstrated that the cytotoxic T lymphocytes lysing the T2 cells loaded with the SEQ ID NO. 114 peptide also express interferon gamma which has been described as a reliable marker for the activation of T cells.

In a preferred embodiment, it is also possible to use peptides for stimulating an immune response that comprise sequence ID NO. 1 to 577, and in which at least one amino acid has been replaced by another amino acid with similar chemical properties.

Referring to the corresponding MHC subtypes, these are, for example, the anchor amino acids that may be replaced by amino acids with similar chemical properties. Thus, for example, in peptides associated with the MHC subtype HLA-A*2, leucine on position 2 may be replaced by isoleucine, valine or methionine and vice versa, and at the C-terminus leucine by valine, isoleucine and alanine, each containing non-polar side chains.

Furthermore it is possible to use peptides with sequence ID No. 1 to 577 comprising at least one additional amino acid N- or/and C-terminally, or in which at least one amino acid is deleted.

Furthermore, peptides with sequence ID No. 1 to 577 may be used in which at least one amino acid is chemically modified.

The varying amino acid(s) is (are) selected in such way that the variation does not affect the immunogenicity of the peptide, i.e. demonstrates a similar binding affinity to the MHC molecule and the capability for T cell stimulation.

According to the invention, the peptide may be used for treatment of tumor diseases and/or adenomatous diseases.

The tumor diseases to be treated comprise, for example, kidney, brain, mammary, pancreas, gastric, testicular and/or skin cancers and tumor diseases of the nerve system. This list of tumor diseases is only exemplary, and is not intended to limit the area of application. The inventors were able to show in independent studies that the peptides according to the invention are suitable for such use. In these studies it was shown that specifically generated CTL that are specific for certain peptides were able to kill tumor cells effectively and selectively.

Basically, for the use of tumor-associated antigens in a tumor vaccine, several application forms are possible. For example, Tighe et al. 1998, Gene vaccination: plasmid DNA is more than just a blueprint, Immunol. Today 19(2):89-97, described that the antigen may be administered either as recombinant protein together with suitable adjuvants or carrier systems, or in form of the cDNA encoding the antigen in plasmid vectors. For this, the antigen needs to be processed and presented by antigen presenting cells (APC) in the patient's body in order for an immune response to be induced.

Melief et al., 1996, Peptide-based cancer vaccines, Curr. Opin. Immunol. 8:651-657, demonstrated another option, namely the use of synthetic peptides as a vaccine.

For this purpose, the peptide may be used in a preferred embodiment together with added adjuvants, or alone.

As an adjuvant, for example, the granulocyte macrophage colony stimulating factor (GMCSF) may be used. Further examples for such adjuvants are aluminum hydroxide, mineral oil emulsions such as, for example, Freund's adjuvant, saponins or silicon compounds.

The use of adjuvants provides the advantage that the immune response induced by the peptide may be enhanced, and/or the peptide may be stabilized.

In another preferred embodiment, the peptide is used bound onto an antigen presenting cell. This measure provides the advantage that the peptides can be presented to the immune system, particularly cytotoxic T lymphocytes (CTL). By this, the CTL are able to recognize the tumor cells and specifically kill them. Suitable as antigen presenting cells for such an application are, for example, dendritic cells, monocytes or B lymphocytes.

For this purpose, the cells are, for example, loaded with peptides ex vivo. On the other hand, it is also possible to transfect the cells with DNA encoding the peptides or with the corresponding RNA to express the peptide on the cells.

The inventors were able to show in independent studies that it is possible to load dendritic cells (DC) with specific peptides, and that these loaded dendritic cells activate peptide-specific CTL. This means that the immune system can be stimulated to raise CTL against the tumors expressing the respective peptides.

The antigen presenting cells carrying the peptide may be used either directly or may be activated prior to their use, for example with the heat shock protein gp96. This heat shock protein induces the expression of MHC class I molecules and co-stimulatory molecules such as B7, and also stimulates the production of cytokines. Together, this supports the induction of immune responses.

In another preferred embodiment, the peptides are used to label leukocytes, especially T lymphocytes.

This application is advantageous if it is intended to use the peptides to find out if CTL are present in a CTL population that are specifically directed against a peptide.

Furthermore, the peptide may be used as a marker to evaluate the progress of a therapy for a tumor disease.

The peptide may be used in other immunizations or therapies for monitoring the therapy as well. Therefore, the peptide may not only be used therapeutically but also diagnostically.

In another embodiment, the peptides are used to generate an antibody.

Polyclonal antibodies may be obtained conventionally by immunizing animals by injection of the peptides and subsequent purification of the immunoglobulin.

Monoclonal antibodies may be generated according to standard protocols, such as, for example, described in Methods Enzymol. (1986), 121, Hybridoma technology and monoclonal antibodies.

In another aspect the invention also relates to a pharmaceutical composition comprising one or more of the peptides.

This composition is used, for example, for parenteral administration, such as subcutaneous, intradermal or intramuscular, or for oral application. For this, the peptides are solved or suspended in a pharmaceutically acceptable, preferably aqueous carrier. Furthermore, the composition may contain excipients such as buffers, binders, diluents, etc.

The peptides may also be given together with immunostimulatory substances such as cytokines. A comprehensive description of excipients that may be used in such compositions is given, for example in A. Kibbe, Handbook of Pharmaceutical Excipients, 3. Ed., 2000, American Pharmaceutical Association and pharmaceutical press.

The preparation may be used for prevention, prophylaxis and/or therapy of tumor diseases and/or adenomatous diseases.

The pharmaceutical preparation containing at least one of the peptides with sequence ID NO. 1 to 577 will be administered to a patient suffering from a tumor disease with which the respective peptide or antigen is associated. Thus, a tumor-specific immune response based on tumor-specific CTL can be elicited.

The amount of the peptide or peptides in the pharmaceutical composition is present in a therapeutically effective amount.

The peptides that are present in the composition may also bind to at least two different HLA types.

In a further aspect, the present invention relates to nucleic acid molecules encoding the peptides with sequence ID NO. 1 to 577.

The nucleic acid molecules may be DNA or RNA molecules, and may also be used for immune therapy of cancer diseases. The peptide which is expressed from the nucleic acid molecule induces an immune response against tumor cells expressing the peptide.

According to the invention, the nucleic acid molecules may also be present in a vector.

Furthermore, the invention relates to cells which have been genetically altered using a nucleic acid molecule encoding the peptides so that they produce a peptide with the sequence ID NO. 1 to 577.

For this purpose, the cells are transfected with the DNA encoding the peptides, or with the respective RNA, whereby the peptides are made to be expressed on the cells. As antigen presenting cells for such an approach are suited, for example, dendritic cells, monocytes or B lymphocytes.

It is to be understood that the features that have been mentioned above and that are yet to be discussed below, are suitable not only in the respectively described combination but also alone, without leaving the scope of the present invention.

Embodiments of the invention are presented and discussed in the following examples and in the attached figures.

Figure 5:
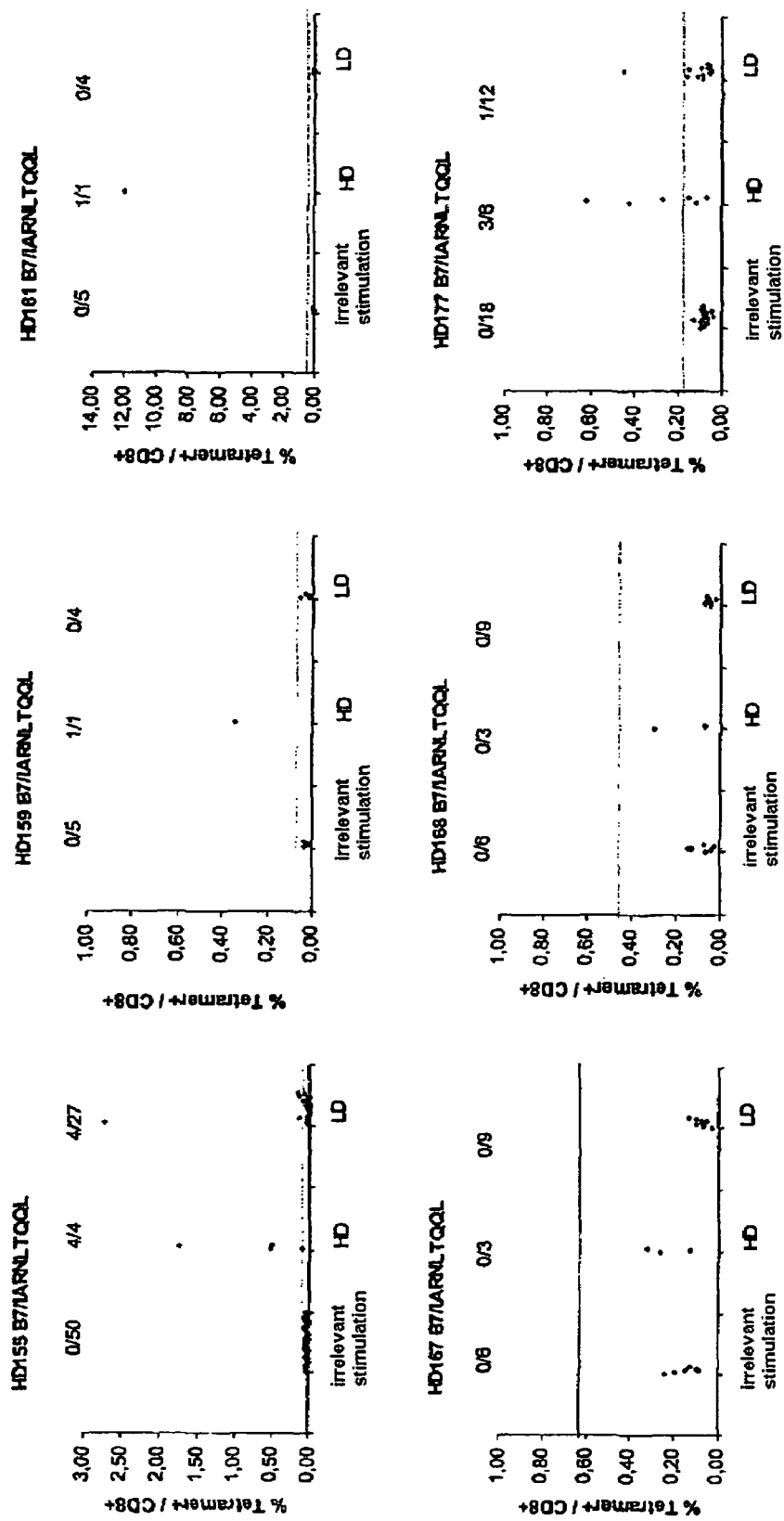

FIG. 5 shows the tetramer analysis of microsphere-driven proliferation of B*0702/IARNLTQQL-specific CD8+ lymphocytes from peripheral blood. Four (4) out of 6 tested donors (HD155, 159, 161, 177) had significant T cell responses (above the red line) that were directed specifically against the tested peptide antigen with SEQ ID NO. 233, as could be shown by detection of peptide/HLA-B*0702 complex-specific T cell receptors by tetramer staining.

EXAMPLE 1

1.1 Patient Samples

Eight samples were obtained from the Department of Urology at the University of Tübingen, Tübingen, Germany, that were derived from patients with histologically confirmed renal cell carcinoma. The patient termed RCC75 had the following HLA haplotype: A*03, B*07, B*40. The patient termed RCC98 had the following HLA haplotype: A*01, A*03, B*07, B*18, The patient termed RCC100 had the following HLA haplotype: A*02, A*03 B*07, B*18. The patient termed RCC103 had the following HLA haplotype: A*11, A*25, B*15, B*44. The patient termed RCC112 had the following HLA haplotype: A*01, A*31, B*08, B*27. The patient termed RCC115 had following the HLA haplotype: A*02, A*03, B*15, B*18, The patient termed RCC116 had the following HLA haplotype: A*01, A*02, B*27, B*37, and the patient termed RCC130 had following HLA haplotype: A*02, A*24, B*07, B*44.

Two samples were obtained from the Department of Neurosurgery, University of Heidelberg, Heidelberg, Germany, that were derived from patients with histologically confirmed glioblastomas. The patient termed NCH359 had the following HLA haplotype: A*03, A*32, B*07, B*35. The patient termed NCH361 had following HLA haplotype: A*26 and B*38.

1.2. Isolation of MHC Class I-Bound Peptides

Shock frozen tumor samples were processed as previously described in Schirle, M. et al., Identification of tumor-associated MHC class I ligands by a novel T cell-independent approach, 2000, European Journal of Immunology, 30:2216-2225. The peptides were isolated according to standard protocols, using the monoclonal antibody W6/32 which is specific for HLA class 1 molecules, or using the monoclonal antibody BB7.2 which is specific for HLA-A2. Barnstable, C. J. et al., Production of monoclonal antibodies to group A erythrocytes, HLA and other human cell surface antigens-new tools for genetic analysis, 1978, Cell, 14:9-20, and Parham, P. & Brodsky, F. M., Partial purification and some properties of BB7.2. A cytotoxic monoclonal antibody with specificity for HLA-A2 and a variant of HLA-A28, 1981, Hum. Immunol., 3:277-299, have described generation and use of these antibodies.

1.3. Mass Spectroscopy

The peptides were separated by "reversed phase HPLC" (SMART system, μRPC C2/C18 SC 2.1/19, Amersham Pharmacia Biotech), and the obtained fractions were analyzed by nanoESI MS. The approach corresponded to the approach described by Schirle, M. et al., Identification of tumor-associated MHC class I ligands by a novel T cell-independent approach, 2000, European Journal of Immunology, 30:2216-2225.

The peptides obtained from tumor tissue were identified by capillary LC MS, as just described, however with minor modifications: 100 μL of each sample were loaded, desalted and pre-concentrated on a 300 μm*5 mm C18μ guard column (LC Packings). Solvent and sample were added using a syringe pump (PHD 2000, Harvard Apparatur, Inc.) with a sealed 100 μL syringe (1710 RNR, Hamilton) at a speed of 2 μL/min. For separation of the peptides, the pre-concentration column was installed before a 75 μm*250 mm C18 column (LC Packings). Then, a binary gradient with 25-60% B was run for 70 min. during which time the flow rate was reduced from 12 μL/min to approximately 300 nL/min. using a TEE connector (ZTIC, Valco) and a 300 μm*150 mm C18 column.

To ensure that the system was free from peptide residues, a blank was measured respectively. Online-fragmentation was performed as described, and the spectra of the fragments were analyzed manually. Data base searches (NCBInr, EST) were performed using MASCOT (http://www.matrixscience.com).

1.4. Identification of the MHC Class I Ligands

In the attached sequence protocol and in the attached table 1 the ligands are listed that were bound to the HLA molecules of patients RCC75, RCC98, RCC100, RCC103, RCC112, RCC115, RCC116, RCC130, NCH359 and NCH361. The peptides associated with HLA-A*02 had an allele-specific peptide motif: on position 2, leucine, valine, isoleucine, alanine, or methionine were found, and at the C-terminus leucine, valine, isoleucine, or alanine. Most of the ligands were derived from so-called "housekeeping" proteins, however, ligands from tumor-associated proteins could be identified as well. For example, fragments from tenascin-C could be identified (GLAPSIRTK, SEQ ID NO. 2; GVLKKVIRH, SEQ ID NO. 20). Herold-Mende et al., Clinical Impact and Functional Aspects of Tenascin-C Expression during Glioma Progression, 2002, Int. J. Cancer, 9S: 362-369, show that in general the strength of the expression of the extracellular matrix protein tenascin-C correlates with the severity of the disease and the immigration of tumor cells in healthy tissue.

1.5. Detection of Peptide-Specific T Cells in the Normal CD8+ T Cell Repertoire

For detection of peptide-specific T cells, for example specific for the peptide with the sequence FPSLREAAL (SEQ ID NO. 114), mononuclear cells from peripheral blood of healthy subjects were stained with the corresponding HLA-A* subtype tetramers constituted with the respective peptides: To generate the tetramers, recombinant HLA-B* subtype molecules were constituted in vitro with the peptides, purified by gel filtration, biotinylated, and mixed with streptavidin for linking the monomers, as described by Walter S. et al., 2003, Cutting Edge Predetermined Avidity of Human CD8 T Cells Expanded on Calibrated MHC/Anti-CD2S-Coated Microspheres, J. Immunol. 171: 4974-4978.

Basically, the results of the double staining are measured by FACS analysis, and the specific binding of the peptide tetramers is detected (Walter S. et al., 2003, Cutting Edge: Predetermined Avidity of Human CD8 T Cells Expanded on Calibrated MHC/Anti-CD2S-Coated Microspheres, J. Immunol. 171: 4974-4978).

EXAMPLE 2

To analyze the presentation of the selected peptides by tumor cells and the recognition of the peptides by CTL, CTL were induced in vitro that are specific for the chosen peptides. For this purpose, KM22 and JY target cell lines were used.

2.1. Recovery of the Specific T Lymphocytes

Specific T lymphocytes were isolated from the blood of healthy subjects as described in 1.5 and concentrated by FACS sorting.

2.2. Peptide Synthesis

The peptides chosen as an example were synthesized using F-moc (9-fluorenylmethyloxycarbonyl) protection groups on a peptide synthesizer (432A, Applied Biosystems, Weiterstadt, Germany) and analyzed by "reversed phase" HPLC and mass spectroscopy. Thereby, sufficient amounts of the identified peptides could be produced.

2.3. Induction of an Antigen-Specific CTl Response Using Restricted Synthetic Peptides For CTL induction, the T lymphocytes obtained in step 2.1 ($5 \times 10^6$ T lymphocytes per well) were co-incubated by in vitro restimulation in 24-well plates with $1 \times 10^6$ irradiated target cells per well in 1.5 mL T cell medium [consisting of RPMI 1640, 25 mM HEPES (Life Technologies/Invitrogen, Karlsruhe, Germany)] with 10% heat-inactivated human AB serum (CC Pro, Neustadt/Weinstraβe, Germany), 2 mM L-glutamine, 50 U/mL penicillin, 50 mg/mL streptomycin, and 20 μg/mL gentamicine (all from Bio Whittaker/Cambrex, Verviers, Belgium). Additionally, 5 ng/mL human IL-12 p70 (R&D Systems) were added. After approximately 4 days co-incubation at 37° C., fresh medium was added with 20 U/mL human IL-2 (R&D Systems), and the cells were incubated for another 3 to 4 days. This stimulation cycle was repeated twice.

2.4. CTL Assay

For the CTL assays, KM22 and JY tumor cell lines were used as target cells. Peptide-pulsed cells were pulsed with 50 μg/mL peptide for 2 hours. All target cells were labeled in RP10 medium (RPMI 1640, supplemented with 10% heat-inactivated fetal calf serum and antibiotics) for 1 hour at 37° C. with [$^{51}$Cr] sodium chromate ($^{51}$Cr). Then, $10^4$ cells/well were added to a 96-well round bottom plate. Various numbers of CTL were added to obtain an end volume of 200 μL, with subsequent incubation for 4 hrs at 37° C. Then, supernatants (500 μL/well) were harvested and counted in a beta-plate counter. Specific lysis was calculated in percent as follows: 100×(experimental release−spontaneous release/maximum release−spontaneous release). Each, spontaneous and maximum release were determined in presence of either medium or 2% Triton X-100.

2.5. Results of the CTL Induction a) CTL Cytotoxic Activity Compared to Peptide-Pulsed Target Cells

In $^{51}$Cr release assays (see 2.4.) the cytotoxic activity of induced CTL (see 2.3.) was tested and compared to KM22 and JY cells. Cell lines KM22 and JY are HLA-B*07 positive.

Figure 1A:
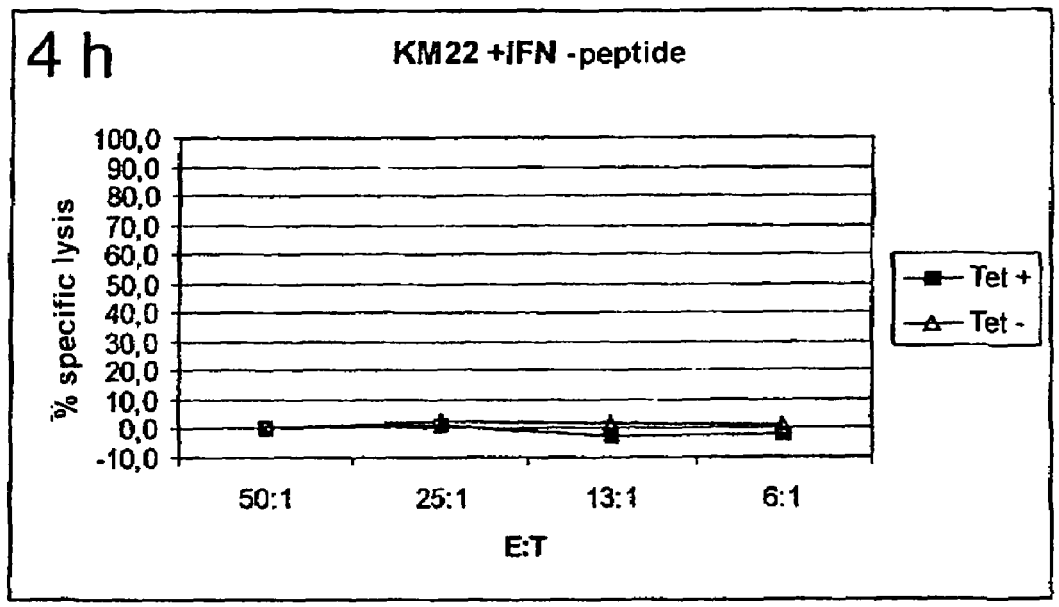
FIG. 1a shows the negative control regarding CTL-specific lysis of KM22 target cells (without peptide)
Figure 1B:
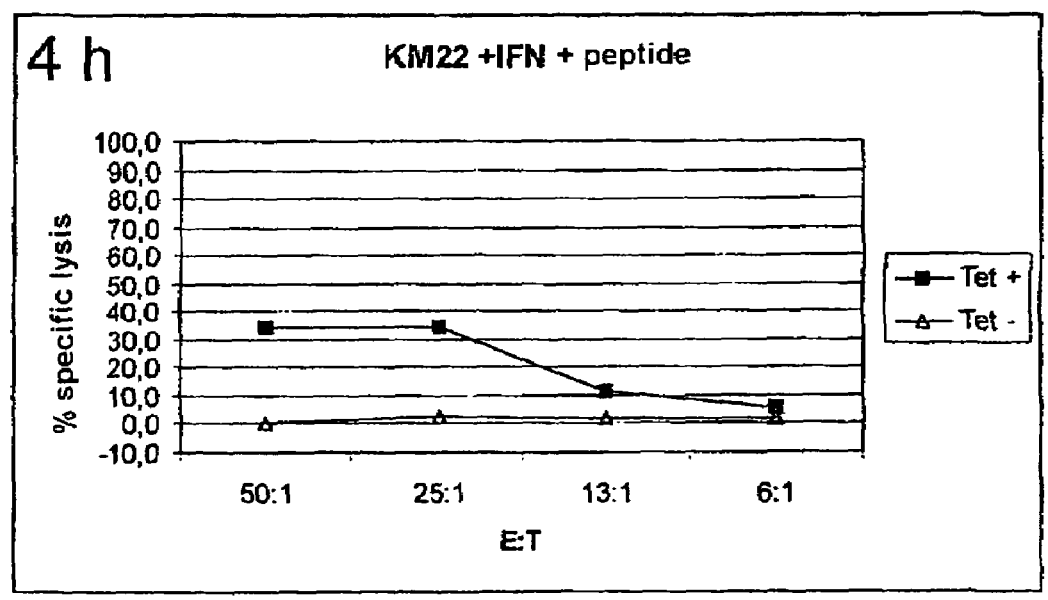
FIG. 1b shows the CTL-specific lysis of KM22 target cells pulsed with peptide and treated with interferon gamma.

The results of these release assays are shown in FIGS. 1a and 1b. In FIGS. 1a and 1b, the abbreviation "IFN" stands for interferon gamma, "E:T" stands for the ratio of effector to target cells, "Tet+" stands for T lymphocytes binding to HLAB*0702/FPSLREAAL (SEQ ID NO: 114) tetramers, and "Tet-" stands for T lymphocytes not binding to HLA-B*0702/FPSLREAAL (SEQ ID NO: 114) tetramers.

The results show that an antigen-specific kill of the cells can be obtained with CTL cell lines that have been obtained after restimulation for 2 weeks.

In FIG. 1a is shown that KM22 target cells treated with interferon gamma and positive for HLA allele B*0702 without peptide were not recognized by specific cytotoxic T lymphocytes. FIG. 1b shows that KM22 target cells, treated with interferon gamma, positive for HLA allele B*0702 presenting the peptide with the sequence FPSLREAAL from the tumor antigen MAGE-1 are recognized and lysed by specific cytotoxic T lymphocytes. Thus, only those cells were killed by an increasing number of CTL that presented the respective selected peptides; the control cells loaded with irrelevant peptides were not killed. By this, the specificity of the cytolytic activity could be demonstrated.

b) Production of Interferon Gamma by Peptide-Stimulated T Lymphocytes

In another experiment it was shown that the cytotoxic T lymphocytes lysing the T2 cells loaded with peptide FPSL-REAAL (SEQ-ID NO. 114) also expressed interferon gamma which has been described as a reliable marker for activation of T cells.

Figure 2:
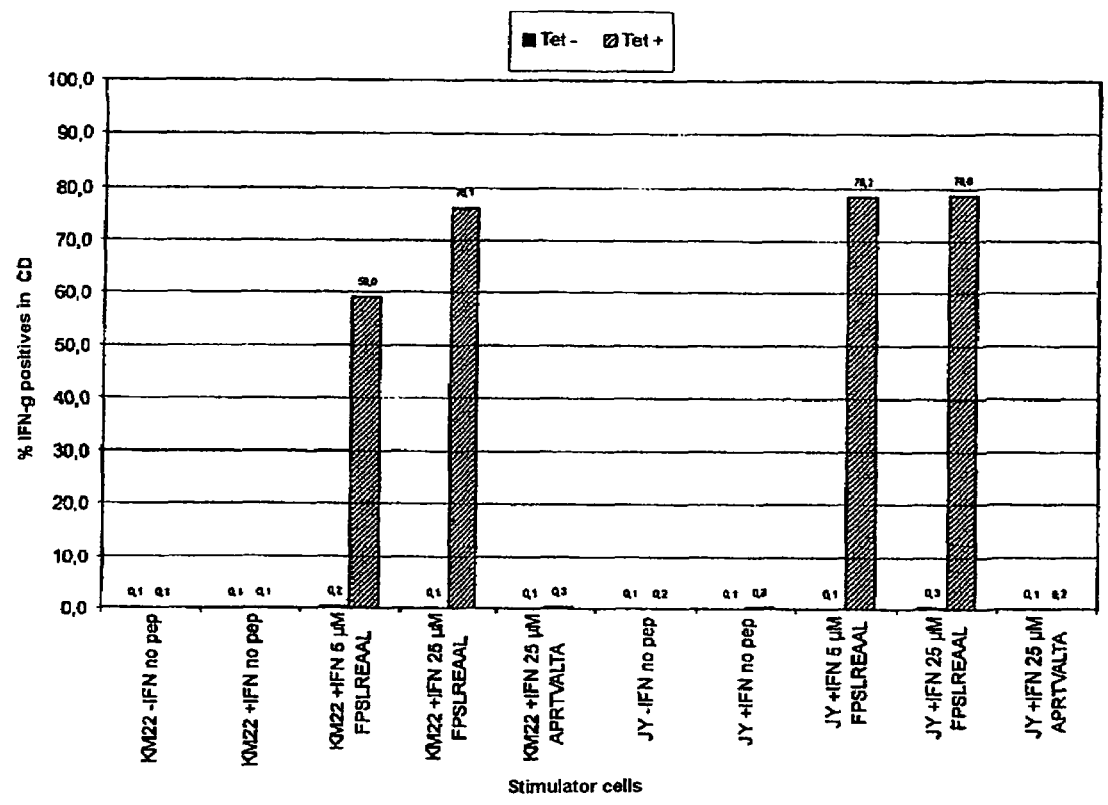
FIG. 2 shows the production of interferon gamma by specific T lymphocytes upon stimulation by KM22 or JY cells loaded with peptide.

In FIG. 2, the results of the measurements are shown, with KM22 and JY cells being tested. The same abbreviations as in FIG. 1 were used, with "CD8+" describing T lymphocytes expressing the receptor molecule CD8 on the cell surface.

To detect IFN gamma, $1 \times 10^5$ effector cells and stimulator cells that have been pulsed with peptide were grown in T cell medium on 96-well plates (T cell medium: RPMI 1640 with 25 mM HEPES (Gibco/Invitrogen, Karlsruhe, Germany; supplemented with 10% heat-inactivated human AB serum (CC pro, Neustadt/W., Germany; 2 mM L-glutamine, 50 U/mL penicillin, 50 μg/mL streptomycin and 20 μg/mL gentamycine (all from BioWhittaker). The loading with peptides was conducted in X-Vivo 15 medium with the respective peptides für approx. 2 hrs at 37° C.

After 1 to 2 hrs GolgiStop (Becton Dickinson) was added and incubated for another 4 to 5 hrs. Then, the cells were permeabilized and stained by using the Cytofix/Cytoperm Plus kit as well as anti-CD4-FITC, anti-IFN-γ-PE and anti-CD8-PerCP according to the manufacturer's recommendations (Becton Dickinson). The cytometric analysis was performed using a FACSCalibur cytometer.

As can be seen from FIG. 2, T lymphocytes binding to HLA-B*0702/FPSLREAAL (SEQ ID NO: 114) tetramer (=specific T lymphocytes, "Tet+") produce interferon gamma, when they are stimulated with KM22 or JY cells, each pretreated with various amounts of interferon gamma and loaded with peptide with SEQ ID NO. 114 (see FIG. 2, "KM22+FPSLREAAL (SEQ ID NO: 114)" and "JY+FPSL-REAAL (SEQ ID NO: 114)", each pretreated with 5 or 25 pM INF). In contrast, unspecific T lymphocytes (which do not bind to the HLA-B*0702/FPSLREAAL (SEQ ID NO: 114) tetramer) do not produce any interferon gamma (="Tet-").

Furthermore, FIG. 2 shows that neither the specific (="Tet+") nor the unspecific ("Tet-") T lymphocytes produced interferon gamma if they were stimulated with an unspecific control peptide (in FIG. 2 as an example: APRTVALTA, SEQ ID NO. 585) (see FIG. 2 for "Tet+n and "Tet-", respectively: "KM22+APRTVALTA (SEQ ID NO. 585)" and "JY+APRTVALTA (SEQ ID NO. 585)", each pretreated with 25 μM INF).

c) Peptide-Specific Stimulation of CD8-Positive T Cells

For further determination of the peptide-specific stimulation of CD8-positive T cells the peptide with sequence LAALPHSCL (SEQ ID NO. 448) from protein RGS-5 and the control peptide with sequence ELAGIGILTV (SEQ ID NO. 578) from melanoma antigen MELAN-A (position 26-35, modified by an amino acid exchange of the alanine at position 27 by leucine) were synthesized using standard Fmoc chemistry, with the control peptide also binding to the HLA allele A*02. Biotinylated recombinant A*02 molecules and fluorescent MHC tetramers were generated as described by Altman et al. ("Phenotypic analysis of antigen-specific T lymphocytes", Science 274:94, 1996). To generate artificial antigen presenting cells ("APCs"), streptavidin-coated polystyrene particles (5.6 μm diameter) with a binding capacity of 0.064 μg biotin-FITC/mg microspheres (Bangs Laboratories, Fishers, Ill., USA) were resuspended with $2 \times 10^6$ particles/mL in a buffer containing the biotinylated MHC and the antibodies, and incubated for 30 min. at room temperature.

For the antigen-specific in vitro stimulation of the human CD8 T cells, PBMC from fresh buffy coat were isolated by standard gradient separation. Untreated CD8 T cells were concentrated by negative depletion using MACS (Miltenyi Biotec, Bergisch Gladbach, Germany). The in vitro stimulations were performed on 24-well plates with $5 \times 10^6$ responder cells and $1 \times 10^6$ beads or $1 \times 10^6$ irradiated APCs per well in 1.5 mL T cell medium (compare supra). 5 ng/mL human IL-12 p70 (R&D Systems, USA) were added together with microspheres. After 3 to 4 days co-incubation at 37° C., fresh medium and 20 U/mL human IL-2 (R&D Systems, USA) were added, and the cells were incubated for another 3 to 4 days. This stimulation cycle was repeated twice.

For the cell surface and intracellular cytometric analysis, tetramer analyses with fluorescent MHC tetramers plus anti-CD8 antibodies (hybridoma UKT8) were conducted on a four-color FACSCalibur (Becton Dickinson).

Figure 3:
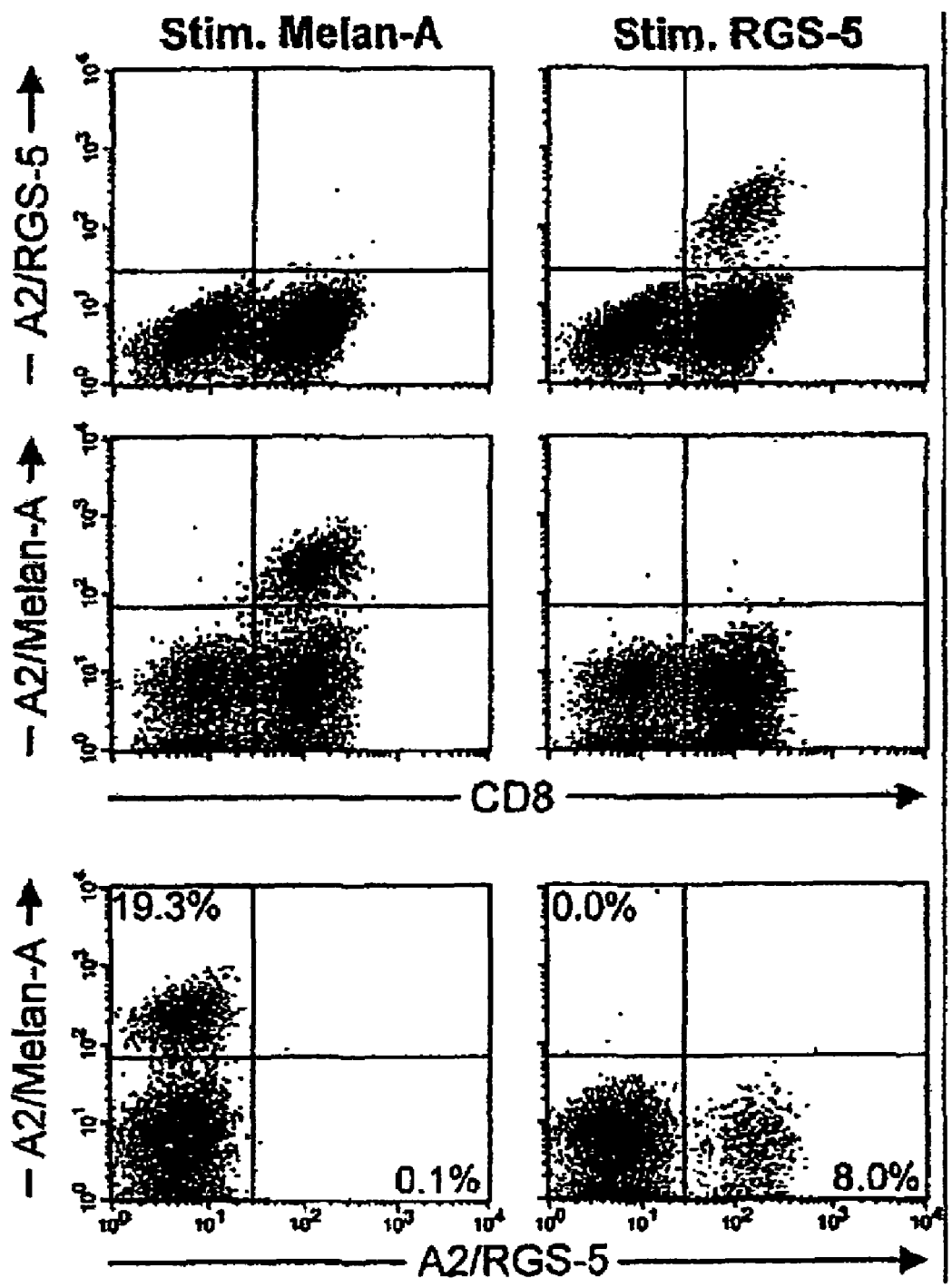
FIG. 3 shows the peptide-specific stimulation of human CD8-positive T cells.

The results of these analyses are shown in FIG. 3. It can be seen that the RGS-5 peptide with SEQ ID NO. 448 specifically stimulates human CD8-positive T cells. In FIG. 3, in the left column, the analysis of PBMC T cells is shown that have been stimulated twice with a control peptide with the sequence ELAGIGILTV from melan-A (SEQ ID NO. 578), as described above.

The right column shows the analyses of T cells that have been stimulated with the RGS-5 peptide with the sequence LAALPHSCL (SEQ ID NO. 448).

In the top left of FIG. 3 is shown that CD8-positive α-axis) T cells stimulated with melan-A peptide/MHC-A*02 tetramer complexes do not bind to MHC-A*02 tetramers complexed with the peptide with the sequence LAALPHSCL (SEQ ID NO. 448) (y-axis).

In the top right of FIG. 3 is shown that CD8-positive T cells, stimulated with RGS-5 peptide with the sequence LAALPHSCL/MHC-A*02 tetramer complexes, bind to MHC-A*02 tetramers complexed with the peptide with the sequence LAALPHSCL (SEQ ID NO. 448) (y-axis). The double-stained (double-positive) cells are shown in the upper right quadrant.

In FIG. 3, left middle, is shown that CD8-positive T cells (x-axis) stimulated with melan-1 peptide/MHC-A*02 tetramer complexes, bind to MHC-A*02 tetramers complexed with the peptide with the sequence ELAGIGILTV (SEQ ID NO. 579) from melan-A (y-axis). The double stained (double positive) cells are shown in the upper right quadrant. In the right middle is shown that CD8-positive T cells, stimulated with complexes from RGS-5 peptide with the sequence LAALPHSCL and MHC-A*02 tetramers, not bind to MHC-A*02 tetramers complexed with the peptide with the sequence ELAGIGILTV (SEQ ID NO. 579) from melan-A (y-axis).

In the bottom row of FIG. 3, on the left hand side, the proportional numbers of the melan-A/MHC-A*02-specific T cells are shown by double staining with the two applied MHC tetramer-peptide complexes (melan-A/MHC-A*02 and RGS-5/MHC-A*02). After prior stimulation with melan-A peptide/MHC-A*02 tetramer complexes bound on artificial antigen presenting cells, 19.3% of the stimulated cells bind specifically to the MHC tetramer complex of melan-A peptide and HLA-A*02. On the bottom right hand side, the proportional numbers of the RGS-5/MHC-A*02-specific T cells are shown by double staining with the two applied MHC tetramer complexes (melan-A/MHC-A*02 and RGS-5/MHC-A*02). After prior stimulation with RGS-5 peptide/MHC-A*02 tetramer complexes bound on artificial antigen presenting cells, 8.0% of the stimulated cells bind specifically to the MHC tetramer complex of RGS-5 peptide with the sequence LAALPHSCL (SEQ ID NO. 448) and HLA-A*02.

d) Detection of Peptide-Specific T Cells in Blood from Renal Cell Carcinoma Patients In further experiments, peptide-specific T cells from blood from renal cell carcinoma patients previously immunized with peptide-loaded autologous dendritic cells could be detected.

For this detection, a quantitative real-time polymerase chain reaction (RT-PCR) was performed. This RT-PCR was conducted as described by Kammula et al. (Kammula et al., Journal of Immunology 163:6867, 2000). For this, PBMCs were thawed in T cell medium, plated out with $1 \times 10^6$ cells in 500 µL medium and incubated over night with 5% $CO_2$ at 37° C. Then, the synthetic peptides were added with 5 µg/mL for 3 hours, and then an RNA extraction with Trizole (Invitrogen, Karlsruhe, Germany) was performed. The cDNA was transcribed using random hexamer primers (Amersham Biosciences, Freiburg, Germany) and M-MLV reverse transcriptase (Promega GmbH, Mannheim, Germany).

The quantitative RT-PCR was performed on an "ABIPrism 7000 Sequence Detection System" (Applied Biosystems, Darmstadt, Germany) in duplicate in respect to IFN gamma mRNA and CD8 mRNA, using the Taqman PCR master mix (Applied Biosystems), specific primers and fluorescent probes.

The results represent the copy number of IFN gamma mRNA, with each sample being normalized regarding the CD8 mRNA copy number (used as reference gene product) (stimulation index).

The gene expression in presence of the tested peptides is relative to the gene expression obtained in presence of the controls (HLA-A*02 epitope derived from HIV1 pol with the sequence ILKEPVHGV, SEQ ID NO. 579) (copy number of the control was set to 1).

Figure 4:
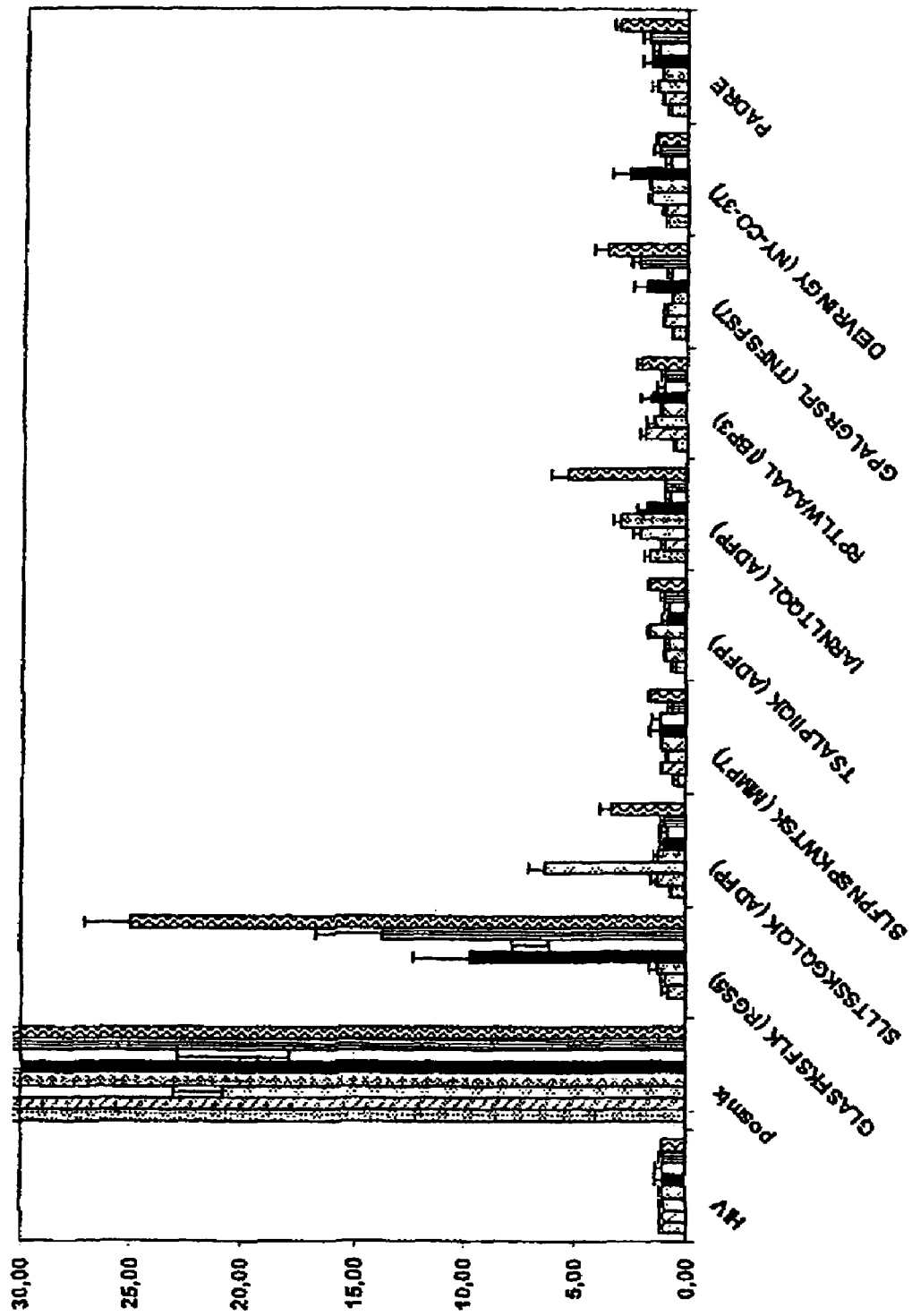
FIG. 4 shows the detection of peptide-specific T cells in blood from renal cell carcinoma patients.

In FIG. 4 the results of these studies are shown. The diagram in FIG. 4 shows the ex vivo T cell activation after immunization of the patient RCC98 at the University Hospital in Tübingen with nine HLA-binding peptides. The first two out of 11 column blocks show the negative and positive controls of the T cell experiment. The error bars represent the standard deviation. As mentioned above, the HIV peptide with the sequence ILKEPVHGV (from the viral antigen HIV1 pol, position 896-904; SEQ ID NO. 579) was used as negative control. The negative control did not lead to a T cell response if the patient was seronegative for HIV. As a positive control, a mixture of peptides from influenza matrix 58-66 (GILGFVFTL; SEQ ID NO. 580), HCMVA pp 65 495-503 (NLVPMVATV; SEQ ID NO. 581), EBNA6-EBV 284293 (LLDFVRFMGV; SEQ ID NO. 582), IE63-EBV 259-267 (GLCTLV AML; SEQ ID NO. 583), and LMP2-EBV 294-302 (CLGGLLTMV; SEQ ID NO. 584) was used, with which as very strong T cell response could be expected ("posmix"; Maximum: stimulation index 43.6). All control peptides for PBMC stimulation were used in a concentration of 5 µg/mL. The background was defined as standard deviation of the negative control (stimulation index 1.35, shown as horizontal dashed line).

In FIG. 4, the next nine column blocks of the diagram show the T cell activations measured against nine immunized peptides. These nine peptides were administered together subcutaneously, altogether seven times in increments of 14 days, loaded onto autologous dendritic cells. Therefore, each column block consists of eight columns (before the $1^{st}$ immunization, after the $1^{st}$ immunization, after the $2^{nd}$ immunization, etc.). Therefore, each column block shows the progression of the T cell responses in the course of the immunizations.

Starting after the $3^{rd}$ immunization already, strong T cell responses were obtained for GLASFKSFLK (RGS-5 74-83, SEQ ID NO. 153) and SLLTSSKGQLQK (ADFP 369-380, SEQ ID NO. 289), whereby for the last peptide the T cell responses increased after the $4^{th}$ immunization. Such fluctuations of the T cell response during the course of an immunization therapy are known from other patients as well.

For IARNLTQQL (ADFP 313-321; SEQ ID NO. 233), GPALGRSFL (TNFSF7 78-86, SEQ ID NO. 577) the T cell responses were clearly in the background, and were weaker for a known pan-HLA DR-binding (PADRE) peptide. For these three peptides, an increase of the T cell response was also observed during the course of the immunization therapy (dotted lines). This confirmed that these three latter peptides have elicited a positive T cell response.

The patient was immunized as part of a registered clinical study at the University Hospital in Tübingen, Germany. The clinical study was applied and approved in written form by the Ethical Committee of the University of Tübingen, Germany. The study was conducted according to the rules and regulations of the German Medicines Act (Arzneimittelgesetz) and the good clinical practice (GCP).

In summary, the inventors were thereby able to show that the identified peptides represent promising substances as part of an immunotherapy for a variety of (tumor) diseases.

EXAMPLE 3

Tetramer analysis of the microsphere-driven proliferation of B*0702/IARNLTQQL (SEQ ID NO. 233)-specific CD8+ lymphocytes from peripheral blood (see FIG. 5).

$1 \times 10^6$ CD8+ enriched PBMCs per well from six healthy HLA-A*0201+ donors HD155, HD159, HD161, HD167, 00168 and 00177, were stimulated weekly with microspheres coupled to anti-CD28 plus irrelevant antigen ("irrelevant stimulation"), tumor antigen B*0702/IARNLTQQL with high density ("HD") or tumor antigen B*0702/IARNLTQQL with low density ("LD") as previously shown [Walter, S, et al. Cutting Edge: Predetermined avidity of human CD8 T cells expanded on calibrated MHC/anti-CD28-coated microspheres. J. Immunol. 171 (1 0):4974-8, 2003] with minor modifications. After three stimulations in vitro, individual wells were stained with antibody CD8 plus tetramer B*0702/IARNLTQQL. Each dot represents the percentage of tetramer+among CD8+ lymphocytes from one well.

Based on the distribution of observed responses after irrelevant stimulation in individual donors, a significant threshold was calculated, and shown by a horizontal red line using the following formula:

Threshold=upper limit of 95% confidence interval for the mean+3×upper limit of 95% confidence interval for the standard deviation The numbers in the diagrams show the number of significantly positive wells among total wells for the indicated condition.

TABLE 1

| | Sequence | Position/ Gene symbol | Acc. No. | SEQ ID NO. |
|---|---|---|---|---|
| | | Sequences of NCH359 | | |
| 1. | VPDSSGPERIL | 78-88 HNRPK | NP_002131.2 | SEQ ID NO. 1 |
| 2. | GLAPSIRTK | 1510-1518 TNC | NP_002151.1 | SEQ ID NO. 2 |
| 3. | RLFEHPLYR | 149-157 FAM20C | NP_064608.1 | SEQ ID NO. 3 |
| 4. | TPSEPHPVL | 381-389 HGRG8 | NP_057342.1 | SEQ ID NO. 4 |
| 5. | QIFVKTLTGK | 2-11 RPS27A | AAH01392.1 | SEQ ID NO. 5 |
| 6. | SLMHSFILK | 44-52 DNCL2A | NP_054902.1 | SEQ ID NO. 6 |
| 7. | YPHLHNAEL | 127-135 SOX9 | NP_000337.1 | SEQ ID NO. 7 |
| 8. | RLFVGSIPK | 244-252 SYNCRIP | NP_006363 | SEQ ID NO. 8 |
| 9. | RVFPDKGYSF | 233-242 TIA1 | NP_071320.1 | SEQ ID NO. 9 |
| 10. | SLYKKLEIK | 554-562 SLC9A2 | NP_003039.2 | SEQ ID NO. 10 |
| 11. | HPVSDHEATL | 216-225 HLA-C | NP_002108 | SEQ ID NO. 11 |
| 12. | LPTRVDFSL | 46-54 Symbol does not exist; Gene type: unnamed protein product | BAC87610 | SEQ ID NO. 12 |
| 13. | KSFGSAQEFAW | 386-396 COPB2 | NP_004757 | SEQ ID NO. 13 |
| 14. | SPSTSRTPLL | 1026-1035 EGFR | NP_005219.2 | SEQ ID NO. 14 |
| 15. | STFDSPAHW | 1149-1157 EGFR | NP_005219.2 | SEQ ID NO. 15 |
| 16. | APEEHPVLL | 97-105 ACTB | NP_001092.1 | SEQ ID NO. 16 |
| 17. | RQITQVYGF | 117-125 PPP6C | NP_002712.1 | SEQ ID NO. 17 |

TABLE 1-continued

| | Sequence | Position/Gene symbol | Acc. No. | SEQ ID NO. |
|---|---|---|---|---|
| 18. | KVSDYILQH | 1046-1054 ASTN2 | NP_054729.3 | SEQ ID NO. 18 |
| 19. | KLLPSVVLK | 2-10 DTR | NP_001936.1 | SEQ ID NO. 19 |
| 20. | GVLKKVIRH | 23-31 TNC | NP_002151.1 | SEQ ID NO. 20 |
| 21. | KLFDHAVSKF | 40-49 ACSL4 | NP_004449.1 | SEQ ID NO. 21 |
| 22. | ITVLTKPLPV | 112-121 PTPRO | NP_002839.1 | SEQ ID NO. 22 |
| 23. | HPVHPDIKL | 130-138 PIAS1 | NP_057250.1 | SEQ ID NO. 23 |
| 24. | IPRAALLPLL | 3-12 PRSS11 | NP_002766.1 | SEQ ID NO. 24 |
| 25. | ATNRITVTW | 254-262 PIASY | NP_056981.2 | SEQ ID NO. 25 |
| 26. | KIADRFLLY | 29-37 LMO4 | NP_006760.1 | SEQ ID NO. 26 |
| | Sequences of NCH361 | | | |
| 27. | DHDPVDKIVL | 150-159 HNRPA2B1 | NP_002128.1 | SEQ ID NO. 27 |
| 28. | DHHQEVIGF | 165-173 C9ORF10 | NP_055427.2 | SEQ ID NO. 28 |
| 29. | IHDLDNISF | 188-196 PSMB2 | NP_002785.1 | SEQ ID NO. 29 |
| 30. | DHINDIIKI | 834-842 IQGAP1 | NP_003861.1 | SEQ ID NO. 30 |
| 31. | DHMRFISEL | 355-363 CYFIP1 | NP_055423.1 | SEQ ID NO. 31 |
| 32. | THSLPVVVI | 456-464 STAT3 | NP_003141.2 | SEQ ID NO. 32 |
| 33. | MPVGPDAILRY | 929-939 BAT3 | NP_004630.2 | SEQ ID NO. 33 |
| 34. | RLDDAIHVL | 406-414 TCF12 | NP_003196.1 | SEQ ID NO. 34 |
| 35. | QHEGTVNIF | 1953-1961 PTPRZ1 | NP_002842.1 | SEQ ID NO. 35 |
| 36. | ETVNIWTHF | 48-56 PAQR6 | NP_940798 | SEQ ID NO. 36 |
| 37. | VHILDTETF | 195-203 KLHDC2 | NP_055130.1 | SEQ ID NO. 37 |
| 38. | QTPDFTPTKY | 607-616 ZHX3 | NP_055850.1 | SEQ ID NO. 38 |
| 39. | RHVEVFELL | 133-141 MPDZ | NP_003820.1 | SEQ ID NO. 39 |
| 40. | TTIDIGVKY | 136-144 CNN3 | NP_001830.1 | SEQ ID NO. 40 |
| 41. | DLIEHFSQF | 113-121 HNRPA0 | NP_006796.1 | SEQ ID NO. 41 |
| 42. | ETVWRLEEF | 65-73 HLA-DRA | NP_061984 | SEQ ID NO. 42 |

TABLE 1-continued

| | Sequence | Position/Gene symbol | Acc. No. | SEQ ID NO. |
|---|---|---|---|---|
| 43. | DVLESVNLL | 176-184 AP2M1 | NP_004059.2 | SEQ ID NO. 43 |
| 44. | IHDDFVTTF | 466-474 AEBP1 | NP_001120.2 | SEQ ID NO. 44 |
| 45. | IHIPINNII | 57-65 Sec61G | NP_055117.1 | SEQ ID NO. 45 |
| 46. | IHLIDPNTL | 281-289 CGI-07 | NP_057022.2 | SEQ ID NO. 46 |
| 47. | IHVIGGNDV | 1016-1024 KIAA1268 | XP_291055.1 | SEQ ID NO. 47 |
| 48. | KAFQKIVVL | 291-299 BZW1 | NP_055485.2 | SEQ ID NO. 48 |
| 49. | YQDLLNVKL | 349-357 GFAP | NP_002046.1 | SEQ ID NO. 49 |
| 50. | GHYEVAELL | 728-736 TNKS | NP_003738.1 | SEQ ID NO. 50 |
| 51. | LVVYPWTQRF | 33-42 HBB | NP_000509.1 | SEQ ID NO. 51 |
| 52. | MHLRQYELL | 386-393 GNAS | NP_000507.1 | SEQ ID NO. 52 |
| 53. | EAIEQILKY | 149-157 FLJ10539 | NP_060600.1 | SEQ ID NO. 53 |
| 54. | DVAEGDLIEHF | 108-118 HNRPA0 | NP_006796.1 | SEQ ID NO. 54 |
| 55. | DVLQKIKY | 191-198 EPS8L1 | NP_060199.2 | SEQ ID NO. 55 |
| 56. | DSFPMEIRQY | 24-33 STAT1 | NP_009330.1 | SEQ ID NO. 56 |
| 57. | DVISNIETF | 281-289 SOX9 | NP_000337.1 | SEQ ID NO. 57 |
| 58. | DVIRLIMQY | 9-17 SMU-1 | NP_060695.1 | SEQ ID NO. 58 |
| 59. | DVIERVIQY | 792-800 IDN3 | NP_056199.1 | SEQ ID NO. 59 |
| 60. | DVIAQGIGKL | 53-62 RPLP2 | NP_000995.1 | SEQ ID NO. 60 |
| 61. | DVFNEKGWNY | 94-103 PBEF1 | NP_005737.1 | SEQ ID NO. 61 |
| 62. | THLDSVTKI | 254-262 C6.1A | NP_077308.1 | SEQ ID NO. 62 |
| 63. | DVAGIIADY | 294-302 KIAA1238 | XP_048675.4 | SEQ ID NO. 63 |
| 64. | TAAPFPFHL | 536-544 TBX2 | NP_005985.2 | SEQ ID NO. 64 |
| 65. | DTLDKVFTY | 86-94 ACSL3 | NP_004448.2 | SEQ ID NO. 65 |
| 66. | DTISPTLGF | 42-50 ARL2 | NP_001658.1 | SEQ ID NO. 66 |
| 67. | DTGILDSIGRF | 35-45 MBP | NP_002376.1 | SEQ ID NO. 67 |

TABLE 1-continued

| | Sequence | Position/Gene symbol | Acc. No. | SEQ ID NO. |
|---|---|---|---|---|
| 68. | VVYPWTQRF | 34-42 HBB | NP_000509.1 | SEQ ID NO. 68 |
| 69. | EVVAGIKEYF | 128-137 MORF4 | NP_006783.2 | SEQ ID NO. 69 |
| 70. | SSVPGVRLL | 72-80 VIM | NP_003371.1 | SEQ ID NO. 70 |
| 71. | SVVDAIGISRF | 364-374 FLJ45273 | BAC86883.1 | SEQ ID NO. 71 |
| 72. | EVIPPMKEF | 115-123 NDUFB6 | NP_002484.1 | SEQ ID NO. 72 |
| 73. | EVIPPYYSY | 152-160 TTRAP | NP_057698.2 | SEQ ID NO. 73 |
| 74. | EVNGLISMY | 284-292 U5-116KD | NP_004238.2 | SEQ ID NO. 74 |
| 75. | EVIDLMIKEY | 57-66 PHF10 | NP_060758.1 | SEQ ID NO. 75 |
| 76. | EVVAGIKEY | 128-136 MORF4 | NP_006783.2 | SEQ ID NO. 76 |
| 77. | EVFPLAMNY | 76-84 CCND1 | NP_444284.1 | SEQ ID NO. 77 |
| 78. | EVVERVLTF | 28-36 FBXO22 | NP_036302.1 | SEQ ID NO. 78 |
| 79. | SHSPFGLDSF | 1251-1260 JMJD1B | NP_057688.2 | SEQ ID NO. 79 |
| 80. | FGVDRAILY | 457-465 ITGAV | NP_002201.1 | SEQ ID NO. 80 |
| 81. | SHSDYLLTI | 76-84 SOCS2 | NP_003868.1 | SEQ ID NO. 81 |
| 82. | SHLDYDITL | 511-519 KIAA0794 | XP_087353.5 | SEQ ID NO. 82 |
| 83. | SHFVSDVVI | 63-71 GNB2L1 | NP_006089.1 | SEQ ID NO. 83 |
| 84. | EVTELLARY | 155-163 POLR2E | NP_002686.2 | SEQ ID NO. 84 |
| 85. | ETADTLMGLRY | 425-435 GFPT1 | NP_002047.1 | SEQ ID NO. 85 |
| 86. | EHAHLIVVL | 662-670 ABCB9 | NP_062570.1 | SEQ ID NO. 86 |
| 87. | EHSLVIDTL | 53-61 PFDN2 | NP_036526.2 | SEQ ID NO. 87 |
| 88. | EIAEAYLGY | 129-137 HSPA1A | NP_005336.2 | SEQ ID NO. 88 |
| 89. | EIYGGSDSRF | 42-51 SF3B1 | NP_036565.1 | SEQ ID NO. 89 |
| 90. | ELIAKIPNF | 73-81 SET | NP_003002.1 | SEQ ID NO. 90 |
| 91. | EVIKNFIQY | 50-58 EIF3S6IP | NP_057175.1 | SEQ ID NO. 91 |
| 92. | ETADTLLALRY | 426-436 GFPT2 | NP_005101.1 | SEQ ID NO. 92 |

TABLE 1-continued

| | Sequence | Position/Gene symbol | Acc. No. | SEQ ID NO. |
|---|---|---|---|---|
| 93. | EVVSEPFRSF | 581-590 PSMD2 | NP_002799.3 | SEQ ID NO. 93 |
| 94. | ETFDAGLQAF | 2019-2028 SPTAN1 | NP_003118.1 | SEQ ID NO. 94 |
| 95. | SHSQLMQLI | 164-172 ADRM1 | NP_008933.2 | SEQ ID NO. 95 |
| 96. | ETVRELTEF | 255-263 PPARD | NP_006229.1 | SEQ ID NO. 96 |
| 97. | EVAATEIKM | 10-18 HNRPM | NP_005959.2 | SEQ ID NO. 97 |
| 98. | EVAAVLLHF | 214-222 SEC10L1 | NP_006535.1 | SEQ ID NO. 98 |
| 99. | EVFDKTYQF | 132-140 C6orf153 | NP_149103.1 | SEQ ID NO. 99 |
| 100. | ELVKRILNF | 174-182 DEK | NP_003463.1 | SEQ ID NO. 100 |
| 101. | AHDDGRWSL | 95-103 FSCN1 | NP_003079.1 | SEQ ID NO. 101 |
| 102. | SVVSVISRF | 4-12 DAD1 | NP_001335.1 | SEQ ID NO. 102 |
| 103. | SVVELINHY | 132-140 PIK3R3 | NP_003620.2 | SEQ ID NO. 103 |
| 104. | SVVDLINHY | 397-405 PIK3R2 | NP_005018.1 | SEQ ID NO. 104 |
| 105. | AHVDLIEKL | 51-59 POLR2L | NP_066951.1 | SEQ ID NO. 105 |
| 106. | FHNELLTQL | 97-105 BAIAP2 | NP_006331.1 | SEQ ID NO. 106 |
| 107. | SVIEAVAHF | 812-820 C6orf133 | NP_056070.1 | SEQ ID NO. 107 |
| 108. | GHFEKPLFL | 149-157 NTE | NP_006693.2 | SEQ ID NO. 108 |
| 109. | GHDASQITL | 273-281 TH1L | NP_057481.2 | SEQ ID NO. 109 |
| 110. | SAVDFIRTL | 293-301 STK17A | NP_004751.1 | SEQ ID NO. 110 |
| 111. | ISTPVIRTF | 989-997 C9orf10 | NP_055427.2 | SEQ ID NO. 111 |
| 112. | GVIEKLLTSY | 28-37 D1S155E | AAH32446 | SEQ ID NO. 112 |
| 113. | SHDLTLVNL | 395-403 KIAA1706 | NP_085139.1 | SEQ ID NO. 113 |
| | Sequence of JY | | | |
| 114. | FPSLREAAL | 294-302 MAGEA1 | NP_004979.2 | SEQ ID NO. 114 |
| | Sequences of RCC075 | | | |
| 115. | SIFKQPVTK | 250-258 MBD2 | NP_003918.1 | SEQ ID NO. 115 |
| 116. | KPNANRIAL | 139-147 LGALS3 | NP_002297.1 | SEQ ID NO. 116 |

TABLE 1-continued

| Sequence | Position/Gene symbol | Acc. No. | SEQ ID NO. |
|---|---|---|---|
| 117. KLYEMILKR | 174-182 ARL7 | NP_005728.2 | SEQ ID NO. 117 |
| 118. SLFSRLFGK | 7-15 ARF4 | NP_001651.1 | SEQ ID NO. 118 |
| 119. KLFDKLLEY | 309-317 API5 | NP_006586.1 | SEQ ID NO. 119 |
| 120. SLFPNSPKWTSK | 96-107 MMP7 | NP_002414.1 | SEQ ID NO. 120 |
| 121. LESLDQLEL | 29-37 BAG2 | NP_004273.1 | SEQ ID NO. 121 |
| 122. VVNKVPLTGK | 101-110 MGC17943 | NP_689474.1 | SEQ ID NO. 122 |
| 123. SVYDSVLQK | 4470-4478 SYNE1 | NP_149062.1 | SEQ ID NO. 123 |
| 124. SVYVLVRQK | 39-47 MLSTD2 | NP_115604.1 | SEQ ID NO. 124 |
| 125. ILENIQRNK | 557-565 ERCC2 | NP_000391.1 | SEQ ID NO. 125 |
| 126. GSYNKVFLAK | 146-155 PSMD8 | NP_002803.1 | SEQ ID NO. 126 |
| 127. TESGLNVTL | 6-14 PCBP1 | NP_006187.1 | SEQ ID NO. 127 |
| 128. TEHGVEVVL | 612-620 SH2D3C | NP_005480.1 | SEQ ID NO. 128 |
| 129. TEARFGAQL | 327-335 KRT19 | NP_002267.2 | SEQ ID NO. 129 |
| 130. TLADILLYY | 114-122 EEF1E1 | NP_004271.1 | SEQ ID NO. 130 |
| 131. LVFPSEIVGK | 133-142 RPS7 | NP_001002.1 | SEQ ID NO. 131 |
| 132. VLFGKALNPK | 709-718 ABCC3 | NP_003777.2 | SEQ ID NO. 132 |
| 133. RPELVRPAL | 91-99 AKR1C3 | NP_003730.4 | SEQ ID NO. 133 |
| 134. VPNQKRLTLL | 576-585 ACSL4 | NP_004449.1 | SEQ ID NO. 134 |
| 135. QLYWSHPRK | 5-13 RPS29 | NP_001023.1 | SEQ ID NO. 135 |
| 136. SVYVYKVLK | 39-47 H2BFS | NP_059141.1 | SEQ ID NO. 136 |
| 137. REKLQEEML | 186-194 VIM | NP_003371.1 | SEQ ID NO. 137 |
| 138. RVFSGLVSTGLK | 415-426 EEF2 | NP_001952.1 | SEQ ID NO. 138 |
| 139. KPRDVSSVEL | 1939-1948 SPTBN1 | NP_003119.1 | SEQ ID NO. 139 |
| 140. NEFPEPIKL | 184-192 RAB7 | NP_004628.4 | SEQ ID NO. 140 |
| 141. KTYGEIFEK | 106-114 NDUFC2 | NP_004540.1 | SEQ ID NO. 141 |
| 142. RILFFNTPK | 196-204 PSMD8 | NP_002803.1 | SEQ ID NO. 142 |

TABLE 1-continued

| | Sequence | Position/Gene symbol | Acc. No. | SEQ ID NO. |
|---|---|---|---|---|
| 143. | RVFPWFSVK | 1764-1772 MLL | NP_005924.1 | SEQ ID NO. 143 |
| 144. | SEVQDRVML | 54-62 CGI-127 | NP_057145.1 | SEQ ID NO. 144 |
| 145. | SLWDRLIFH | 410-418 ACSL1 | NP_001986.2 | SEQ ID NO. 145 |
| 146. | KVYNIQIRY | 468-476 LCP2 | NP_005556.1 | SEQ ID NO. 146 |
| 147. | RLLEMILNK | 171-179 AKR1C2 | NP_001345.1 | SEQ ID NO. 147 |
| 148. | SEDKKNIIL | 41-49 CFL1 | NP_005498.1 | SEQ ID NO. 148 |
| 149. | YEELVRMVL | 106-114 MYL6 | NP_524147.1 | SEQ ID NO. 149 |
| 150. | GEITGEVHM | 1758-1766 FLNB | NP_001448.1 | SEQ ID NO. 150 |
| 151. | IVAGSLITK | 183-191 FNBP3 | AAH11788 | SEQ ID NO. 151 |
| 152. | APRIITGPAPVL | 225-236 QKI | NP_006766.1 | SEQ ID NO. 152 |
| 153. | GLASFKSFLK | 74-83 RGS5 | NP_003608.1 | SEQ ID NO.153 |
| 154. | FPNSPKWTSK | 98-107 MMP7 | NP_002414.1 | SEQ ID NO. 154 |
| 155. | FVIETARQL | 49-57 C14orf4 | NP_078772.1 | SEQ ID NO. 155 |
| 156. | IEVDGKQVEL | 46-55 RHOA | NP_001655.1 | SEQ ID NO. 156 |
| 157. | GELTGEVRM | 1776-1786 FLNC | NP_001449.1 | SEQ ID NO. 157 |
| 158. | GESDDSILRL | 63-72 RPS21 | NP_001015.1 | SEQ ID NO. 158 |
| 159. | GEGDFLAEGGGV | 23-34 FGA | NP_000499.1 | SEQ ID NO. 159 |
| 160. | DNFPQSL | 690-696 CACNA1C | NP_000710.3 | SEQ ID NO. 160 |
| 161. | GLTDVILYH | 269-277 SYNCRIP | NP_006363.3 | SEQ ID NO. 161 |
| 162. | AALVASGVALY | 247-257 P2RY11 | NP_002557.2 | SEQ ID NO. 162 |
| 163. | AEIRHVLVTL | 107-116 MYL6 | NP_066299.2 | SEQ ID NO. 163 |
| 164. | AEPEEVEVL | 10-18 PGR1 | NP_150638.1 | SEQ ID NO. 164 |
| 165. | AIIDHIFASK | 256-265 KIS | NP_787062 | SEQ ID NO. 165 |
| 166. | ALLDGSNVVFK | 48-58 HKE2 | NP_055075.1 | SEQ ID NO. 166 |
| 167. | AMLDTVVFK | 302-310 PSMD14 | NP_005796.1 | SEQ ID NO. 167 |

TABLE 1-continued

| | Sequence | Position/Gene symbol | Acc. No. | SEQ ID NO. |
|---|---|---|---|---|
| 168. | APARLFALL | 2-10<br>SDC4 | NP_002990.2 | SEQ ID NO. 168 |
| 169. | AVNAHSNILK | 248-257<br>IMMT | NP_006830 | SEQ ID NO. 169 |
| 170. | APRPGVLLL | 8-16<br>ELN | NP_000492 | SEQ ID NO. 170 |
| 171. | EAFPLRVID | 749-757<br>MAN2A2 | NP_006113.1 | SEQ ID NO. 171 |
| 172. | GVADKILKK | 211-219<br>NMI | NP_004679.1 | SEQ ID NO. 172 |
| 173. | AVFPKPFVEK | 189-198<br>KIAA0377 | NP_055474.2 | SEQ ID NO. 173 |
| 174. | VVYVGGILTK | 258-267<br>UGT8 | NP_003351.2 | SEQ ID NO. 174 |
| 175. | HLEDIVRQK | 1751-1759<br>TRIP12 | XP_376178.1 | SEQ ID NO. 175 |
| 176. | VTLTLVILSY | 207-216<br>LOC390323 | XP_372460.1 | SEQ ID NO. 176 |
| 177. | SLLSLVTGLK | reading frame +3<br>Symbol does not<br>exist; Gene type:<br>expressed sequence<br>tag | CD105815 | SEQ ID NO. 177 |
| 178. | QTYVGITEK | 687-695<br>U5-200KD | NP_054733.2 | SEQ ID NO. 178 |
| 179. | HEDKIRVVL | 210-218<br>EHD2 | NP_055416.2 | SEQ ID NO. 179 |
| 180. | QISIPFLLK | 208-216<br>C9orf88 | AAH01979 | SEQ ID NO. 180 |
| 181. | GLMGFIVYK | 39-37<br>C14orf2 | NP_004885.1 | SEQ ID NO. 181 |
| 182. | FADQEVRSL | 950-958<br>PIK3C2A | NP_002636.1 | SEQ ID NO. 182 |
| 183. | IVALILSTK | 147-155<br>ATP6V0C | NP_001685.1 | SEQ ID NO. 183 |
| 184. | GTYAPAEVPK | 22-31<br>AKR1C1 | NP_001344.2 | SEQ ID NO. 184 |
| 185. | GTMTGMLYK | 161-169<br>TIMM23 | NP_006318.1 | SEQ ID NO. 185 |
| 186. | SLAEILLKK | 439-447<br>IPO8 | NP_006381.1 | SEQ ID NO. 186 |
| 187. | KLTYIYIQK | Reading frame +1<br>Symbol does not<br>exist; Gene type:<br>expressed sequence<br>tag | AA295205 | SEQ ID NO. 187 |
| 188. | KLLNYAPLEK | 58-67<br>POLR2L | NP_055427 | SEQ ID NO. 188 |
| 189. | GTLPHPLQR | 182-190<br>SCNN1A | NP_001029.1 | SEQ ID NO. 189 |
| 190. | GLYEFFRAK | 680-688<br>CHERP | NP_006378.2 | SEQ ID NO. 190 |

TABLE 1-continued

| | Sequence | Position/ Gene symbol | Acc. No. | SEQ ID NO. |
|---|---|---|---|---|
| 191. | KEPEINTTL | 226-234 FLJ34588 | NP_689939.1 | SEQ ID NO. 191 |
| 192. | HASDRIIAL | 330-338 TKT | NP_001055.1 | SEQ ID NO. 192 |
| | | Sequences of RCC098 | | |
| 193. | RPTLWAAAL | 5-13 IGFBP3 | NP_000589.1 | SEQ ID NO. 193 |
| 194. | APSPRPLSL | 11-19 C19orf28 | NP_778148.1 | SEQ ID NO. 194 |
| 195. | ASDFITKMDY | 362-371 GSN | NP_000168.1 | SEQ ID NO. 195 |
| 196. | EERVINEEY | 13-21 RBBP4 | NP_005601.1 | SEQ ID NO. 196 |
| 197. | ATGSWDSFLK | 328-337 GNB1 | NP_002065.1 | SEQ ID NO. 197 |
| 198. | RMFDMGFEY | 411-419 DDX42 | NP_031398.2 | SEQ ID NO. 198 |
| 199. | APLLRWVL | 265-272 HMOX1 | NP_002124.1 | SEQ ID NO. 199 |
| 200. | ALRPSTSRSLY | 43-53 VIM | NP_003371.1 | SEQ ID NO. 200 |
| 201. | RQIPYTMMK | 225-233 SLC25A3 | NP_002626.1 | SEQ ID NO. 201 |
| 202. | AETHIVLLF | 267-275 DKFZpS64K142 | NP_115497.3 | SEQ ID NO. 202 |
| 203. | RVHAYIISY | 305-313 EHD2 | NP_055416.2 | SEQ ID NO. 203 |
| 204. | AVIVLVENFYK | 11-21 S100A16 | NP_525127.1 | SEQ ID NO. 204 |
| 205. | SEELLREHY | 61-69 NME3 | NP_002504.2 | SEQ ID NO. 205 |
| 206. | RADGNFLLY | 368-376 KIAA0930 | XP_047214.6 | SEQ ID NO. 206 |
| 207. | SEFTGVWKY | 83-91 PDCD6 | NP_037364.1 | SEQ ID NO. 207 |
| 208. | SIDRTVMYY | 389-397 SLC3A1 | NP_000332.1 | SEQ ID NO. 208 |
| 209. | ETDLLDIRSEY | 463-473 ANXA11 | NP_001148.1 | SEQ ID NO. 209 |
| 210. | ESYEALPQH | 397-405 DNMT1 | NP_001370.1 | SEQ ID NO. 210 |
| 211. | SEEEIREAF | 82-90 CALM2 | NP_001734.1 | SEQ ID NO. 211 |
| 212. | KVMQQNLVY | 329-337 CRTAP | NP_006362.1 | SEQ ID NO. 212 |
| 213. | DEKSIITY | 262-269 SPTBN1 | NP_003119.1 | SEQ ID NO. 213 |
| 214. | EEIEGFRY | 421-428 DDX56 | NP_061955.1 | SEQ ID NO. 214 |
| 215. | MENLFINRF | 186-194 ALOX5 | NP_000689.1 | SEQ ID NO. 215 |

TABLE 1-continued

| | Sequence | Position/Gene symbol | Acc. No. | SEQ ID NO. |
|---|---|---|---|---|
| 216. | MEKIWHHTF | 82-90 ACTB | NP_001092.1 | SEQ ID NO. 216 |
| 217. | MEHAMETMMF | 5-14 S100GA10 | NP_002957.1 | SEQ ID NO. 217 |
| 218. | EEIFNLKF | 353-542 GTF2I | NP_001509.2 | SEQ ID NO. 218 |
| 219. | LVLMVLYLI | 153-161 PIGM | NP_660150.1 | SEQ ID NO. 219 |
| 220. | EELQQKVSY | 285-293 STAT3 | NP_003141.2 | SEQ ID NO. 220 |
| 221. | LRVAPEEHPVL | 94-104 ACTB | NP_001092.1 | SEQ ID NO. 221 |
| 222. | DGHLFQVEY | 13-21 PSMA7 | NP_002783.1 | SEQ ID NO. 222 |
| 223. | LAELAHREY | 14-22 OGT | NP_003596.2 | SEQ ID NO. 223 |
| 224. | NEADVHGIYF | 651-660 CP | NP_000087.1 | SEQ ID NO. 224 |
| 225. | KVFQEPLFY | 114-122 CTSL | NP_001903.1 | SEQ ID NO. 225 |
| 226. | GVLAWVKEK | 171-179 NK4 | NP_004212.3 | SEQ ID NO. 226 |
| 227. | HEALLYYVL | 738-746 KIAA0746 | NP_056002.1 | SEQ ID NO. 227 |
| 228. | HEMIILKL | 3489-3496 KIAA1554 | XP_290768.3 | SEQ ID NO. 228 |
| 229. | IVPANFPSL | 443-451 C9orf3 | NP_116212.3 | SEQ ID NO. 229 |
| 230. | HLDLGILYY | 162-170 DPAGT1 | NP_001373.2 | SEQ ID NO. 230 |
| 231. | ITDSAGHILY | 76-85 TMP21 | NP_006818.2 | SEQ ID NO. 231 |
| 232. | HTDDPLTWDY | 267-276 HCA66 | NP_060898.1 | SEQ ID NO. 232 |
| 233. | IARNLTQQL | 313-321 ADFP | NP_001113.2 | SEQ ID NO. 233 |
| 234. | IDQTALAVY | 1087-1095 TPP2 | NP_003282.1 | SEQ ID NO. 234 |
| 235. | LEDVVIERY | 41-49 FKBP10 | NP_068758.2 | SEQ ID NO. 235 |
| 236. | QIASFILLR | 316-324 HIMAP4 | NP_060796.1 | SEQ ID NO. 236 |
| 237. | DEHYILTF | 550-557 OSBPL9 | NP_078862.2 | SEQ ID NO. 237 |
| 238. | DEIGLPKIFY | 124-133 IQGAP1 | NP_003861.1 | SEQ ID NO. 238 |
| 239. | DEIVRINGY | 132-140 USH1C | NP_005700.1 | SEQ ID NO. 239 |
| 240. | DEKLLYDTF | 112-120 SF3B4 | NP_005841.1 | SEQ ID NO. 240 |

TABLE 1-continued

| Sequence | Position/Gene symbol | Acc. No. | SEQ ID NO. |
|---|---|---|---|
| 241. RIIEETLALK | 9-18 ARPC2 | NP_005722.1 | SEQ ID NO. 241 |
| 242. GTDELRLLY | 107-115 FLJ12525 | NP_112483.1 | SEQ ID NO. 242 |
| 243. DELEIIEGMKF | 209-219 HSPD1 | NP_002147.2 | SEQ ID NO. 243 |
| 244. QVDPLSALKY | 649-658 MKLN1 | NP_037387.2 | SEQ ID NO. 244 |
| 245. DELHYLEVY | 72-80 VPS35 | NP_060676.2 | SEQ ID NO. 245 |
| 246. EEFELLGKAY | 81-90 EIF3S8 | NP_003743.1 | SEQ ID NO. 246 |
| 247. QLEDGRTLSDY | 49-59 UBB | NP_061828.1 | SEQ ID NO. 247 |
| 248. DEFLWREQF | 42-50 FBXW5 | NP_061871.1 | SEQ ID NO. 248 |
| 249. DEMLSRGF | 185-192 EIF4A1 | NP_001407.1 | SEQ ID NO. 249 |
| 250. DEPLLKHWEF | 196-205 HLA-DRA | NP_061984.1 | SEQ ID NO. 250 |
| 251. PSRDSLPLPV | 418-427 GPSM1 | NP_056412.2 | SEQ ID NO. 251 |
| 252. NLRETNLDSLP | 422-432 VIM | NP_003371.1 | SEQ ID NO. 252 |
| 253. DEVKFLTVL | 191-199 ANXA4 | NP_001144.1 | SEQ ID NO. 253 |
| 254. NEVEKTMEY | 440-448 RSHL2 | NP_114130.3 | SEQ ID NO. 254 |
| 255. DEVQVVRGHY | 53-62 RPL26 | NP_000978.1 | SEQ ID NO. 255 |
| 256. DEWLKPELF | 296-304 CGI-26 | NP_057038.1 | SEQ ID NO. 256 |
| 257. DEYSLVREL | 125-133 TLN1 | NP_006280.2 | SEQ ID NO. 257 |
| 258. NEFEATQKL | 343-351 NFIL3 | NP_005375.1 | SEQ ID NO. 258 |
| 259. DELQQPLEL | 704-712 STAT2 | NP_005410.1 | SEQ ID NO. 259 |
| 260. DVVMTQSPLSL | 20-30 IGKV@ | S40322 | SEQ ID NO. 260 |
| 261. SEREAIEVF | 358-366 GBP2 | NP_004111 | SEQ ID NO. 261 |
| 262. RYFYHQEEY | 21-29 HLA-DRB1 | CAA09468 | SEQ ID NO. 262 |
| 263. TSALPIIQK | 63-71 ADFP | NP_001113.2 | SEQ ID NO. 263 |
| 264. RVQEAVESMVK | 8-18 FLJ14668 | AAH14975 | SEQ ID NO. 264 |
| 265. TVMELVKIIYK | 237-247 LACTB2 | NP_057111.1 | SEQ ID NO. 265 |

TABLE 1-continued

| | Sequence | Position/Gene symbol | Acc. No. | SEQ ID NO. |
|---|---|---|---|---|
| 266. | RLLQKVLAY | 103-111 FLJ10211 | BAA91493 | SEQ ID NO. 266 |
| 267. | RIHFPLATY | 264-272 K-ALPHA-1 | NP_006073 | SEQ ID NO. 267 |
| 268. | VGGLKNTLVHRL | 279-290 FLJ31579 | NP_695000.1 | SEQ ID NO. 268 |
| 269. | QAQADSLTVY | 679-688 PCDHB5 | AAP97251.1 | SEQ ID NO. 269 |
| 270. | VLDPYLLKY | 34-42 MRPS17 | NP_057053.1 | SEQ ID NO. 270 |
| 271. | IFSPPFPLFY | 83-92 FKSG63 | AAK08108.1 | SEQ ID NO. 271 |
| 272. | TELLLKEGF | 260-268 SND1 | NP_055205.1 | SEQ ID NO. 272 |
| 273. | GLFEVGAGWIGK | 235-246 HSD17B4 | NP_000405.1 | SEQ ID NO. 273 |
| 274. | YEYKFGFEL | 97-105 TXNIP | NP_006463.2 | SEQ ID NO. 274 |
| 275. | WPLWRLVSL | 2-10 BGN | NP_001702.1 | SEQ ID NO. 275 |
| 276. | YIDEQFERY | 121-129 NEDD5 | NP_004395.1 | SEQ ID NO. 276 |
| 277. | YLDEKLALLNA | 897-907 BAIAP3 | NP_003924.2 | SEQ ID NO. 277 |
| 278. | DEHLITFF | 1248-1255 US-200KD | NP_054733.2 | SEQ ID NO. 278 |
| 279. | DDFHIYVY | 234-241 SPIN | NP_006708 | SEQ ID NO. 279 |
| 280. | APRTVLLLL | 5-13 HLA-A, -B or -C | AAL30417.1 | SEQ ID NO. 280 |
| 281. | APRTVALTALL | 9-19 HLA-DPB1 | NP_002112 | SEQ ID NO. 281 |
| 282. | FTDVNSILRY | 58-67 EPRS | AAH58921 | SEQ ID NO. 282 |
| 283. | YSEEECRQY | 61-69 GNAI2 | NP_002061.1 | SEQ ID NO. 283 |
| 284. | YSEKIVDMY | 134-142 MYH11 | NP_002465.1 | SEQ ID NO. 284 |
| 285. | YTDLLRLFEY | 68-77 PPP1CB | NP_002700.1 | SEQ ID NO. 285 |
| 286. | YVDPQFLTY | 341-349 PJA1 | NP_071763.2 | SEQ ID NO. 286 |
| 287. | HERTFLLEY | 96-104 SNX6 | NP_067072.2 | SEQ ID NO. 287 |
| 288. | SSVPGVRLLQDSVDFSL | 72-88 VIM | NP_003371.1 | SEQ ID NO. 288 |
| 289. | SLLTSSKGQLQK | 369-380 ADFP | NP_001113.2 | SEQ ID NO. 289 |
| 290. | SPRENILVSL | 281-290 SCD | NP_005054.2 | SEQ ID NO. 290 |

TABLE 1-continued

| Sequence | Position/Gene symbol | Acc. No. | SEQ ID NO. |
|---|---|---|---|
| 291. DEVDIKSRAAY | 18-28<br>FTO | XP_051200.4 | SEQ ID NO. 291 |
| 292. TSPSQSLFY | 154-162<br>SLC11A1 | AAH41787.1 | SEQ ID NO. 292 |
| 293. YTETEPYHNY | 392-401<br>LOC124245 | NP_653205.2 | SEQ ID NO. 293 |
| 294. SSVPGVRLLQDSVDF | 72-86<br>VIM | NP_003371.1 | SEQ ID NO. 294 |
| 295. VALISPKDI | Reading frame -1<br>Symbol does not<br>exist; Gene type:<br>expressed sequence<br>tag | AC079587.4 | SEQ ID NO. 295 |
| 296. STDKAEYTFY | 332-341<br>RBPSUH | NP_005340.2 | SEQ ID NO. 296 |
| 297. VTEIFRQAF | 250-258<br>GARNL1 | BAA74907.1 | SEQ ID NO. 297 |
| 298. SVLSPLLNK | 380-388<br>EPS8 | NP_004438.2 | SEQ ID NO. 298 |
| Sequences of RCC100 | | | |
| 299. RAFSSLGLLK | 615-624<br>UMOD | NP_003352.1 | SEQ ID NO. 299 |
| 300. FSKLRPLISK | 243-252<br>PGBD3 | NP_736609.1 | SEQ ID NO. 300 |
| 301. RTFTWLVGK | 353-361<br>MYO1C | NP_203693.2 | SEQ ID NO. 301 |
| 302. KVANIILSY | 1273-1281<br>FLJ21439 | NP_079413.2 | SEQ ID NO. 302 |
| 303. TMLARLASA | 21-29<br>CSPG4 | NP_001888.1 | SEQ ID NO. 303 |
| 304. HELPLPHSV | 39-47<br>EPAS1 | NP_001421.2 | SEQ ID NO. 304 |
| Sequences of RCC103 | | | |
| 305. AVQRTLLEK | 177-185<br>CD99 | NP_002405.1 | SEQ ID NO. 305 |
| 306. ETRPAGDGTFQKW | 256-268<br>HLA-A | NP_002107 | SEQ ID NO. 306 |
| 307. AVLSILPAIFQK | 392-403<br>KIAA0033 | XP_084530.5 | SEQ ID NO. 307 |
| 308. EIAGHIMEF | 848-856<br>PUM1 | NP_055491.1 | SEQ ID NO. 308 |
| 309. ELIRTIMGW | 131-139<br>BAX | NP_004315.1 | SEQ ID NO. 309 |
| 310. EVFPLKVFGY | 45-54<br>ZNF258 | AAH29439 | SEQ ID NO. 310 |
| 311. ATPTSPIRVK | 856-865<br>FLNA | NP_001447.1 | SEQ ID NO. 311 |
| 312. AVLYQPLFDK | 107-116<br>NAP1L1 | NP_004528.1 | SEQ ID NO. 312 |
| 313. EVVDFIQSKI | 451-460<br>PPM1G | NP_817092 | SEQ ID NO. 313 |

TABLE 1-continued

| Sequence | Position/Gene symbol | Acc. No. | SEQ ID NO. |
|---|---|---|---|
| 314. AVQEFGLARFK | 142-152 PX19 | NP_037369.1 | SEQ ID NO. 314 |
| 315. EAIQDLWQW | 282-290 NPM1 | NP_002511.1 | SEQ ID NO. 315 |
| 316. GVIRSLMAF | 60-68 SF3B3 | NP_036558.2 | SEQ ID NO. 316 |
| 317. HIISGTCASW | 241-250 TXNIP | NP_006463.2 | SEQ ID NO. 317 |
| 318. GVIDVITKTW | 261-270 MFTC | NP_110407.2 | SEQ ID NO. 318 |
| 319. GVIDLIFEK | 600-608 EIF4G1 | NP_004944.2 | SEQ ID NO. 319 |
| 320. GVCHIFASF | 29-37 RPS14 | NP_005608.1 | SEQ ID NO. 320 |
| 321. GTYVSSVPR | 242-250 HLA-DOA | NP_002110.1 | SEQ ID NO. 321 |
| 322. GTAGLLEQWLK | 329-339 DC12 | NP_064572.1 | SEQ ID NO. 322 |
| 323. HVITGLLEHY | 133-142 SCRN2 | NP_612364.1 | SEQ ID NO. 323 |
| 324. GTADELVLHSW | 176-186 LYPLAL1 | NP_620149.1 | SEQ ID NO. 324 |
| 325. EIKEVILEF | 873-881 VPS13C | NP_060154 | SEQ ID NO. 325 |
| 326. EEASLLHQF | 741-749 SPTBN1 | NP_003119.1 | SEQ ID NO. 326 |
| 327. KLFIGGLSF | 15-23 HNRPA1 | NP_002127.1 | SEQ ID NO. 327 |
| 328. DVVPAVRKW | 134-142 MASA | NP_067027.1 | SEQ ID NO. 328 |
| 329. DVTGVVRQW | 200-208 TGFB1 | NP_000651.1 | SEQ ID NO. 329 |
| 330. DVKDYIQEY | 2500-2508 KIAA1554 | XP_290768.3 | SEQ ID NO. 330 |
| 331. DVIDNDSWRLW | 207-217 PAICS | NP_006443.1 | SEQ ID NO. 331 |
| 332. DVFSSKGMTRW | 90-100 RASSF6 | NP_803876.1 | SEQ ID NO. 332 |
| 333. DTVKKIESF | 3197-3205 RANBP2 | NP_006258.2 | SEQ ID NO. 333 |
| 334. DLPSNHVIDRW | 211-221 SKB1 | NP_006100.2 | SEQ ID NO. 334 |
| 335. DLIGHIVEF | 726-734 PUM2 | NP_056132.1 | SEQ ID NO. 335 |
| 336. DKESQLEAY | 106-114 LOC284680 | NP_872387.1 | SEQ ID NO. 336 |
| 337. EVIKLKGYTSW | 240-250 LDHA | NP_005557.1 | SEQ ID NO. 337 |
| 338. GSSDVIIHR | 519-527 KIAA1542 | XP_290536.2 | SEQ ID NO. 338 |
| 339. GTLDYILQR | 158-166 FTO | XP_051200.4 | SEQ ID NO. 339 |

TABLE 1-continued

| | Sequence | Position/ Gene symbol | Acc. No. | SEQ ID NO. |
|---|---|---|---|---|
| 340. | EVDKRVHMTW | 326-335 PSMD13 | NP_002808.2 | SEQ ID NO. 340 |
| 341. | SVPYFLFQHW | 197-206 SOAT1 | NP_003092.3 | SEQ ID NO. 341 |
| 342. | SVEEISTLVQK | 93-103 MRPL43 | NP_115488.2 | SEQ ID NO. 342 |
| 343. | STFQQMWISK | 352-361 ACTA2 | NP_001604.1 | SEQ ID NO. 343 |
| 344. | TTIPHALLTW | 1533-1542 BIG1 | NP_006412.1 | SEQ ID NO. 344 |
| 345. | SAFLLLGLFK | 419-428 TAPBP | NP_003181.3 | SEQ ID NO. 345 |
| 346. | NIGDEALIGRW | 637-647 MAGED4 | NP_110428.2 | SEQ ID NO. 346 |
| 347. | TVAFVPISGW | 187-196 EEF1A1 | NP_001393.1 | SEQ ID NO. 347 |
| 348. | ETVNLRSLGF | 1930-1939 AIM1 | XP_166300.3 | SEQ ID NO. 348 |
| 349. | MPKFSMPGF | 72-80 AHNAK | BAC87652.1 | SEQ ID NO. 349 |
| 350. | EVMEIMSRF | 98-106 POLH | NP_006493.1 | SEQ ID NO. 350 |
| 351. | EVMDVFLRF | 695-703 CSG1cA-T | XP_376724.1 | SEQ ID NO. 351 |
| 352. | RLQEALNLF | 265-273 GNAS | NP_000507.1 | SEQ ID NO. 352 |
| 353. | ETIDWKVFESW | 174-184 CD74 | NP_004346.1 | SEQ ID NO. 353 |
| 354. | ELMEHGVVSW | 39-48 ELMO3 | NP_078988.1 | SEQ ID NO. 354 |
| 355. | ASVAWAVLK | 2-10 CASPR3 | NP_387504.1 | SEQ ID NO. 355 |
| 356. | SVSPVVHVR | 73-81 LOC92906 | NP_612403.2 | SEQ ID NO. 356 |
| 357. | HVVDRDTEAW | 27-36 FLJ35220 | NP_775898.2 | SEQ ID NO. 357 |
| 358. | ETITGLRVW | 6493-6501 NEB | NP_004534.1 | SEQ ID NO. 358 |
| 359. | RQLEDILSTY | 77-86 DKFZp451J0118 | NP_787048.1 | SEQ ID NO. 359 |
| 360. | AIAQAESLRYK | 98-108 RPS3 | NP_000996.2 | SEQ ID NO. 360 |
| 361. | GVLQLGNIVFK | 345-355 MYH9 | NP_002464.1 | SEQ ID NO. 361 |
| 362. | EVINALKQTW | 489-498 LIM | NP_006448.1 | SEQ ID NO. 362 |
| 363. | STAAFFLLR | 407-415 SLC37A4 | NP_001458.1 | SEQ ID NO. 363 |
| 364. | DIYNFPIHAF | 177-186 LOC84549 | NP_115898.2 | SEQ ID NO. 364 |

TABLE 1-continued

| Sequence | Position/Gene symbol | Acc. No. | SEQ ID NO. |
|---|---|---|---|
| 365. TVVERMLSNW | 1398-1407 PLXNB2 | BAA21571.1 | SEQ ID NO. 365 |
| 366. TKPWFASQIPF | 210-220 LOC345778 | XP_293971.3 | SEQ ID NO. 366 |
| Sequences of RCC112 | | | |
| 367. GRVDFAYKF | 111-119 PHC2 | NP_004418.2 | SEQ ID NO. 367 |
| 368. GRDLTDYLM | 182-190 ACTG1 | NP_001605.1 | SEQ ID NO. 368 |
| 369. GRISITGVGF | 101-110 MGC21644 | NP_612501.3 | SEQ ID NO. 369 |
| 370. GRIVTLISF | 262-270 MCL1 | NP_068779.1 | SEQ ID NO. 370 |
| 371. GRLDLQYAKL | 622-631 PLEC1 | NP_000436.1 | SEQ ID NO. 371 |
| 372. GRTNLIVNY | 18-26 ELAVL1 | NP_001410.2 | SEQ ID NO. 372 |
| 373. RYFDTAVSR | 5-13 HLA-A, -B or -C | AAC17722 | SEQ ID NO. 373 |
| 374. GRMVQVHEL | 170-178 SEC23A | NP_006355.2 | SEQ ID NO. 374 |
| 375. FLDASGAKLDY | 53-63 BZW1 | NP_055485.2 | SEQ ID NO. 375 |
| 376. ATDYHVRVY | 348-356 FAD104 | NP_073600.2 | SEQ ID NO. 376 |
| 377. ARLPWAGQL | 624-632 PBXIP1 | NP_065385.2 | SEQ ID NO. 377 |
| 378. YGMPRQIL | 192-199 TAGLN2 | NP_003555.1 | SEQ ID NO. 378 |
| 379. GRLLVATTF | 385-393 IARS | NP_002152.1 | SEQ ID NO. 379 |
| 380. AGGDWFTSR | 136-144 PPP2R1A | NP_055040.2 | SEQ ID NO. 380 |
| 381. GRAPISNPGM | 179-188 RPA2 | NP_002937 | SEQ ID NO. 381 |
| 382. GRMENLASYR | 308-317 PPP1R3C | NP_005389 | SEQ ID NO. 382 |
| 383. VLPKSRVEL | 89-97 HLA-DOA | BAA81787 | SEQ ID NO. 383 |
| 384. DAKIRIFDL | 28-36 RPL10 | NP_006004.1 | SEQ ID NO. 384 |
| 385. GRAMVARLGL | 2-11 CD24 | NP_037362.1 | SEQ ID NO. 385 |
| 386. FIDASRLVY | 612-620 CTNNA1 | NP_001894.1 | SEQ ID NO. 386 |
| 387. DPMKARVVL | 21-29 SRP9 | NP_003124.1 | SEQ ID NO. 387 |
| 388. FRFDPQFAL | 77-85 HLA-DQA1 | XP_371812 | SEQ ID NO. 388 |
| 389. DTDHYFLRY | 165-173 PIGT | NP_057021.2 | SEQ ID NO. 389 |

TABLE 1-continued

| Sequence | Position/Gene symbol | Acc. No. | SEQ ID NO. |
|---|---|---|---|
| 390. ELLIRKLPF | 60-68 HIST3H3 | NP_003484.1 | SEQ ID NO. 390 |
| 391. EAFVRHIL | 142-149 MYL6 | NP_066299.2 | SEQ ID NO. 391 |
| 392. RYFDTAMSR | 5-13 HLA-A,-B or -C | AAB48498.1 | SEQ ID NO. 392 |
| 393. GRVFIISKY | 416-424 FLJ31657 | NP_689971 | SEQ ID NO. 393 |
| 394. TFRPAAMLVER | 154-164 LAMB2 | NP_002283.2 | SEQ ID NO. 394 |
| 395. YLLEKSRAI | 257-265 MYH9 | NP_002464.1 | SEQ ID NO. 395 |
| 396. LSDLGKLSY | 353-361 MYST1 | NP_115564.1 | SEQ ID NO. 396 |
| 397. VTDSIRDEY | 258-266 DNM1L | NP_005681.1 | SEQ ID NO. 397 |
| 398. LTDRELEEY | 567-575 ADD1 | NP_001110.2 | SEQ ID NO. 398 |
| 399. LTDRGVMSY | 252-260 IRF3 | NP_001562.1 | SEQ ID NO. 399 |
| 400. KGLSVFLNR | 527-535 GPNMB | NP_002501.1 | SEQ ID NO. 400 |
| 401. VTDNRAFGY | 128-136 DAB2 | NP_001334.1 | SEQ ID NO. 401 |
| 402. STDVSDLLHQY | 257-267 PSMB8 | NP_004150.1 | SEQ ID NO. 402 |
| 403. RSLPFFSAR | 135-143 TRAPPC1 | NP_067033.1 | SEQ ID NO. 403 |
| 404. YRFMGTEAY | 378-386 SLC3A1 | NP_000332.1 | SEQ ID NO. 404 |
| 405. MPLLRQEEL | 394-402 EHD2 | NP_055416.2 | SEQ ID NO. 405 |
| 406. VTEIDQDKY | 2380-2388 FLNA | NP_001447.1 | SEQ ID NO. 406 |
| 407. MRHLGAFLF | 1-9 TCN2 | NP_000346.2 | SEQ ID NO. 407 |
| 408. TTEESLRNYY | 20-29 HNRPA2B1 | NP_002128.1 | SEQ ID NO. 408 |
| 409. MRTSYLLLF | 1-9 DEFB1 | NP_005209.1 | SEQ ID NO. 409 |
| 410. TVDQVKDLY | 882-890 CP | NP_000087.1 | SEQ ID NO. 410 |
| 411. MRYVASYLL | 1-9 RPLP2 | NP_000995.1 | SEQ ID NO. 411 |
| 412. VGLIRNLAL | 511-519 CTNNB1 | NP_001895.1 | SEQ ID NO. 412 |
| 413. GRLDAVLQR | 317-325 PML | NP_002666.1 | SEQ ID NO. 413 |
| 414. LLDQGQLNKY | 421-430 CLTC | NP_004850.1 | SEQ ID NO. 414 |

TABLE 1-continued

| | Sequence | Position/ Gene symbol | Acc. No. | SEQ ID NO. |
|---|---|---|---|---|
| 415. | NRFAGFGIGL | 98-107 LOC91137 | NP_620128.1 | SEQ ID NO. 415 |
| 416. | KRLGTLVVTY | 305-314 GBP4 | NP_443173.2 | SEQ ID NO. 416 |
| 417. | KRGDVIYIL | 319-327 SCAP2 | NP_003921.2 | SEQ ID NO. 417 |
| 418. | SRFDIPLGL | 1103-1111 PCF11 | NP_056969.2 | SEQ ID NO. 418 |
| 419. | STDPSVLGKY | 101-110 HES1 | NP_005515.1 | SEQ ID NO. 419 |
| 420. | SRFLKSDLF | 130-138 RGS10 | NP_002916.1 | SEQ ID NO. 420 |
| 421. | VQKPSYYVR | 211-219 ADFP | NP_001113.2 | SEQ ID NO. 421 |
| 422. | SRISLPLPNF | 409-418 VIM | NP_003371.1 | SEQ ID NO. 422 |
| 423. | LRSGLPLLL | 231-239 MADHIP | NP_004790.1 | SEQ ID NO. 423 |
| 424. | SFKDYIQER | 330-338 ETS2 | NP_005230.1 | SEQ ID NO. 424 |
| 425. | HTQGPVDGSLY | 104-114 TENS1 | NP_073585.6 | SEQ ID NO. 425 |
| 426. | STDKFKTDFY | 271-280 COPS6 | NP_006824.2 | SEQ ID NO. 426 |
| | Sequences of RCC115 | | | |
| 427. | GSHSMRYFF | 25-33 HLA-A | NP_002107 | SEQ ID NO. 427 |
| 428. | GSHSMRYFFT | 25-34 HLA-A | NP_002107 | SEQ ID NO. 428 |
| 429. | GSHSMRYFH | 25-33 HLA-B | I37515 | SEQ ID NO. 429 |
| 430. | AAILGMHNL | 135-143 TMOD3 | NP_055362.1 | SEQ ID NO. 430 |
| 431. | KLDPTKTTL | 275-283 NDRG1 | NP_006087.2 | SEQ ID NO. 431 |
| 432. | FVHDLVLYL | 783-791 CLTCL1 | NP_001826.1 | SEQ ID NO. 432 |
| 433. | FVHDLVL | 783-789 CLTCL1 | NP_001826.1 | SEQ ID NO. 433 |
| 434. | VLIPKLPQL | 134-142 ORMDL3 | NP_644809.1 | SEQ ID NO. 434 |
| 435. | NEITIPVTF | 177-185 HSPB1 | NP_001531.1 | SEQ ID NO. 435 |
| 436. | YLADFLLTK | 255-263 SLC17A3 | NP_006623.1 | SEQ ID NO. 436 |
| 437. | YLIPLLERL | 139-147 DDX6 | NP_004388.1 | SEQ ID NO. 437 |
| 438. | NEVVTREY | 18-25 RPL31 | NP_000984.1 | SEQ ID NO. 438 |
| 439. | DEFKIGELF | 145-153 PRKDC | NP_008835 | SEQ ID NO. 439 |

TABLE 1-continued

| Sequence | Position/Gene symbol | Acc. No. | SEQ ID NO. |
|---|---|---|---|
| 440. IQRTPKIQVYS | 21-31 B2M | NP_004039.1 | SEQ ID NO. 440 |
| 441. LTGPVMPVR | 150-158 RPL13 | NP_000968.2 | SEQ ID NO. 441 |
| 442. AVAIKAMAK | 146-154 EIF5A | NP_001961.1 | SEQ ID NO. 442 |
| 443. FVQMMTAK | 142-149 CALM1 | NP_008819.1 | SEQ ID NO. 443 |
| 444. ATDPNILGR | 4111-4119 PRKDC | NP_008835.5 | SEQ ID NO. 444 |
| 445. LLLLSIVIL | 212-220 EDG1 | NP_001391.2 | SEQ ID NO. 445 |
| 446. KLPNFGFVVF | 376-385 G3BP | NP_005745.1 | SEQ ID NO. 446 |
| 447. KLSEIDVAL | 174-182 EFHD1 | NP_079478.1 | SEQ ID NO. 447 |
| 448. LAALPHSCL | 5-13 RGS5 | NP_003608.1 | SEQ ID NO. 448 |
| 449. YSIITPNILRL | 26-36 C3 | NP_000055.1 | SEQ ID NO. 449 |
| 450. ALPSRILLWK | 2-11 MGC3047 | NP_115724.1 | SEQ ID NO. 450 |
| 451. VKGFYPSDIAVE | 247-258 IGHG2 | AAB59393.1 | SEQ ID NO. 451 |
| 452. FLLDLSRSV | 92-100 GPR31 | NP_005290.1 | SEQ ID NO. 452 |
| 453. IIYKGGTSR | 545-553 GSN | NP_000168.1 | SEQ ID NO. 453 |
| 454. IVADHYASY | 3-11 MHC class II | AAC41957 | SEQ ID NO. 454 |
| 455. EVGGEALGRLL | 23-33 HBB | NP_000509.1 | SEQ ID NO. 455 |
| 456. RTGPPMGSRF | 175-184 WBSCR1 | NP_071496.1 | SEQ ID NO. 456 |
| 457. RQIQESVTF | 1305-1313 ANK2 | NP_001139.2 | SEQ ID NO. 457 |
| 458. RVAPEEHPV | 95-103 ACTB | NP_001092.1 | SEQ ID NO. 458 |
| 459. TLADLLALR | 1433-1441 DNAH11 | NP_003768.1 | SEQ ID NO. 459 |
| 460. RVAPEEHPVLLT | 95-106 ACTB | NP_001092.1 | SEQ ID NO. 460 |
| 461. TLADIIARL | 1487-1495 KIAA1305 | XP_370756.2 | SEQ ID NO. 461 |
| 462. RWEDGSPLNF | 142-151 KLRG1 | NP_005801.2 | SEQ ID NO. 462 |
| 463. YEVSQLKD | 468-475 CNDP2 | NP_060705.1 | SEQ ID NO. 463 |
| 464. YRDIPELQGF | 663-672 AACS | NP_076417 | SEQ ID NO. 464 |

TABLE 1-continued

| Sequence | Position/Gene symbol | Acc. No. | SEQ ID NO. |
|---|---|---|---|
| 465. YVDGTQFVRF | 51-60 HLA-A, -B or -C | BAA04965 | SEQ ID NO. 465 |
| 466. SLLDEFYKL | 184-192 M11S1 | NP_005889.3 | SEQ ID NO. 466 |
| 467. HGIDPTGTY | 28-36 TUBB5 | NP_006078.2 | SEQ ID NO. 467 |
| 468. SLDKFLASVSTVL | 125-137 HBA1 | NP_000549.1 | SEQ ID NO. 468 |
| 469. SIGERDLIFH | 289-298 TIMELESS | NP_003911.1 | SEQ ID NO. 469 |
| 470. SITSVFITK | 1788-1796 TRRAP | NP_003487.1 | SEQ ID NO. 470 |
| 471. FGEHLLESDLF | 28-38 CRYAB | NP_001876.1 | SEQ ID NO. 471 |
| 472. FLDPIKAYL | 76-84 GPR116 | NP_056049.3 | SEQ ID NO. 472 |
| 473. FLADPSAFVAA | 268-278 RPLP0 | NP_000993.1 | SEQ ID NO. 473 |
| 474. ITAPPSRVL | 20-28 SCD | NP_005054.2 | SEQ ID NO. 474 |
| 475. VLDELKNMKC | 170-179 CYFIP2 | NP_055191.1 | SEQ ID NO. 475 |
| 476. LLGPRLVLA | 23-31 TMP21 | NP_006818.2 | SEQ ID NO. 476 |
| 477. IIMPHNIYL | 251-259 SLC11A1 | NP_000569.2 | SEQ ID NO. 477 |
| 478. LVRMVLNG | 144-151 MYL6 | NP_034990 | SEQ ID NO. 478 |
| 479. RLYGPSSVSF | 133-142 SERPINH1 | NP_001226.2 | SEQ ID NO. 479 |
| 480. FEAPIKLVF | 236-244 HM13 | NP_110416.1 | SEQ ID NO. 480 |
| 481. IQPGAVKVY | 1472-1480 C3 | NP_000055.1 | SEQ ID NO. 481 |
| 482. VLAEVPTQL | 501-509 CPNE1 | NP_003906.1 | SEQ ID NO. 482 |
| 483. IMRAGMSSL | 521-529 CCT6A | NP_001753.1 | SEQ ID NO. 483 |
| 484. VEFSSGLKGMSL | 96-107 ATP5A1 | NP_004037.1 | SEQ ID NO. 484 |
| 485. ILNPDNSFEIL | 241-251 CANX | NP_001737.1 | SEQ ID NO. 485 |
| 486. VALEFALHL | 344-352 CABLES1 | NP_612384.1 | SEQ ID NO. 486 |
| 487. TVAVPLVGK | 22-30 MGC3067 | NP_077271.1 | SEQ ID NO. 487 |
| 488. TLSDLRVYL | 121-129 C20orf139 | NP_542763.1 | SEQ ID NO. 488 |
| 489. TLIDIMTRF | 35-43 HK1 | NP_000179.1 | SEQ ID NO. 489 |

TABLE 1-continued

| Sequence | Position/Gene symbol | Acc. No. | SEQ ID NO. |
|---|---|---|---|
| Sequences of RCC116 | | | |
| 490. HDFPRALIF | 64-72 CG018 | AAH22188 | SEQ ID NO. 490 |
| 491. GSHSMRYF | 25-32 HLA-A, -B or -C | BAA04965 | SEQ ID NO. 491 |
| 492. SLMDHTIPEV | 289-298 SDCBP | NP_005616.1 | SEQ ID NO. 492 |
| 493. SGVHTFPAVLQ | 155-165 Ig heavy chain | AAO22172 | SEQ ID NO. 493 |
| 494. FLVTVIHTL | 1065-1073 PLXNC1 | NP_005752.1 | SEQ ID NO. 494 |
| 495. TDGKVFQF | 24-31 RPL24 | NP_000977.1 | SEQ ID NO. 495 |
| 496. YDLLRNTNF | 246-254 DYRK1A | NP_001387.2 | SEQ ID NO. 496 |
| 497. ILYPKTLFL | 138-146 PPP3CA | NP_000935.1 | SEQ ID NO. 497 |
| 498. MRYVASYL | 1-8 RPLP2 | NP_000995.1 | SEQ ID NO. 498 |
| 499. FIWENIHTL | 3725-3733 BPAG1 | NP_056363.2 | SEQ ID NO. 499 |
| 500. RELPAWVSF | 125-133 MBC2 | NP_056107.1 | SEQ ID NO. 500 |
| 501. QDLNRIFPL | 81-89 PRG1 | NP_002718.2 | SEQ ID NO. 501 |
| 502. RDSIVAEL | 97-104 COPE | NP_009194.2 | SEQ ID NO. 502 |
| 503. ADVLKVEVF | 130-138 ITGB4BP | NP_002203.1 | SEQ ID NO. 503 |
| 504. YDSIIYRM | 335-342 ATP6AP2 | NP_005756.2 | SEQ ID NO. 504 |
| 505. AMNPVEHPF | 203-211 RPL8 | NP_000964.1 | SEQ ID NO. 505 |
| 506. SELIRNVTL | 126-134 U5-116KD | NP_004238.2 | SEQ ID NO. 506 |
| 507. QDVARVLGF | 117-125 PNMA1 | NP_006020.3 | SEQ ID NO. 507 |
| 508. SDHIHIIAL | 215-223 OTUB1 | NP_060140.1 | SEQ ID NO. 508 |
| 509. ADSLRLQQL | 781-789 SPTAN1 | NP_003118.1 | SEQ ID NO. 509 |
| 510. LLDIRSEY | 466-473 ANXA11 | NP_001148.1 | SEQ ID NO. 510 |
| 511. VLFGLLREV | 663-671 DHX38 | NP_054722.2 | SEQ ID NO. 511 |
| 512. VAVGRALYY | 510-518 DDB1 | NP_001914.2 | SEQ ID NO. 512 |
| 513. MRFLAATFL | 1-9 NPC2 | NP_006423.1 | SEQ ID NO. 513 |
| 514. YTDPEVFKY | 398-406 PTGIS | NP_000952.1 | SEQ ID NO. 514 |

TABLE 1-continued

| | Sequence | Position/Gene symbol | Acc. No. | SEQ ID NO. |
|---|---|---|---|---|
| 515. | HDFLKYDFF | 232-240 SURF4 | NP_149351.1 | SEQ ID NO. 515 |
| 516. | AIDQLHLEY | 525-533 ACTN4 | NP_004915.2 | SEQ ID NO. 516 |
| 517. | SDLERVTSL | 316-324 FLJ21616 | NP_078843.2 | SEQ ID NO. 517 |
| 518. | TLLPLRVFL | 128-136 FLJ90013 | NP_699196.1 | SEQ ID NO. 518 |
| 519. | YSIITPNILR | 26-35 C3 | NP_000055.1 | SEQ ID NO. 519 |
| 520. | FELQRNFQL | 19-27 ING4 | NP_057246.2 | SEQ ID NO. 520 |
| 521. | LDLQRNYIF | 186-194 UNQ3030 | NP_940967.1 | SEQ ID NO. 521 |
| 522. | RRLDPIPQL | 56-64 MGC8721 | NP_057211.4 | SEQ ID NO. 522 |
| 523. | SLPIKESEIIDF | 85-96 RPS2 | NP_002943.2 | SEQ ID NO. 523 |
| 524. | TELLRYYML | 292-300 SNX5 | NP_055241.1 | SEQ ID NO. 524 |
| 525. | FIYHGEVPQA | 254-263 MHC2TA | NP_000237.1 | SEQ ID NO. 525 |
| 526. | AEMLRSISF | 217-225 CSTF1 | NP_001315.1 | SEQ ID NO. 526 |
| 527. | RLQEDPPVGV | 15-24 UBE2B | NP_003328.1 | SEQ ID NO. 527 |
| 528. | AELERAAAL | 465-473 FLJ35453 | NP_689813.1 | SEQ ID NO. 528 |
| 529. | YTDKIDRY | 107-114 TM4SF7 | NP_003262.1 | SEQ ID NO. 529 |
| 530. | FLLPDVIRI | 329-337 TBC1D13 | NP_060671.2 | SEQ ID NO. 530 |
| 531. | VELPHINLL | 169-177 FLJ10349 | NP_060536.2 | SEQ ID NO. 531 |
| 532. | VMLDVPIRL | 725-733 RASAL2 | NP_004832.1 | SEQ ID NO. 532 |
| 533. | SLLENLEKI | 209-216 HNRPC | NP_112604.1 | SEQ ID NO. 533 |
| 534. | YADPVNAHY | 226-234 ROD1 | NP_005147.3 | SEQ ID NO. 534 |
| 535. | AELLRGLSL | 165-173 FBXL5 | NP_036293.1 | SEQ ID NO. 535 |
| 536. | TTEVHPELY | 51-59 SDBCAG84 | NP_057050.1 | SEQ ID NO. 536 |
| 537. | RETNLDSLP | 424-432 VIM | NP_003371.1 | SEQ ID NO. 537 |
| 538. | ELEDSTLRY | 543-551 PLEC1 | NP_000436.1 | SEQ ID NO. 538 |
| | | Sequences of RCC130 | | |
| 539. | FLDIYIFL | 84-91 LOC390875 | XP_372703.1 | SEQ ID NO. 539 |

TABLE 1-continued

| Sequence | Position/Gene symbol | Acc. No. | SEQ ID NO. |
|---|---|---|---|
| 540. TYTDRVFFL | 1282-1290 PLXNB2 | BAA21S71.1 | SEQ ID NO. 540 |
| 541. SPHLANYFYF | 147-156 Symbol does not exist; Gene type: unnamed protein product | BAC87422 | SEQ ID NO. 541 |
| 542. SPRLPVGGF | 1921-1929 TRIP12 | XP_376178.1 | SEQ ID NO. 542 |
| 543. KLLDKVQAYS | 9-18 GJA1 | NP_000156.1 | SEQ ID NO. 543 |
| 544. AYQHLFYLL | 955-963 IQGAP3 | NP_839943.2 | SEQ ID NO. 544 |
| 545. KYILLMDIIA | 148-157 TBX3 | NP_005987.2 | SEQ ID NO. 545 |
| 546. RYSSMAASF | 82-90 MAP17 | NP_005755.1 | SEQ ID NO. 546 |
| 547. SPRAAEPVQL | 397-406 CA9 | NP_001207.1 | SEQ ID NO. 547 |
| 548. IYTSSVNRL | 535-543 COPB2 | NP_004757.1 | SEQ ID NO. 548 |
| 549. LYPQFMFHL | 576-584 SEC23A | NP_006355.2 | SEQ ID NO. 549 |
| 550. RYIPTAAAF | 415-423 SEC61A1 | NP_037468.1 | SEQ ID NO. 550 |
| 551. EYIVKKIPV | 237-245 EIF2S3 | NP_001406.1 | SEQ ID NO. 551 |
| 552. SRVEAVYVL | 13-21 PADI2 | NP_031391.1 | SEQ ID NO. 552 |
| 553. MPRGVVVTL | 851-859 HECTD1 | NP_056197.1 | SEQ ID NO. 553 |
| 554. LPKPPGRGV | 341-349 FBXL6 | NP_036294.1 | SEQ ID NO. 554 |
| 555. RLWGEPVNL | 1665-1673 USP9X | NP_004643.2 | SEQ ID NO. 555 |
| 556. RLLDVLAPL | 14-22 COL18A1 | NP_569712.1 | SEQ ID NO. 556 |
| 557. LYILSSHDI | 474-482 FBXO24 | NP_277041.1 | SEQ ID NO. 557 |
| 558. TPMGPGRTV | 235-243 LGALS8 | NP_006490.3 | SEQ ID NO. 558 |
| 559. GPPGTGKTDVAVQI | 823-836 AQR | NP_055506.1 | SEQ ID NO. 559 |
| 560. NEIEDTFRQF | 46-55 ATP6V1F | NP_004222.2 | SEQ ID NO. 560 |
| 561. EEIDLRSVGW | 315-324 UNC93B1 | NP_112192.2 | SEQ ID NO. 561 |
| 562. KYQKGFSLW | 245-253 TRAM1 | NP_055109.1 | SEQ ID NO. 562 |
| 563. VYPDGIRHI | 519-527 SF3B3 | NP_036558.2 | SEQ ID NO. 563 |

TABLE 1-continued

| | Sequence | Position/ Gene symbol | Acc. No. | SEQ ID NO. |
|---|---|---|---|---|
| 564. | KFIDTTSKF | 366-374 RPL3L | NP_005052.1 | SEQ ID NO. 564 |
| 565. | FLDILNTLI | 1729-1737 DNAH8 | NP_001362.1 | SEQ ID NO. 565 |
| 566. | KYITQGQLLQF | 200-210 ELOVL5 | NP_068586.1 | SEQ ID NO. 566 |
| 567. | KYLSVQGQLF | 344-353 MTCH1 | NP_055156.1 | SEQ ID NO. 567 |
| 568. | RYFDEPVEL | 355-363 ARFGAP3 | NP_055385.2 | SEQ ID NO. 568 |
| 569. | KYDEIFYNL | 452-460 EHD2 | NP_055416.2 | SEQ ID NO. 569 |
| 570. | SYIEHIFEI | 61-69 PEA15 | NP_003759.1 | SEQ ID NO. 570 |
| 571. | KFIDPIYQVW | 572-581 RRN3 | NP_060897.2 | SEQ ID NO. 571 |
| 572. | LGYTEGALLAL | 1370-1380 PCDH15 | NP_149045.2 | SEQ ID NO. 572 |
| 573. | KYPSPFFVF | 2-10 DHX9 | NP_085077.1 | SEQ ID NO. 573 |
| 574. | EYPDRIMNTF | 158-167 TUBB4 | NP_006077.1 | SEQ ID NO. 574 |
| 575. | VYISEHEHF | 107-115 CLPTM1 | NP_001285.1 | SEQ ID NO. 575 |
| 576. | KYFLKPEVL | 167-175 KIAA1363 | NP_065843.2 | SEQ ID NO. 576 |
| | Sequence of JY | | | |
| 577. | GPALGRSFL | 78-86 TNFSF7 | NP_001243.1 | SEQ ID NO. 577 |
| | Sequences of the control peptides | | | |
| 578. | ELAGIGILTV | 26-35 MLANA(modified A27->L) | NP_005502.1 | SEQ ID NO. 578 |
| 579. | ILKEPVHGV | 896-904 pol | NP_057849.4 | SEQ ID NO. 579 |
| 580. | GILGFVFTL | 58-66 Symbol does not exist; Gene type: matrix protein M1 | S14616 | SEQ ID NO. 580 |
| 581. | NLVPMVATV | 495-503 Symbol does not exist; Gene type: pp65 | P06725 | SEQ ID NO. 581 |
| 582. | LLDFVRFMGV | 284-293 Symbol does not exist; Gene type: EBNA-6 nuclear protein | P03204 | SEQ ID NO. 582 |
| 583. | GLCTLVAML | 259-267 Symbol does not exist; Gene type: Immediate-early transactivator | NP_039857.1 | SEQ ID NO. 583 |

TABLE 1-continued

| Sequence | Position/Gene symbol | Acc. No. | SEQ ID NO. |
|---|---|---|---|
| 584. CLGGLLTMV | 294-302<br>Symbol does not exist; Gene type: latent membrane protein 2 | AAB59844.1 | SEQ ID NO. 584 |
| 585. APRTVALTA | 9-17<br>HLA-DPB1 | NP_002112 | SEQ ID NO. 585 |

The invention claimed is:

1. An isolated peptide consisting of SEQ ID NO: 448.

2. An isolated peptide consisting of SEQ ID NO: 448, with the proviso that one amino acid of SEQ ID NO: 448 is replaced by another amino acid with similar chemical properties, the peptide being capable of binding to a molecule of the human major histocompatibility complex (MHC) class I.

3. An isolated peptide consisting of SEQ ID NO: 448 and one additional amino acids at the N or/and C-terminus thereof, the peptide being capable of binding to a molecule of the human major histocompatibility complex (MHC) class I.

4. A method for production of an antibody wherein said method comprises the use of an isolated peptide of claim 1.

5. A composition comprising an isolated peptide of claim 1.

6. A composition comprising an isolated peptide of claim 2.

7. A composition comprising an isolated peptide of claim 3.

8. An isolated nucleic acid molecule encoding the isolated peptide of claim 1.

9. An isolated vector comprising the isolated nucleic acid molecule of claim 8.

10. An isolated cell that has been genetically altered to comprise the isolated nucleic acid molecule of claim 8, wherein said isolated cell is capable of expressing the nucleic acid to produce the peptide.

11. An isolated cell that has been genetically altered to comprise the isolated vector of claim 9, wherein said isolated cell is capable of expressing the vector to produce the peptide.

12. An isolated nucleic acid molecule encoding the isolated peptide of claim 2.

13. An isolated vector comprising the isolated nucleic acid molecule of claim 12.

14. An isolated cell that has been genetically altered to comprise the isolated nucleic acid molecule of claim 12, wherein said isolated cell is capable of expressing the nucleic acid to produce the peptide.

15. An isolated cell that has been genetically altered to comprise the isolated vector of claim 13, wherein said isolated cell is capable of expressing the vector to produce the peptide.

16. An isolated nucleic acid molecule encoding the isolated peptide of claim 3.

17. An isolated vector comprising the isolated nucleic acid molecule of claim 16.

18. An isolated cell that has been genetically altered to comprise the isolated nucleic acid molecule of claim 16, wherein said isolated cell is capable of expressing the nucleic acid to produce the peptide.

19. An isolated cell that has been genetically altered to comprise the isolated vector of claim 17, wherein said isolated cell is capable of expressing the vector to produce the peptide.

* * * * *

SEQUENCE LISTING

<160> NUMBER OF SEQ ID NOS: 584

<210> SEQ ID NO 1
<211> LENGTH: 11
<212> TYPE: PRT
<213> ORGANISM: Homo sapiens

<400> SEQUENCE: 1

Val Pro Asp Ser Ser Gly Pro Glu Arg Ile Leu
1               5                   10

<210> SEQ ID NO 2
<211> LENGTH: 9
<212> TYPE: PRT
<213> ORGANISM: Homo sapiens

<400> SEQUENCE: 2

Gly Leu Ala Pro Ser Ile Arg Thr Lys
1               5

<210> SEQ ID NO 3
<211> LENGTH: 9
<212> TYPE: PRT
<213> ORGANISM: Homo sapiens

<400> SEQUENCE: 3

Arg Leu Phe Glu His Pro Leu Tyr Arg
1               5

<210> SEQ ID NO 4
<211> LENGTH: 9
<212> TYPE: PRT
<213> ORGANISM: Homo sapiens

<400> SEQUENCE: 4

Thr Pro Ser Glu Pro His Pro Val Leu
1               5

<210> SEQ ID NO 5
<211> LENGTH: 10
<212> TYPE: PRT
<213> ORGANISM: Homo sapiens

<400> SEQUENCE: 5

Gln Ile Phe Val Lys Thr Leu Thr Gly Lys
1               5                   10

<210> SEQ ID NO 6
<211> LENGTH: 9

```
<212> TYPE: PRT
<213> ORGANISM: Homo sapiens

<400> SEQUENCE: 6

Ser Leu Met His Ser Phe Ile Leu Lys
1               5

<210> SEQ ID NO 7
<211> LENGTH: 9
<212> TYPE: PRT
<213> ORGANISM: Homo sapiens

<400> SEQUENCE: 7

Tyr Pro His Leu His Asn Ala Glu Leu
1               5

<210> SEQ ID NO 8
<211> LENGTH: 9
<212> TYPE: PRT
<213> ORGANISM: Homo sapiens

<400> SEQUENCE: 8

Arg Leu Phe Val Gly Ser Ile Pro Lys
1               5

<210> SEQ ID NO 9
<211> LENGTH: 10
<212> TYPE: PRT
<213> ORGANISM: Homo sapiens

<400> SEQUENCE: 9

Arg Val Phe Pro Asp Lys Gly Tyr Ser Phe
1               5                   10

<210> SEQ ID NO 10
<211> LENGTH: 9
<212> TYPE: PRT
<213> ORGANISM: Homo sapiens

<400> SEQUENCE: 10

Ser Leu Tyr Lys Lys Leu Glu Ile Lys
1               5

<210> SEQ ID NO 11
<211> LENGTH: 10
<212> TYPE: PRT
<213> ORGANISM: Homo sapiens

<400> SEQUENCE: 11

His Pro Val Ser Asp His Glu Ala Thr Leu
1               5                   10

<210> SEQ ID NO 12
<211> LENGTH: 9
<212> TYPE: PRT
<213> ORGANISM: Homo sapiens

<400> SEQUENCE: 12

Leu Pro Thr Arg Val Asp Phe Ser Leu
1               5

<210> SEQ ID NO 13
<211> LENGTH: 11
<212> TYPE: PRT
<213> ORGANISM: Homo sapiens
```

```
<400> SEQUENCE: 13

Lys Ser Phe Gly Ser Ala Gln Glu Phe Ala Trp
1               5                   10

<210> SEQ ID NO 14
<211> LENGTH: 10
<212> TYPE: PRT
<213> ORGANISM: Homo sapiens

<400> SEQUENCE: 14

Ser Pro Ser Thr Ser Arg Thr Pro Leu Leu
1               5                   10

<210> SEQ ID NO 15
<211> LENGTH: 9
<212> TYPE: PRT
<213> ORGANISM: Homo sapiens

<400> SEQUENCE: 15

Ser Thr Phe Asp Ser Pro Ala His Trp
1               5

<210> SEQ ID NO 16
<211> LENGTH: 9
<212> TYPE: PRT
<213> ORGANISM: Homo sapiens

<400> SEQUENCE: 16

Ala Pro Glu Glu His Pro Val Leu Leu
1               5

<210> SEQ ID NO 17
<211> LENGTH: 9
<212> TYPE: PRT
<213> ORGANISM: Homo sapiens

<400> SEQUENCE: 17

Arg Gln Ile Thr Gln Val Tyr Gly Phe
1               5

<210> SEQ ID NO 18
<211> LENGTH: 9
<212> TYPE: PRT
<213> ORGANISM: Homo sapiens

<400> SEQUENCE: 18

Lys Val Ser Asp Tyr Ile Leu Gln His
1               5

<210> SEQ ID NO 19
<211> LENGTH: 9
<212> TYPE: PRT
<213> ORGANISM: Homo sapiens

<400> SEQUENCE: 19

Lys Leu Leu Pro Ser Val Val Leu Lys
1               5

<210> SEQ ID NO 20
<211> LENGTH: 9
<212> TYPE: PRT
<213> ORGANISM: Homo sapiens

<400> SEQUENCE: 20

Gly Val Leu Lys Lys Val Ile Arg His
```

```
1               5
```

<210> SEQ ID NO 21
<211> LENGTH: 10
<212> TYPE: PRT
<213> ORGANISM: Homo sapiens

<400> SEQUENCE: 21

```
Lys Leu Phe Asp His Ala Val Ser Lys Phe
1               5                   10
```

<210> SEQ ID NO 22
<211> LENGTH: 10
<212> TYPE: PRT
<213> ORGANISM: Homo sapiens

<400> SEQUENCE: 22

```
Ile Thr Val Leu Thr Lys Pro Leu Pro Val
1               5                   10
```

<210> SEQ ID NO 23
<211> LENGTH: 9
<212> TYPE: PRT
<213> ORGANISM: Homo sapiens

<400> SEQUENCE: 23

```
His Pro Val His Pro Asp Ile Lys Leu
1               5
```

<210> SEQ ID NO 24
<211> LENGTH: 10
<212> TYPE: PRT
<213> ORGANISM: Homo sapiens

<400> SEQUENCE: 24

```
Ile Pro Arg Ala Ala Leu Leu Pro Leu Leu
1               5                   10
```

<210> SEQ ID NO 25
<211> LENGTH: 9
<212> TYPE: PRT
<213> ORGANISM: Homo sapiens

<400> SEQUENCE: 25

```
Ala Thr Asn Arg Ile Thr Val Thr Trp
1               5
```

<210> SEQ ID NO 26
<211> LENGTH: 9
<212> TYPE: PRT
<213> ORGANISM: Homo sapiens

<400> SEQUENCE: 26

```
Lys Ile Ala Asp Arg Phe Leu Leu Tyr
1               5
```

<210> SEQ ID NO 27
<211> LENGTH: 10
<212> TYPE: PRT
<213> ORGANISM: Homo sapiens

<400> SEQUENCE: 27

```
Asp His Asp Pro Val Asp Lys Ile Val Leu
1               5                   10
```

<210> SEQ ID NO 28
<211> LENGTH: 9
<212> TYPE: PRT
<213> ORGANISM: Homo sapiens

<400> SEQUENCE: 28

Asp His His Gln Glu Val Ile Gly Phe
1               5

<210> SEQ ID NO 29
<211> LENGTH: 9
<212> TYPE: PRT
<213> ORGANISM: Homo sapiens

<400> SEQUENCE: 29

Ile His Asp Leu Asp Asn Ile Ser Phe
1               5

<210> SEQ ID NO 30
<211> LENGTH: 9
<212> TYPE: PRT
<213> ORGANISM: Homo sapiens

<400> SEQUENCE: 30

Asp His Ile Asn Asp Ile Ile Lys Ile
1               5

<210> SEQ ID NO 31
<211> LENGTH: 9
<212> TYPE: PRT
<213> ORGANISM: Homo sapiens

<400> SEQUENCE: 31

Asp His Met Arg Phe Ile Ser Glu Leu
1               5

<210> SEQ ID NO 32
<211> LENGTH: 9
<212> TYPE: PRT
<213> ORGANISM: Homo sapiens

<400> SEQUENCE: 32

Thr His Ser Leu Pro Val Val Val Ile
1               5

<210> SEQ ID NO 33
<211> LENGTH: 11
<212> TYPE: PRT
<213> ORGANISM: Homo sapiens

<400> SEQUENCE: 33

Met Pro Val Gly Pro Asp Ala Ile Leu Arg Tyr
1               5                   10

<210> SEQ ID NO 34
<211> LENGTH: 9
<212> TYPE: PRT
<213> ORGANISM: Homo sapiens

<400> SEQUENCE: 34

Arg Leu Asp Asp Ala Ile His Val Leu
1               5

<210> SEQ ID NO 35
<211> LENGTH: 9
<212> TYPE: PRT

```
<213> ORGANISM: Homo sapiens

<400> SEQUENCE: 35

Gln His Glu Gly Thr Val Asn Ile Phe
1               5

<210> SEQ ID NO 36
<211> LENGTH: 9
<212> TYPE: PRT
<213> ORGANISM: Homo sapiens

<400> SEQUENCE: 36

Glu Thr Val Asn Ile Trp Thr His Phe
1               5

<210> SEQ ID NO 37
<211> LENGTH: 9
<212> TYPE: PRT
<213> ORGANISM: Homo sapiens

<400> SEQUENCE: 37

Val His Ile Leu Asp Thr Glu Thr Phe
1               5

<210> SEQ ID NO 38
<211> LENGTH: 10
<212> TYPE: PRT
<213> ORGANISM: Homo sapiens

<400> SEQUENCE: 38

Gln Thr Pro Asp Phe Thr Pro Thr Lys Tyr
1               5                   10

<210> SEQ ID NO 39
<211> LENGTH: 9
<212> TYPE: PRT
<213> ORGANISM: Homo sapiens

<400> SEQUENCE: 39

Arg His Val Glu Val Phe Glu Leu Leu
1               5

<210> SEQ ID NO 40
<211> LENGTH: 9
<212> TYPE: PRT
<213> ORGANISM: Homo sapiens

<400> SEQUENCE: 40

Thr Thr Ile Asp Ile Gly Val Lys Tyr
1               5

<210> SEQ ID NO 41
<211> LENGTH: 9
<212> TYPE: PRT
<213> ORGANISM: Homo sapiens

<400> SEQUENCE: 41

Asp Leu Ile Glu His Phe Ser Gln Phe
1               5

<210> SEQ ID NO 42
<211> LENGTH: 9
<212> TYPE: PRT
<213> ORGANISM: Homo sapiens

<400> SEQUENCE: 42
```

```
Glu Thr Val Trp Arg Leu Glu Glu Phe
1               5
```

<210> SEQ ID NO 43
<211> LENGTH: 9
<212> TYPE: PRT
<213> ORGANISM: Homo sapiens
<400> SEQUENCE: 43

```
Asp Val Leu Glu Ser Val Asn Leu Leu
1               5
```

<210> SEQ ID NO 44
<211> LENGTH: 9
<212> TYPE: PRT
<213> ORGANISM: Homo sapiens
<400> SEQUENCE: 44

```
Ile His Asp Asp Phe Val Thr Thr Phe
1               5
```

<210> SEQ ID NO 45
<211> LENGTH: 9
<212> TYPE: PRT
<213> ORGANISM: Homo sapiens
<400> SEQUENCE: 45

```
Ile His Ile Pro Ile Asn Asn Ile Ile
1               5
```

<210> SEQ ID NO 46
<211> LENGTH: 9
<212> TYPE: PRT
<213> ORGANISM: Homo sapiens
<400> SEQUENCE: 46

```
Ile His Leu Ile Asp Pro Asn Thr Leu
1               5
```

<210> SEQ ID NO 47
<211> LENGTH: 9
<212> TYPE: PRT
<213> ORGANISM: Homo sapiens
<400> SEQUENCE: 47

```
Ile His Val Ile Gly Gly Asn Asp Val
1               5
```

<210> SEQ ID NO 48
<211> LENGTH: 9
<212> TYPE: PRT
<213> ORGANISM: Homo sapiens
<400> SEQUENCE: 48

```
Lys Ala Phe Gln Lys Ile Val Val Leu
1               5
```

<210> SEQ ID NO 49
<211> LENGTH: 9
<212> TYPE: PRT
<213> ORGANISM: Homo sapiens
<400> SEQUENCE: 49

```
Tyr Gln Asp Leu Leu Asn Val Lys Leu
1               5
```

```
<210> SEQ ID NO 50
<211> LENGTH: 9
<212> TYPE: PRT
<213> ORGANISM: Homo sapiens

<400> SEQUENCE: 50

Gly His Tyr Glu Val Ala Glu Leu Leu
1               5

<210> SEQ ID NO 51
<211> LENGTH: 10
<212> TYPE: PRT
<213> ORGANISM: Homo sapiens

<400> SEQUENCE: 51

Leu Val Val Tyr Pro Trp Thr Gln Arg Phe
1               5                   10

<210> SEQ ID NO 52
<211> LENGTH: 9
<212> TYPE: PRT
<213> ORGANISM: Homo sapiens

<400> SEQUENCE: 52

Met His Leu Arg Gln Tyr Glu Leu Leu
1               5

<210> SEQ ID NO 53
<211> LENGTH: 9
<212> TYPE: PRT
<213> ORGANISM: Homo sapiens

<400> SEQUENCE: 53

Glu Ala Ile Glu Gln Ile Leu Lys Tyr
1               5

<210> SEQ ID NO 54
<211> LENGTH: 11
<212> TYPE: PRT
<213> ORGANISM: Homo sapiens

<400> SEQUENCE: 54

Asp Val Ala Glu Gly Asp Leu Ile Glu His Phe
1               5                   10

<210> SEQ ID NO 55
<211> LENGTH: 8
<212> TYPE: PRT
<213> ORGANISM: Homo sapiens

<400> SEQUENCE: 55

Asp Val Leu Gln Lys Ile Lys Tyr
1               5

<210> SEQ ID NO 56
<211> LENGTH: 10
<212> TYPE: PRT
<213> ORGANISM: Homo sapiens

<400> SEQUENCE: 56

Asp Ser Phe Pro Met Glu Ile Arg Gln Tyr
1               5                   10

<210> SEQ ID NO 57
```

```
<211> LENGTH: 9
<212> TYPE: PRT
<213> ORGANISM: Homo sapiens

<400> SEQUENCE: 57

Asp Val Ile Ser Asn Ile Glu Thr Phe
1               5

<210> SEQ ID NO 58
<211> LENGTH: 9
<212> TYPE: PRT
<213> ORGANISM: Homo sapiens

<400> SEQUENCE: 58

Asp Val Ile Arg Leu Ile Met Gln Tyr
1               5

<210> SEQ ID NO 59
<211> LENGTH: 9
<212> TYPE: PRT
<213> ORGANISM: Homo sapiens

<400> SEQUENCE: 59

Asp Val Ile Glu Arg Val Ile Gln Tyr
1               5

<210> SEQ ID NO 60
<211> LENGTH: 10
<212> TYPE: PRT
<213> ORGANISM: Homo sapiens

<400> SEQUENCE: 60

Asp Val Ile Ala Gln Gly Ile Gly Lys Leu
1               5                   10

<210> SEQ ID NO 61
<211> LENGTH: 10
<212> TYPE: PRT
<213> ORGANISM: Homo sapiens

<400> SEQUENCE: 61

Asp Val Phe Asn Glu Lys Gly Trp Asn Tyr
1               5                   10

<210> SEQ ID NO 62
<211> LENGTH: 9
<212> TYPE: PRT
<213> ORGANISM: Homo sapiens

<400> SEQUENCE: 62

Thr His Leu Asp Ser Val Thr Lys Ile
1               5

<210> SEQ ID NO 63
<211> LENGTH: 9
<212> TYPE: PRT
<213> ORGANISM: Homo sapiens

<400> SEQUENCE: 63

Asp Val Ala Gly Ile Ile Ala Asp Tyr
1               5

<210> SEQ ID NO 64
<211> LENGTH: 9
<212> TYPE: PRT
<213> ORGANISM: Homo sapiens
```

```
<400> SEQUENCE: 64

Thr Ala Ala Pro Phe Pro Phe His Leu
1               5

<210> SEQ ID NO 65
<211> LENGTH: 9
<212> TYPE: PRT
<213> ORGANISM: Homo sapiens

<400> SEQUENCE: 65

Asp Thr Leu Asp Lys Val Phe Thr Tyr
1               5

<210> SEQ ID NO 66
<211> LENGTH: 9
<212> TYPE: PRT
<213> ORGANISM: Homo sapiens

<400> SEQUENCE: 66

Asp Thr Ile Ser Pro Thr Leu Gly Phe
1               5

<210> SEQ ID NO 67
<211> LENGTH: 11
<212> TYPE: PRT
<213> ORGANISM: Homo sapiens

<400> SEQUENCE: 67

Asp Thr Gly Ile Leu Asp Ser Ile Gly Arg Phe
1               5                   10

<210> SEQ ID NO 68
<211> LENGTH: 9
<212> TYPE: PRT
<213> ORGANISM: Homo sapiens

<400> SEQUENCE: 68

Val Val Tyr Pro Trp Thr Gln Arg Phe
1               5

<210> SEQ ID NO 69
<211> LENGTH: 10
<212> TYPE: PRT
<213> ORGANISM: Homo sapiens

<400> SEQUENCE: 69

Glu Val Val Ala Gly Ile Lys Glu Tyr Phe
1               5                   10

<210> SEQ ID NO 70
<211> LENGTH: 9
<212> TYPE: PRT
<213> ORGANISM: Homo sapiens

<400> SEQUENCE: 70

Ser Ser Val Pro Gly Val Arg Leu Leu
1               5

<210> SEQ ID NO 71
<211> LENGTH: 11
<212> TYPE: PRT
<213> ORGANISM: Homo sapiens

<400> SEQUENCE: 71
```

```
Ser Val Val Asp Ala Gly Ile Ser Arg Phe
1               5                   10
```

<210> SEQ ID NO 72
<211> LENGTH: 9
<212> TYPE: PRT
<213> ORGANISM: Homo sapiens

<400> SEQUENCE: 72

```
Glu Val Ile Pro Pro Met Lys Glu Phe
1               5
```

<210> SEQ ID NO 73
<211> LENGTH: 9
<212> TYPE: PRT
<213> ORGANISM: Homo sapiens

<400> SEQUENCE: 73

```
Glu Val Ile Pro Pro Tyr Tyr Ser Tyr
1               5
```

<210> SEQ ID NO 74
<211> LENGTH: 9
<212> TYPE: PRT
<213> ORGANISM: Homo sapiens

<400> SEQUENCE: 74

```
Glu Val Asn Gly Leu Ile Ser Met Tyr
1               5
```

<210> SEQ ID NO 75
<211> LENGTH: 10
<212> TYPE: PRT
<213> ORGANISM: Homo sapiens

<400> SEQUENCE: 75

```
Glu Val Ile Asp Leu Met Ile Lys Glu Tyr
1               5                   10
```

<210> SEQ ID NO 76
<211> LENGTH: 9
<212> TYPE: PRT
<213> ORGANISM: Homo sapiens

<400> SEQUENCE: 76

```
Glu Val Val Ala Gly Ile Lys Glu Tyr
1               5
```

<210> SEQ ID NO 77
<211> LENGTH: 9
<212> TYPE: PRT
<213> ORGANISM: Homo sapiens

<400> SEQUENCE: 77

```
Glu Val Phe Pro Leu Ala Met Asn Tyr
1               5
```

<210> SEQ ID NO 78
<211> LENGTH: 9
<212> TYPE: PRT
<213> ORGANISM: Homo sapiens

<400> SEQUENCE: 78

```
Glu Val Val Glu Arg Val Leu Thr Phe
1               5
```

<210> SEQ ID NO 79
<211> LENGTH: 10
<212> TYPE: PRT
<213> ORGANISM: Homo sapiens

<400> SEQUENCE: 79

Ser His Ser Pro Phe Gly Leu Asp Ser Phe
1               5                   10

<210> SEQ ID NO 80
<211> LENGTH: 9
<212> TYPE: PRT
<213> ORGANISM: Homo sapiens

<400> SEQUENCE: 80

Phe Gly Val Asp Arg Ala Ile Leu Tyr
1               5

<210> SEQ ID NO 81
<211> LENGTH: 9
<212> TYPE: PRT
<213> ORGANISM: Homo sapiens

<400> SEQUENCE: 81

Ser His Ser Asp Tyr Leu Leu Thr Ile
1               5

<210> SEQ ID NO 82
<211> LENGTH: 9
<212> TYPE: PRT
<213> ORGANISM: Homo sapiens

<400> SEQUENCE: 82

Ser His Leu Asp Tyr Asp Ile Thr Leu
1               5

<210> SEQ ID NO 83
<211> LENGTH: 9
<212> TYPE: PRT
<213> ORGANISM: Homo sapiens

<400> SEQUENCE: 83

Ser His Phe Val Ser Asp Val Val Ile
1               5

<210> SEQ ID NO 84
<211> LENGTH: 9
<212> TYPE: PRT
<213> ORGANISM: Homo sapiens

<400> SEQUENCE: 84

Glu Val Thr Glu Leu Leu Ala Arg Tyr
1               5

<210> SEQ ID NO 85
<211> LENGTH: 11
<212> TYPE: PRT
<213> ORGANISM: Homo sapiens

<400> SEQUENCE: 85

Glu Thr Ala Asp Thr Leu Met Gly Leu Arg Tyr
1               5                   10

<210> SEQ ID NO 86
<211> LENGTH: 9

```
<212> TYPE: PRT
<213> ORGANISM: Homo sapiens

<400> SEQUENCE: 86

Glu His Ala His Leu Ile Val Val Leu
1               5

<210> SEQ ID NO 87
<211> LENGTH: 9
<212> TYPE: PRT
<213> ORGANISM: Homo sapiens

<400> SEQUENCE: 87

Glu His Ser Leu Val Ile Asp Thr Leu
1               5

<210> SEQ ID NO 88
<211> LENGTH: 9
<212> TYPE: PRT
<213> ORGANISM: Homo sapiens

<400> SEQUENCE: 88

Glu Ile Ala Glu Ala Tyr Leu Gly Tyr
1               5

<210> SEQ ID NO 89
<211> LENGTH: 10
<212> TYPE: PRT
<213> ORGANISM: Homo sapiens

<400> SEQUENCE: 89

Glu Ile Tyr Gly Gly Ser Asp Ser Arg Phe
1               5                   10

<210> SEQ ID NO 90
<211> LENGTH: 9
<212> TYPE: PRT
<213> ORGANISM: Homo sapiens

<400> SEQUENCE: 90

Glu Leu Ile Ala Lys Ile Pro Asn Phe
1               5

<210> SEQ ID NO 91
<211> LENGTH: 9
<212> TYPE: PRT
<213> ORGANISM: Homo sapiens

<400> SEQUENCE: 91

Glu Val Ile Lys Asn Phe Ile Gln Tyr
1               5

<210> SEQ ID NO 92
<211> LENGTH: 11
<212> TYPE: PRT
<213> ORGANISM: Homo sapiens

<400> SEQUENCE: 92

Glu Thr Ala Asp Thr Leu Leu Ala Leu Arg Tyr
1               5                   10

<210> SEQ ID NO 93
<211> LENGTH: 10
<212> TYPE: PRT
<213> ORGANISM: Homo sapiens
```

```
<400> SEQUENCE: 93

Glu Val Val Ser Glu Pro Phe Arg Ser Phe
1               5                   10

<210> SEQ ID NO 94
<211> LENGTH: 10
<212> TYPE: PRT
<213> ORGANISM: Homo sapiens

<400> SEQUENCE: 94

Glu Thr Phe Asp Ala Gly Leu Gln Ala Phe
1               5                   10

<210> SEQ ID NO 95
<211> LENGTH: 9
<212> TYPE: PRT
<213> ORGANISM: Homo sapiens

<400> SEQUENCE: 95

Ser His Ser Gln Leu Met Gln Leu Ile
1               5

<210> SEQ ID NO 96
<211> LENGTH: 9
<212> TYPE: PRT
<213> ORGANISM: Homo sapiens

<400> SEQUENCE: 96

Glu Thr Val Arg Glu Leu Thr Glu Phe
1               5

<210> SEQ ID NO 97
<211> LENGTH: 9
<212> TYPE: PRT
<213> ORGANISM: Homo sapiens

<400> SEQUENCE: 97

Glu Val Ala Ala Thr Glu Ile Lys Met
1               5

<210> SEQ ID NO 98
<211> LENGTH: 9
<212> TYPE: PRT
<213> ORGANISM: Homo sapiens

<400> SEQUENCE: 98

Glu Val Ala Ala Val Leu Leu His Phe
1               5

<210> SEQ ID NO 99
<211> LENGTH: 9
<212> TYPE: PRT
<213> ORGANISM: Homo sapiens

<400> SEQUENCE: 99

Glu Val Phe Asp Lys Thr Tyr Gln Phe
1               5

<210> SEQ ID NO 100
<211> LENGTH: 9
<212> TYPE: PRT
<213> ORGANISM: Homo sapiens

<400> SEQUENCE: 100

Glu Leu Val Lys Arg Ile Leu Asn Phe
```

<210> SEQ ID NO 101
<211> LENGTH: 9
<212> TYPE: PRT
<213> ORGANISM: Homo sapiens

<400> SEQUENCE: 101

Ala His Asp Asp Gly Arg Trp Ser Leu
1               5

<210> SEQ ID NO 102
<211> LENGTH: 9
<212> TYPE: PRT
<213> ORGANISM: Homo sapiens

<400> SEQUENCE: 102

Ser Val Val Ser Val Ile Ser Arg Phe
1               5

<210> SEQ ID NO 103
<211> LENGTH: 9
<212> TYPE: PRT
<213> ORGANISM: Homo sapiens

<400> SEQUENCE: 103

Ser Val Val Glu Leu Ile Asn His Tyr
1               5

<210> SEQ ID NO 104
<211> LENGTH: 9
<212> TYPE: PRT
<213> ORGANISM: Homo sapiens

<400> SEQUENCE: 104

Ser Val Val Asp Leu Ile Asn His Tyr
1               5

<210> SEQ ID NO 105
<211> LENGTH: 9
<212> TYPE: PRT
<213> ORGANISM: Homo sapiens

<400> SEQUENCE: 105

Ala His Val Asp Leu Ile Glu Lys Leu
1               5

<210> SEQ ID NO 106
<211> LENGTH: 9
<212> TYPE: PRT
<213> ORGANISM: Homo sapiens

<400> SEQUENCE: 106

Phe His Asn Glu Leu Leu Thr Gln Leu
1               5

<210> SEQ ID NO 107
<211> LENGTH: 9
<212> TYPE: PRT
<213> ORGANISM: Homo sapiens

<400> SEQUENCE: 107

Ser Val Ile Glu Ala Val Ala His Phe
1               5

```
<210> SEQ ID NO 108
<211> LENGTH: 9
<212> TYPE: PRT
<213> ORGANISM: Homo sapiens

<400> SEQUENCE: 108

Gly His Phe Glu Lys Pro Leu Phe Leu
1               5

<210> SEQ ID NO 109
<211> LENGTH: 9
<212> TYPE: PRT
<213> ORGANISM: Homo sapiens

<400> SEQUENCE: 109

Gly His Asp Ala Ser Gln Ile Thr Leu
1               5

<210> SEQ ID NO 110
<211> LENGTH: 9
<212> TYPE: PRT
<213> ORGANISM: Homo sapiens

<400> SEQUENCE: 110

Ser Ala Val Asp Phe Ile Arg Thr Leu
1               5

<210> SEQ ID NO 111
<211> LENGTH: 9
<212> TYPE: PRT
<213> ORGANISM: Homo sapiens

<400> SEQUENCE: 111

Ile Ser Thr Pro Val Ile Arg Thr Phe
1               5

<210> SEQ ID NO 112
<211> LENGTH: 10
<212> TYPE: PRT
<213> ORGANISM: Homo sapiens

<400> SEQUENCE: 112

Gly Val Ile Glu Lys Leu Leu Thr Ser Tyr
1               5                   10

<210> SEQ ID NO 113
<211> LENGTH: 9
<212> TYPE: PRT
<213> ORGANISM: Homo sapiens

<400> SEQUENCE: 113

Ser His Asp Leu Thr Leu Val Asn Leu
1               5

<210> SEQ ID NO 114
<211> LENGTH: 9
<212> TYPE: PRT
<213> ORGANISM: Homo sapiens

<400> SEQUENCE: 114

Phe Pro Ser Leu Arg Glu Ala Ala Leu
1               5

<210> SEQ ID NO 115
<211> LENGTH: 9
<212> TYPE: PRT
```

<213> ORGANISM: Homo sapiens

<400> SEQUENCE: 115

Ser Ile Phe Lys Gln Pro Val Thr Lys
1               5

<210> SEQ ID NO 116
<211> LENGTH: 9
<212> TYPE: PRT
<213> ORGANISM: Homo sapiens

<400> SEQUENCE: 116

Lys Pro Asn Ala Asn Arg Ile Ala Leu
1               5

<210> SEQ ID NO 117
<211> LENGTH: 9
<212> TYPE: PRT
<213> ORGANISM: Homo sapiens

<400> SEQUENCE: 117

Lys Leu Tyr Glu Met Ile Leu Lys Arg
1               5

<210> SEQ ID NO 118
<211> LENGTH: 9
<212> TYPE: PRT
<213> ORGANISM: Homo sapiens

<400> SEQUENCE: 118

Ser Leu Phe Ser Arg Leu Phe Gly Lys
1               5

<210> SEQ ID NO 119
<211> LENGTH: 9
<212> TYPE: PRT
<213> ORGANISM: Homo sapiens

<400> SEQUENCE: 119

Lys Leu Phe Asp Lys Leu Leu Glu Tyr
1               5

<210> SEQ ID NO 120
<211> LENGTH: 12
<212> TYPE: PRT
<213> ORGANISM: Homo sapiens

<400> SEQUENCE: 120

Ser Leu Phe Pro Asn Ser Pro Lys Trp Thr Ser Lys
1               5                   10

<210> SEQ ID NO 121
<211> LENGTH: 9
<212> TYPE: PRT
<213> ORGANISM: Homo sapiens

<400> SEQUENCE: 121

Leu Glu Ser Leu Asp Gln Leu Glu Leu
1               5

<210> SEQ ID NO 122
<211> LENGTH: 10
<212> TYPE: PRT
<213> ORGANISM: Homo sapiens

<400> SEQUENCE: 122

Val Val Asn Lys Val Pro Leu Thr Gly Lys
1               5                   10

<210> SEQ ID NO 123
<211> LENGTH: 9
<212> TYPE: PRT
<213> ORGANISM: Homo sapiens

<400> SEQUENCE: 123

Ser Val Tyr Asp Ser Val Leu Gln Lys
1               5

<210> SEQ ID NO 124
<211> LENGTH: 9
<212> TYPE: PRT
<213> ORGANISM: Homo sapiens

<400> SEQUENCE: 124

Ser Val Tyr Val Leu Val Arg Gln Lys
1               5

<210> SEQ ID NO 125
<211> LENGTH: 9
<212> TYPE: PRT
<213> ORGANISM: Homo sapiens

<400> SEQUENCE: 125

Ile Leu Glu Asn Ile Gln Arg Asn Lys
1               5

<210> SEQ ID NO 126
<211> LENGTH: 10
<212> TYPE: PRT
<213> ORGANISM: Homo sapiens

<400> SEQUENCE: 126

Gly Ser Tyr Asn Lys Val Phe Leu Ala Lys
1               5                   10

<210> SEQ ID NO 127
<211> LENGTH: 9
<212> TYPE: PRT
<213> ORGANISM: Homo sapiens

<400> SEQUENCE: 127

Thr Glu Ser Gly Leu Asn Val Thr Leu
1               5

<210> SEQ ID NO 128
<211> LENGTH: 9
<212> TYPE: PRT
<213> ORGANISM: Homo sapiens

<400> SEQUENCE: 128

Thr Glu His Gly Val Glu Val Val Leu
1               5

<210> SEQ ID NO 129
<211> LENGTH: 9
<212> TYPE: PRT
<213> ORGANISM: Homo sapiens

<400> SEQUENCE: 129

Thr Glu Ala Arg Phe Gly Ala Gln Leu
1               5

<210> SEQ ID NO 130
<211> LENGTH: 9
<212> TYPE: PRT
<213> ORGANISM: Homo sapiens

<400> SEQUENCE: 130

Thr Leu Ala Asp Ile Leu Leu Tyr Tyr
1               5

<210> SEQ ID NO 131
<211> LENGTH: 10
<212> TYPE: PRT
<213> ORGANISM: Homo sapiens

<400> SEQUENCE: 131

Leu Val Phe Pro Ser Glu Ile Val Gly Lys
1               5                   10

<210> SEQ ID NO 132
<211> LENGTH: 10
<212> TYPE: PRT
<213> ORGANISM: Homo sapiens

<400> SEQUENCE: 132

Val Leu Phe Gly Lys Ala Leu Asn Pro Lys
1               5                   10

<210> SEQ ID NO 133
<211> LENGTH: 9
<212> TYPE: PRT
<213> ORGANISM: Homo sapiens

<400> SEQUENCE: 133

Arg Pro Glu Leu Val Arg Pro Ala Leu
1               5

<210> SEQ ID NO 134
<211> LENGTH: 10
<212> TYPE: PRT
<213> ORGANISM: Homo sapiens

<400> SEQUENCE: 134

Val Pro Asn Gln Lys Arg Leu Thr Leu Leu
1               5                   10

<210> SEQ ID NO 135
<211> LENGTH: 9
<212> TYPE: PRT
<213> ORGANISM: Homo sapiens

<400> SEQUENCE: 135

Gln Leu Tyr Trp Ser His Pro Arg Lys
1               5

<210> SEQ ID NO 136
<211> LENGTH: 9
<212> TYPE: PRT
<213> ORGANISM: Homo sapiens

<400> SEQUENCE: 136

Ser Val Tyr Val Tyr Lys Val Leu Lys
1               5

<210> SEQ ID NO 137

```
<211> LENGTH: 9
<212> TYPE: PRT
<213> ORGANISM: Homo sapiens

<400> SEQUENCE: 137

Arg Glu Lys Leu Gln Glu Glu Met Leu
1               5

<210> SEQ ID NO 138
<211> LENGTH: 12
<212> TYPE: PRT
<213> ORGANISM: Homo sapiens

<400> SEQUENCE: 138

Arg Val Phe Ser Gly Leu Val Ser Thr Gly Leu Lys
1               5                   10

<210> SEQ ID NO 139
<211> LENGTH: 10
<212> TYPE: PRT
<213> ORGANISM: Homo sapiens

<400> SEQUENCE: 139

Lys Pro Arg Asp Val Ser Ser Val Glu Leu
1               5                   10

<210> SEQ ID NO 140
<211> LENGTH: 9
<212> TYPE: PRT
<213> ORGANISM: Homo sapiens

<400> SEQUENCE: 140

Asn Glu Phe Pro Glu Pro Ile Lys Leu
1               5

<210> SEQ ID NO 141
<211> LENGTH: 9
<212> TYPE: PRT
<213> ORGANISM: Homo sapiens

<400> SEQUENCE: 141

Lys Thr Tyr Gly Glu Ile Phe Glu Lys
1               5

<210> SEQ ID NO 142
<211> LENGTH: 9
<212> TYPE: PRT
<213> ORGANISM: Homo sapiens

<400> SEQUENCE: 142

Arg Ile Leu Phe Phe Asn Thr Pro Lys
1               5

<210> SEQ ID NO 143
<211> LENGTH: 9
<212> TYPE: PRT
<213> ORGANISM: Homo sapiens

<400> SEQUENCE: 143

Arg Val Phe Pro Trp Phe Ser Val Lys
1               5

<210> SEQ ID NO 144
<211> LENGTH: 9
<212> TYPE: PRT
<213> ORGANISM: Homo sapiens
```

```
<400> SEQUENCE: 144

Ser Glu Val Gln Asp Arg Val Met Leu
1               5

<210> SEQ ID NO 145
<211> LENGTH: 9
<212> TYPE: PRT
<213> ORGANISM: Homo sapiens

<400> SEQUENCE: 145

Ser Leu Trp Asp Arg Leu Ile Phe His
1               5

<210> SEQ ID NO 146
<211> LENGTH: 9
<212> TYPE: PRT
<213> ORGANISM: Homo sapiens

<400> SEQUENCE: 146

Lys Val Tyr Asn Ile Gln Ile Arg Tyr
1               5

<210> SEQ ID NO 147
<211> LENGTH: 9
<212> TYPE: PRT
<213> ORGANISM: Homo sapiens

<400> SEQUENCE: 147

Arg Leu Leu Glu Met Ile Leu Asn Lys
1               5

<210> SEQ ID NO 148
<211> LENGTH: 9
<212> TYPE: PRT
<213> ORGANISM: Homo sapiens

<400> SEQUENCE: 148

Ser Glu Asp Lys Lys Asn Ile Ile Leu
1               5

<210> SEQ ID NO 149
<211> LENGTH: 9
<212> TYPE: PRT
<213> ORGANISM: Homo sapiens

<400> SEQUENCE: 149

Tyr Glu Glu Leu Val Arg Met Val Leu
1               5

<210> SEQ ID NO 150
<211> LENGTH: 9
<212> TYPE: PRT
<213> ORGANISM: Homo sapiens

<400> SEQUENCE: 150

Gly Glu Ile Thr Gly Glu Val His Met
1               5

<210> SEQ ID NO 151
<211> LENGTH: 9
<212> TYPE: PRT
<213> ORGANISM: Homo sapiens

<400> SEQUENCE: 151
```

-continued

```
Ile Val Ala Gly Ser Leu Ile Thr Lys
1               5

<210> SEQ ID NO 152
<211> LENGTH: 12
<212> TYPE: PRT
<213> ORGANISM: Homo sapiens

<400> SEQUENCE: 152

Ala Pro Arg Ile Ile Thr Gly Pro Ala Pro Val Leu
1               5                   10

<210> SEQ ID NO 153
<211> LENGTH: 10
<212> TYPE: PRT
<213> ORGANISM: Homo sapiens

<400> SEQUENCE: 153

Gly Leu Ala Ser Phe Lys Ser Phe Leu Lys
1               5                   10

<210> SEQ ID NO 154
<211> LENGTH: 10
<212> TYPE: PRT
<213> ORGANISM: Homo sapiens

<400> SEQUENCE: 154

Phe Pro Asn Ser Pro Lys Trp Thr Ser Lys
1               5                   10

<210> SEQ ID NO 155
<211> LENGTH: 9
<212> TYPE: PRT
<213> ORGANISM: Homo sapiens

<400> SEQUENCE: 155

Phe Val Ile Glu Thr Ala Arg Gln Leu
1               5

<210> SEQ ID NO 156
<211> LENGTH: 10
<212> TYPE: PRT
<213> ORGANISM: Homo sapiens

<400> SEQUENCE: 156

Ile Glu Val Asp Gly Lys Gln Val Glu Leu
1               5                   10

<210> SEQ ID NO 157
<211> LENGTH: 9
<212> TYPE: PRT
<213> ORGANISM: Homo sapiens

<400> SEQUENCE: 157

Gly Glu Leu Thr Gly Glu Val Arg Met
1               5

<210> SEQ ID NO 158
<211> LENGTH: 10
<212> TYPE: PRT
<213> ORGANISM: Homo sapiens

<400> SEQUENCE: 158

Gly Glu Ser Asp Asp Ser Ile Leu Arg Leu
1               5                   10
```

```
<210> SEQ ID NO 159
<211> LENGTH: 12
<212> TYPE: PRT
<213> ORGANISM: Homo sapiens

<400> SEQUENCE: 159

Gly Glu Gly Asp Phe Leu Ala Glu Gly Gly Gly Val
1               5                   10

<210> SEQ ID NO 160
<211> LENGTH: 7
<212> TYPE: PRT
<213> ORGANISM: Homo sapiens

<400> SEQUENCE: 160

Asp Asn Phe Pro Gln Ser Leu
1               5

<210> SEQ ID NO 161
<211> LENGTH: 9
<212> TYPE: PRT
<213> ORGANISM: Homo sapiens

<400> SEQUENCE: 161

Gly Leu Thr Asp Val Ile Leu Tyr His
1               5

<210> SEQ ID NO 162
<211> LENGTH: 11
<212> TYPE: PRT
<213> ORGANISM: Homo sapiens

<400> SEQUENCE: 162

Ala Ala Leu Val Ala Ser Gly Val Ala Leu Tyr
1               5                   10

<210> SEQ ID NO 163
<211> LENGTH: 10
<212> TYPE: PRT
<213> ORGANISM: Homo sapiens

<400> SEQUENCE: 163

Ala Glu Ile Arg His Val Leu Val Thr Leu
1               5                   10

<210> SEQ ID NO 164
<211> LENGTH: 9
<212> TYPE: PRT
<213> ORGANISM: Homo sapiens

<400> SEQUENCE: 164

Ala Glu Pro Glu Glu Val Glu Val Leu
1               5

<210> SEQ ID NO 165
<211> LENGTH: 10
<212> TYPE: PRT
<213> ORGANISM: Homo sapiens

<400> SEQUENCE: 165

Ala Ile Ile Asp His Ile Phe Ala Ser Lys
1               5                   10

<210> SEQ ID NO 166
<211> LENGTH: 11
```

```
<212> TYPE: PRT
<213> ORGANISM: Homo sapiens

<400> SEQUENCE: 166

Ala Leu Leu Asp Gly Ser Asn Val Val Phe Lys
1               5                   10

<210> SEQ ID NO 167
<211> LENGTH: 9
<212> TYPE: PRT
<213> ORGANISM: Homo sapiens

<400> SEQUENCE: 167

Ala Met Leu Asp Thr Val Val Phe Lys
1               5

<210> SEQ ID NO 168
<211> LENGTH: 9
<212> TYPE: PRT
<213> ORGANISM: Homo sapiens

<400> SEQUENCE: 168

Ala Pro Ala Arg Leu Phe Ala Leu Leu
1               5

<210> SEQ ID NO 169
<211> LENGTH: 10
<212> TYPE: PRT
<213> ORGANISM: Homo sapiens

<400> SEQUENCE: 169

Ala Val Asn Ala His Ser Asn Ile Leu Lys
1               5                   10

<210> SEQ ID NO 170
<211> LENGTH: 9
<212> TYPE: PRT
<213> ORGANISM: Homo sapiens

<400> SEQUENCE: 170

Ala Pro Arg Pro Gly Val Leu Leu Leu
1               5

<210> SEQ ID NO 171
<211> LENGTH: 9
<212> TYPE: PRT
<213> ORGANISM: Homo sapiens

<400> SEQUENCE: 171

Glu Ala Phe Pro Leu Arg Val Ile Asp
1               5

<210> SEQ ID NO 172
<211> LENGTH: 9
<212> TYPE: PRT
<213> ORGANISM: Homo sapiens

<400> SEQUENCE: 172

Gly Val Ala Asp Lys Ile Leu Lys Lys
1               5

<210> SEQ ID NO 173
<211> LENGTH: 10
<212> TYPE: PRT
<213> ORGANISM: Homo sapiens
```

-continued

```
<400> SEQUENCE: 173

Ala Val Phe Pro Lys Pro Phe Val Glu Lys
1               5                   10

<210> SEQ ID NO 174
<211> LENGTH: 10
<212> TYPE: PRT
<213> ORGANISM: Homo sapiens

<400> SEQUENCE: 174

Val Val Tyr Val Gly Gly Ile Leu Thr Lys
1               5                   10

<210> SEQ ID NO 175
<211> LENGTH: 9
<212> TYPE: PRT
<213> ORGANISM: Homo sapiens

<400> SEQUENCE: 175

His Leu Glu Asp Ile Val Arg Gln Lys
1               5

<210> SEQ ID NO 176
<211> LENGTH: 10
<212> TYPE: PRT
<213> ORGANISM: Homo sapiens

<400> SEQUENCE: 176

Val Thr Leu Thr Leu Val Ile Leu Ser Tyr
1               5                   10

<210> SEQ ID NO 177
<211> LENGTH: 10
<212> TYPE: PRT
<213> ORGANISM: Homo sapiens

<400> SEQUENCE: 177

Ser Leu Leu Ser Leu Val Thr Gly Leu Lys
1               5                   10

<210> SEQ ID NO 178
<211> LENGTH: 9
<212> TYPE: PRT
<213> ORGANISM: Homo sapiens

<400> SEQUENCE: 178

Gln Thr Tyr Val Gly Ile Thr Glu Lys
1               5

<210> SEQ ID NO 179
<211> LENGTH: 9
<212> TYPE: PRT
<213> ORGANISM: Homo sapiens

<400> SEQUENCE: 179

His Glu Asp Lys Ile Arg Val Val Leu
1               5

<210> SEQ ID NO 180
<211> LENGTH: 9
<212> TYPE: PRT
<213> ORGANISM: Homo sapiens

<400> SEQUENCE: 180

Gln Ile Ser Ile Pro Phe Leu Leu Lys
```

```
<210> SEQ ID NO 181
<211> LENGTH: 9
<212> TYPE: PRT
<213> ORGANISM: Homo sapiens

<400> SEQUENCE: 181

Gly Leu Met Gly Phe Ile Val Tyr Lys
1               5

<210> SEQ ID NO 182
<211> LENGTH: 9
<212> TYPE: PRT
<213> ORGANISM: Homo sapiens

<400> SEQUENCE: 182

Phe Ala Asp Gln Glu Val Arg Ser Leu
1               5

<210> SEQ ID NO 183
<211> LENGTH: 9
<212> TYPE: PRT
<213> ORGANISM: Homo sapiens

<400> SEQUENCE: 183

Ile Val Ala Leu Ile Leu Ser Thr Lys
1               5

<210> SEQ ID NO 184
<211> LENGTH: 10
<212> TYPE: PRT
<213> ORGANISM: Homo sapiens

<400> SEQUENCE: 184

Gly Thr Tyr Ala Pro Ala Glu Val Pro Lys
1               5                   10

<210> SEQ ID NO 185
<211> LENGTH: 9
<212> TYPE: PRT
<213> ORGANISM: Homo sapiens

<400> SEQUENCE: 185

Gly Thr Met Thr Gly Met Leu Tyr Lys
1               5

<210> SEQ ID NO 186
<211> LENGTH: 9
<212> TYPE: PRT
<213> ORGANISM: Homo sapiens

<400> SEQUENCE: 186

Ser Leu Ala Glu Ile Leu Leu Lys Lys
1               5

<210> SEQ ID NO 187
<211> LENGTH: 9
<212> TYPE: PRT
<213> ORGANISM: Homo sapiens

<400> SEQUENCE: 187

Lys Leu Thr Tyr Ile Tyr Ile Gln Lys
1               5
```

```
<210> SEQ ID NO 188
<211> LENGTH: 10
<212> TYPE: PRT
<213> ORGANISM: Homo sapiens

<400> SEQUENCE: 188

Lys Leu Leu Asn Tyr Ala Pro Leu Glu Lys
1               5                   10

<210> SEQ ID NO 189
<211> LENGTH: 9
<212> TYPE: PRT
<213> ORGANISM: Homo sapiens

<400> SEQUENCE: 189

Gly Thr Leu Pro His Pro Leu Gln Arg
1               5

<210> SEQ ID NO 190
<211> LENGTH: 9
<212> TYPE: PRT
<213> ORGANISM: Homo sapiens

<400> SEQUENCE: 190

Gly Leu Tyr Glu Phe Phe Arg Ala Lys
1               5

<210> SEQ ID NO 191
<211> LENGTH: 9
<212> TYPE: PRT
<213> ORGANISM: Homo sapiens

<400> SEQUENCE: 191

Lys Glu Pro Glu Ile Asn Thr Thr Leu
1               5

<210> SEQ ID NO 192
<211> LENGTH: 9
<212> TYPE: PRT
<213> ORGANISM: Homo sapiens

<400> SEQUENCE: 192

His Ala Ser Asp Arg Ile Ile Ala Leu
1               5

<210> SEQ ID NO 193
<211> LENGTH: 9
<212> TYPE: PRT
<213> ORGANISM: Homo sapiens

<400> SEQUENCE: 193

Arg Pro Thr Leu Trp Ala Ala Ala Leu
1               5

<210> SEQ ID NO 194
<211> LENGTH: 9
<212> TYPE: PRT
<213> ORGANISM: Homo sapiens

<400> SEQUENCE: 194

Ala Pro Ser Pro Arg Pro Leu Ser Leu
1               5

<210> SEQ ID NO 195
<211> LENGTH: 10
<212> TYPE: PRT
```

<213> ORGANISM: Homo sapiens

<400> SEQUENCE: 195

Ala Ser Asp Phe Ile Thr Lys Met Asp Tyr
1               5                   10

<210> SEQ ID NO 196
<211> LENGTH: 9
<212> TYPE: PRT
<213> ORGANISM: Homo sapiens

<400> SEQUENCE: 196

Glu Glu Arg Val Ile Asn Glu Glu Tyr
1               5

<210> SEQ ID NO 197
<211> LENGTH: 10
<212> TYPE: PRT
<213> ORGANISM: Homo sapiens

<400> SEQUENCE: 197

Ala Thr Gly Ser Trp Asp Ser Phe Leu Lys
1               5                   10

<210> SEQ ID NO 198
<211> LENGTH: 9
<212> TYPE: PRT
<213> ORGANISM: Homo sapiens

<400> SEQUENCE: 198

Arg Met Phe Asp Met Gly Phe Glu Tyr
1               5

<210> SEQ ID NO 199
<211> LENGTH: 8
<212> TYPE: PRT
<213> ORGANISM: Homo sapiens

<400> SEQUENCE: 199

Ala Pro Leu Leu Arg Trp Val Leu
1               5

<210> SEQ ID NO 200
<211> LENGTH: 11
<212> TYPE: PRT
<213> ORGANISM: Homo sapiens

<400> SEQUENCE: 200

Ala Leu Arg Pro Ser Thr Ser Arg Ser Leu Tyr
1               5                   10

<210> SEQ ID NO 201
<211> LENGTH: 9
<212> TYPE: PRT
<213> ORGANISM: Homo sapiens

<400> SEQUENCE: 201

Arg Gln Ile Pro Tyr Thr Met Met Lys
1               5

<210> SEQ ID NO 202
<211> LENGTH: 9
<212> TYPE: PRT
<213> ORGANISM: Homo sapiens

<400> SEQUENCE: 202

Ala Glu Thr His Ile Val Leu Leu Phe
1               5

<210> SEQ ID NO 203
<211> LENGTH: 9
<212> TYPE: PRT
<213> ORGANISM: Homo sapiens

<400> SEQUENCE: 203

Arg Val His Ala Tyr Ile Ile Ser Tyr
1               5

<210> SEQ ID NO 204
<211> LENGTH: 11
<212> TYPE: PRT
<213> ORGANISM: Homo sapiens

<400> SEQUENCE: 204

Ala Val Ile Val Leu Val Glu Asn Phe Tyr Lys
1               5                   10

<210> SEQ ID NO 205
<211> LENGTH: 9
<212> TYPE: PRT
<213> ORGANISM: Homo sapiens

<400> SEQUENCE: 205

Ser Glu Glu Leu Leu Arg Glu His Tyr
1               5

<210> SEQ ID NO 206
<211> LENGTH: 9
<212> TYPE: PRT
<213> ORGANISM: Homo sapiens

<400> SEQUENCE: 206

Arg Ala Asp Gly Asn Phe Leu Leu Tyr
1               5

<210> SEQ ID NO 207
<211> LENGTH: 9
<212> TYPE: PRT
<213> ORGANISM: Homo sapiens

<400> SEQUENCE: 207

Ser Glu Phe Thr Gly Val Trp Lys Tyr
1               5

<210> SEQ ID NO 208
<211> LENGTH: 9
<212> TYPE: PRT
<213> ORGANISM: Homo sapiens

<400> SEQUENCE: 208

Ser Ile Asp Arg Thr Val Met Tyr Tyr
1               5

<210> SEQ ID NO 209
<211> LENGTH: 11
<212> TYPE: PRT
<213> ORGANISM: Homo sapiens

<400> SEQUENCE: 209

Glu Thr Asp Leu Leu Asp Ile Arg Ser Glu Tyr
1               5                   10

<210> SEQ ID NO 210
<211> LENGTH: 9
<212> TYPE: PRT
<213> ORGANISM: Homo sapiens

<400> SEQUENCE: 210

Glu Ser Tyr Glu Ala Leu Pro Gln His
1               5

<210> SEQ ID NO 211
<211> LENGTH: 9
<212> TYPE: PRT
<213> ORGANISM: Homo sapiens

<400> SEQUENCE: 211

Ser Glu Glu Glu Ile Arg Glu Ala Phe
1               5

<210> SEQ ID NO 212
<211> LENGTH: 9
<212> TYPE: PRT
<213> ORGANISM: Homo sapiens

<400> SEQUENCE: 212

Lys Val Met Gln Gln Asn Leu Val Tyr
1               5

<210> SEQ ID NO 213
<211> LENGTH: 8
<212> TYPE: PRT
<213> ORGANISM: Homo sapiens

<400> SEQUENCE: 213

Asp Glu Lys Ser Ile Ile Thr Tyr
1               5

<210> SEQ ID NO 214
<211> LENGTH: 8
<212> TYPE: PRT
<213> ORGANISM: Homo sapiens

<400> SEQUENCE: 214

Glu Glu Ile Glu Gly Phe Arg Tyr
1               5

<210> SEQ ID NO 215
<211> LENGTH: 9
<212> TYPE: PRT
<213> ORGANISM: Homo sapiens

<400> SEQUENCE: 215

Met Glu Asn Leu Phe Ile Asn Arg Phe
1               5

<210> SEQ ID NO 216
<211> LENGTH: 9
<212> TYPE: PRT
<213> ORGANISM: Homo sapiens

<400> SEQUENCE: 216

Met Glu Lys Ile Trp His His Thr Phe
1               5

<210> SEQ ID NO 217

```
<211> LENGTH: 10
<212> TYPE: PRT
<213> ORGANISM: Homo sapiens

<400> SEQUENCE: 217

Met Glu His Ala Met Glu Thr Met Met Phe
1               5                   10

<210> SEQ ID NO 218
<211> LENGTH: 8
<212> TYPE: PRT
<213> ORGANISM: Homo sapiens

<400> SEQUENCE: 218

Glu Glu Ile Phe Asn Leu Lys Phe
1               5

<210> SEQ ID NO 219
<211> LENGTH: 9
<212> TYPE: PRT
<213> ORGANISM: Homo sapiens

<400> SEQUENCE: 219

Leu Val Leu Met Val Leu Tyr Leu Ile
1               5

<210> SEQ ID NO 220
<211> LENGTH: 9
<212> TYPE: PRT
<213> ORGANISM: Homo sapiens

<400> SEQUENCE: 220

Glu Glu Leu Gln Gln Lys Val Ser Tyr
1               5

<210> SEQ ID NO 221
<211> LENGTH: 11
<212> TYPE: PRT
<213> ORGANISM: Homo sapiens

<400> SEQUENCE: 221

Leu Arg Val Ala Pro Glu Glu His Pro Val Leu
1               5                   10

<210> SEQ ID NO 222
<211> LENGTH: 9
<212> TYPE: PRT
<213> ORGANISM: Homo sapiens

<400> SEQUENCE: 222

Asp Gly His Leu Phe Gln Val Glu Tyr
1               5

<210> SEQ ID NO 223
<211> LENGTH: 9
<212> TYPE: PRT
<213> ORGANISM: Homo sapiens

<400> SEQUENCE: 223

Leu Ala Glu Leu Ala His Arg Glu Tyr
1               5

<210> SEQ ID NO 224
<211> LENGTH: 10
<212> TYPE: PRT
<213> ORGANISM: Homo sapiens
```

```
<400> SEQUENCE: 224

Asn Glu Ala Asp Val His Gly Ile Tyr Phe
1               5                   10

<210> SEQ ID NO 225
<211> LENGTH: 9
<212> TYPE: PRT
<213> ORGANISM: Homo sapiens

<400> SEQUENCE: 225

Lys Val Phe Gln Glu Pro Leu Phe Tyr
1               5

<210> SEQ ID NO 226
<211> LENGTH: 9
<212> TYPE: PRT
<213> ORGANISM: Homo sapiens

<400> SEQUENCE: 226

Gly Val Leu Ala Trp Val Lys Glu Lys
1               5

<210> SEQ ID NO 227
<211> LENGTH: 9
<212> TYPE: PRT
<213> ORGANISM: Homo sapiens

<400> SEQUENCE: 227

His Glu Ala Leu Leu Tyr Tyr Val Leu
1               5

<210> SEQ ID NO 228
<211> LENGTH: 8
<212> TYPE: PRT
<213> ORGANISM: Homo sapiens

<400> SEQUENCE: 228

His Glu Met Ile Ile Leu Lys Leu
1               5

<210> SEQ ID NO 229
<211> LENGTH: 9
<212> TYPE: PRT
<213> ORGANISM: Homo sapiens

<400> SEQUENCE: 229

Ile Val Pro Ala Asn Phe Pro Ser Leu
1               5

<210> SEQ ID NO 230
<211> LENGTH: 9
<212> TYPE: PRT
<213> ORGANISM: Homo sapiens

<400> SEQUENCE: 230

His Leu Asp Leu Gly Ile Leu Tyr Tyr
1               5

<210> SEQ ID NO 231
<211> LENGTH: 10
<212> TYPE: PRT
<213> ORGANISM: Homo sapiens

<400> SEQUENCE: 231
```

```
Ile Thr Asp Ser Ala Gly His Ile Leu Tyr
1               5                   10

<210> SEQ ID NO 232
<211> LENGTH: 10
<212> TYPE: PRT
<213> ORGANISM: Homo sapiens

<400> SEQUENCE: 232

His Thr Asp Asp Pro Leu Thr Trp Asp Tyr
1               5                   10

<210> SEQ ID NO 233
<211> LENGTH: 9
<212> TYPE: PRT
<213> ORGANISM: Homo sapiens

<400> SEQUENCE: 233

Ile Ala Arg Asn Leu Thr Gln Gln Leu
1               5

<210> SEQ ID NO 234
<211> LENGTH: 9
<212> TYPE: PRT
<213> ORGANISM: Homo sapiens

<400> SEQUENCE: 234

Ile Asp Gln Thr Ala Leu Ala Val Tyr
1               5

<210> SEQ ID NO 235
<211> LENGTH: 9
<212> TYPE: PRT
<213> ORGANISM: Homo sapiens

<400> SEQUENCE: 235

Leu Glu Asp Val Val Ile Glu Arg Tyr
1               5

<210> SEQ ID NO 236
<211> LENGTH: 9
<212> TYPE: PRT
<213> ORGANISM: Homo sapiens

<400> SEQUENCE: 236

Gln Ile Ala Ser Phe Ile Leu Leu Arg
1               5

<210> SEQ ID NO 237
<211> LENGTH: 8
<212> TYPE: PRT
<213> ORGANISM: Homo sapiens

<400> SEQUENCE: 237

Asp Glu His Tyr Ile Leu Thr Phe
1               5

<210> SEQ ID NO 238
<211> LENGTH: 10
<212> TYPE: PRT
<213> ORGANISM: Homo sapiens

<400> SEQUENCE: 238

Asp Glu Ile Gly Leu Pro Lys Ile Phe Tyr
1               5                   10
```

<210> SEQ ID NO 239
<211> LENGTH: 9
<212> TYPE: PRT
<213> ORGANISM: Homo sapiens

<400> SEQUENCE: 239

Asp Glu Ile Val Arg Ile Asn Gly Tyr
1               5

<210> SEQ ID NO 240
<211> LENGTH: 9
<212> TYPE: PRT
<213> ORGANISM: Homo sapiens

<400> SEQUENCE: 240

Asp Glu Lys Leu Leu Tyr Asp Thr Phe
1               5

<210> SEQ ID NO 241
<211> LENGTH: 10
<212> TYPE: PRT
<213> ORGANISM: Homo sapiens

<400> SEQUENCE: 241

Arg Ile Ile Glu Glu Thr Leu Ala Leu Lys
1               5                   10

<210> SEQ ID NO 242
<211> LENGTH: 9
<212> TYPE: PRT
<213> ORGANISM: Homo sapiens

<400> SEQUENCE: 242

Gly Thr Asp Glu Leu Arg Leu Leu Tyr
1               5

<210> SEQ ID NO 243
<211> LENGTH: 11
<212> TYPE: PRT
<213> ORGANISM: Homo sapiens

<400> SEQUENCE: 243

Asp Glu Leu Glu Ile Ile Glu Gly Met Lys Phe
1               5                   10

<210> SEQ ID NO 244
<211> LENGTH: 10
<212> TYPE: PRT
<213> ORGANISM: Homo sapiens

<400> SEQUENCE: 244

Gln Val Asp Pro Leu Ser Ala Leu Lys Tyr
1               5                   10

<210> SEQ ID NO 245
<211> LENGTH: 9
<212> TYPE: PRT
<213> ORGANISM: Homo sapiens

<400> SEQUENCE: 245

Asp Glu Leu His Tyr Leu Glu Val Tyr
1               5

<210> SEQ ID NO 246
<211> LENGTH: 10

<212> TYPE: PRT
<213> ORGANISM: Homo sapiens

<400> SEQUENCE: 246

Glu Glu Phe Glu Leu Leu Gly Lys Ala Tyr
1               5                   10

<210> SEQ ID NO 247
<211> LENGTH: 11
<212> TYPE: PRT
<213> ORGANISM: Homo sapiens

<400> SEQUENCE: 247

Gln Leu Glu Asp Gly Arg Thr Leu Ser Asp Tyr
1               5                   10

<210> SEQ ID NO 248
<211> LENGTH: 9
<212> TYPE: PRT
<213> ORGANISM: Homo sapiens

<400> SEQUENCE: 248

Asp Glu Phe Leu Trp Arg Glu Gln Phe
1               5

<210> SEQ ID NO 249
<211> LENGTH: 8
<212> TYPE: PRT
<213> ORGANISM: Homo sapiens

<400> SEQUENCE: 249

Asp Glu Met Leu Ser Arg Gly Phe
1               5

<210> SEQ ID NO 250
<211> LENGTH: 10
<212> TYPE: PRT
<213> ORGANISM: Homo sapiens

<400> SEQUENCE: 250

Asp Glu Pro Leu Leu Lys His Trp Glu Phe
1               5                   10

<210> SEQ ID NO 251
<211> LENGTH: 10
<212> TYPE: PRT
<213> ORGANISM: Homo sapiens

<400> SEQUENCE: 251

Pro Ser Arg Asp Ser Leu Pro Leu Pro Val
1               5                   10

<210> SEQ ID NO 252
<211> LENGTH: 11
<212> TYPE: PRT
<213> ORGANISM: Homo sapiens

<400> SEQUENCE: 252

Asn Leu Arg Glu Thr Asn Leu Asp Ser Leu Pro
1               5                   10

<210> SEQ ID NO 253
<211> LENGTH: 9
<212> TYPE: PRT
<213> ORGANISM: Homo sapiens

```
<400> SEQUENCE: 253

Asp Glu Val Lys Phe Leu Thr Val Leu
1               5

<210> SEQ ID NO 254
<211> LENGTH: 9
<212> TYPE: PRT
<213> ORGANISM: Homo sapiens

<400> SEQUENCE: 254

Asn Glu Val Glu Lys Thr Met Glu Tyr
1               5

<210> SEQ ID NO 255
<211> LENGTH: 10
<212> TYPE: PRT
<213> ORGANISM: Homo sapiens

<400> SEQUENCE: 255

Asp Glu Val Gln Val Val Arg Gly His Tyr
1               5                   10

<210> SEQ ID NO 256
<211> LENGTH: 9
<212> TYPE: PRT
<213> ORGANISM: Homo sapiens

<400> SEQUENCE: 256

Asp Glu Trp Leu Lys Pro Glu Leu Phe
1               5

<210> SEQ ID NO 257
<211> LENGTH: 9
<212> TYPE: PRT
<213> ORGANISM: Homo sapiens

<400> SEQUENCE: 257

Asp Glu Tyr Ser Leu Val Arg Glu Leu
1               5

<210> SEQ ID NO 258
<211> LENGTH: 9
<212> TYPE: PRT
<213> ORGANISM: Homo sapiens

<400> SEQUENCE: 258

Asn Glu Phe Glu Ala Thr Gln Lys Leu
1               5

<210> SEQ ID NO 259
<211> LENGTH: 9
<212> TYPE: PRT
<213> ORGANISM: Homo sapiens

<400> SEQUENCE: 259

Asp Glu Leu Gln Gln Pro Leu Glu Leu
1               5

<210> SEQ ID NO 260
<211> LENGTH: 11
<212> TYPE: PRT
<213> ORGANISM: Homo sapiens

<400> SEQUENCE: 260

Asp Val Val Met Thr Gln Ser Pro Leu Ser Leu
```

```
1               5                  10

<210> SEQ ID NO 261
<211> LENGTH: 9
<212> TYPE: PRT
<213> ORGANISM: Homo sapiens

<400> SEQUENCE: 261

Ser Glu Arg Glu Ala Ile Glu Val Phe
1               5

<210> SEQ ID NO 262
<211> LENGTH: 9
<212> TYPE: PRT
<213> ORGANISM: Homo sapiens

<400> SEQUENCE: 262

Arg Tyr Phe Tyr His Gln Glu Glu Tyr
1               5

<210> SEQ ID NO 263
<211> LENGTH: 9
<212> TYPE: PRT
<213> ORGANISM: Homo sapiens

<400> SEQUENCE: 263

Thr Ser Ala Leu Pro Ile Ile Gln Lys
1               5

<210> SEQ ID NO 264
<211> LENGTH: 11
<212> TYPE: PRT
<213> ORGANISM: Homo sapiens

<400> SEQUENCE: 264

Arg Val Gln Glu Ala Val Glu Ser Met Val Lys
1               5                  10

<210> SEQ ID NO 265
<211> LENGTH: 11
<212> TYPE: PRT
<213> ORGANISM: Homo sapiens

<400> SEQUENCE: 265

Thr Val Met Glu Leu Val Lys Ile Ile Tyr Lys
1               5                  10

<210> SEQ ID NO 266
<211> LENGTH: 9
<212> TYPE: PRT
<213> ORGANISM: Homo sapiens

<400> SEQUENCE: 266

Arg Leu Leu Gln Lys Val Leu Ala Tyr
1               5

<210> SEQ ID NO 267
<211> LENGTH: 9
<212> TYPE: PRT
<213> ORGANISM: Homo sapiens

<400> SEQUENCE: 267

Arg Ile His Phe Pro Leu Ala Thr Tyr
1               5
```

```
<210> SEQ ID NO 268
<211> LENGTH: 12
<212> TYPE: PRT
<213> ORGANISM: Homo sapiens

<400> SEQUENCE: 268

Val Gly Gly Leu Lys Asn Thr Leu Val His Arg Leu
1               5                   10

<210> SEQ ID NO 269
<211> LENGTH: 10
<212> TYPE: PRT
<213> ORGANISM: Homo sapiens

<400> SEQUENCE: 269

Gln Ala Gln Ala Asp Ser Leu Thr Val Tyr
1               5                   10

<210> SEQ ID NO 270
<211> LENGTH: 9
<212> TYPE: PRT
<213> ORGANISM: Homo sapiens

<400> SEQUENCE: 270

Val Leu Asp Pro Tyr Leu Leu Lys Tyr
1               5

<210> SEQ ID NO 271
<211> LENGTH: 10
<212> TYPE: PRT
<213> ORGANISM: Homo sapiens

<400> SEQUENCE: 271

Ile Phe Ser Pro Pro Phe Pro Leu Phe Tyr
1               5                   10

<210> SEQ ID NO 272
<211> LENGTH: 9
<212> TYPE: PRT
<213> ORGANISM: Homo sapiens

<400> SEQUENCE: 272

Thr Glu Leu Leu Leu Lys Glu Gly Phe
1               5

<210> SEQ ID NO 273
<211> LENGTH: 12
<212> TYPE: PRT
<213> ORGANISM: Homo sapiens

<400> SEQUENCE: 273

Gly Leu Phe Glu Val Gly Ala Gly Trp Ile Gly Lys
1               5                   10

<210> SEQ ID NO 274
<211> LENGTH: 9
<212> TYPE: PRT
<213> ORGANISM: Homo sapiens

<400> SEQUENCE: 274

Tyr Glu Tyr Lys Phe Gly Phe Glu Leu
1               5

<210> SEQ ID NO 275
<211> LENGTH: 9
<212> TYPE: PRT
```

```
<213> ORGANISM: Homo sapiens

<400> SEQUENCE: 275

Trp Pro Leu Trp Arg Leu Val Ser Leu
1               5

<210> SEQ ID NO 276
<211> LENGTH: 9
<212> TYPE: PRT
<213> ORGANISM: Homo sapiens

<400> SEQUENCE: 276

Tyr Ile Asp Glu Gln Phe Glu Arg Tyr
1               5

<210> SEQ ID NO 277
<211> LENGTH: 11
<212> TYPE: PRT
<213> ORGANISM: Homo sapiens

<400> SEQUENCE: 277

Tyr Leu Asp Glu Lys Leu Ala Leu Leu Asn Ala
1               5                   10

<210> SEQ ID NO 278
<211> LENGTH: 8
<212> TYPE: PRT
<213> ORGANISM: Homo sapiens

<400> SEQUENCE: 278

Asp Glu His Leu Ile Thr Phe Phe
1               5

<210> SEQ ID NO 279
<211> LENGTH: 8
<212> TYPE: PRT
<213> ORGANISM: Homo sapiens

<400> SEQUENCE: 279

Asp Asp Phe His Ile Tyr Val Tyr
1               5

<210> SEQ ID NO 280
<211> LENGTH: 9
<212> TYPE: PRT
<213> ORGANISM: Homo sapiens

<400> SEQUENCE: 280

Ala Pro Arg Thr Val Leu Leu Leu Leu
1               5

<210> SEQ ID NO 281
<211> LENGTH: 11
<212> TYPE: PRT
<213> ORGANISM: Homo sapiens

<400> SEQUENCE: 281

Ala Pro Arg Thr Val Ala Leu Thr Ala Leu Leu
1               5                   10

<210> SEQ ID NO 282
<211> LENGTH: 10
<212> TYPE: PRT
<213> ORGANISM: Homo sapiens

<400> SEQUENCE: 282
```

```
Phe Thr Asp Val Asn Ser Ile Leu Arg Tyr
1               5                   10
```

<210> SEQ ID NO 283
<211> LENGTH: 9
<212> TYPE: PRT
<213> ORGANISM: Homo sapiens

<400> SEQUENCE: 283

```
Tyr Ser Glu Glu Glu Cys Arg Gln Tyr
1               5
```

<210> SEQ ID NO 284
<211> LENGTH: 9
<212> TYPE: PRT
<213> ORGANISM: Homo sapiens

<400> SEQUENCE: 284

```
Tyr Ser Glu Lys Ile Val Asp Met Tyr
1               5
```

<210> SEQ ID NO 285
<211> LENGTH: 10
<212> TYPE: PRT
<213> ORGANISM: Homo sapiens

<400> SEQUENCE: 285

```
Tyr Thr Asp Leu Leu Arg Leu Phe Glu Tyr
1               5                   10
```

<210> SEQ ID NO 286
<211> LENGTH: 9
<212> TYPE: PRT
<213> ORGANISM: Homo sapiens

<400> SEQUENCE: 286

```
Tyr Val Asp Pro Gln Phe Leu Thr Tyr
1               5
```

<210> SEQ ID NO 287
<211> LENGTH: 9
<212> TYPE: PRT
<213> ORGANISM: Homo sapiens

<400> SEQUENCE: 287

```
His Glu Arg Thr Phe Leu Leu Glu Tyr
1               5
```

<210> SEQ ID NO 288
<211> LENGTH: 17
<212> TYPE: PRT
<213> ORGANISM: Homo sapiens

<400> SEQUENCE: 288

```
Ser Ser Val Pro Gly Val Arg Leu Leu Gln Asp Ser Val Asp Phe Ser
1               5                   10                  15

Leu
```

<210> SEQ ID NO 289
<211> LENGTH: 12
<212> TYPE: PRT
<213> ORGANISM: Homo sapiens

<400> SEQUENCE: 289

```
Ser Leu Leu Thr Ser Ser Lys Gly Gln Leu Gln Lys
1               5                   10
```

<210> SEQ ID NO 290
<211> LENGTH: 10
<212> TYPE: PRT
<213> ORGANISM: Homo sapiens

<400> SEQUENCE: 290

```
Ser Pro Arg Glu Asn Ile Leu Val Ser Leu
1               5                   10
```

<210> SEQ ID NO 291
<211> LENGTH: 11
<212> TYPE: PRT
<213> ORGANISM: Homo sapiens

<400> SEQUENCE: 291

```
Asp Glu Val Asp Ile Lys Ser Arg Ala Ala Tyr
1               5                   10
```

<210> SEQ ID NO 292
<211> LENGTH: 9
<212> TYPE: PRT
<213> ORGANISM: Homo sapiens

<400> SEQUENCE: 292

```
Thr Ser Pro Ser Gln Ser Leu Phe Tyr
1               5
```

<210> SEQ ID NO 293
<211> LENGTH: 10
<212> TYPE: PRT
<213> ORGANISM: Homo sapiens

<400> SEQUENCE: 293

```
Tyr Thr Glu Thr Glu Pro Tyr His Asn Tyr
1               5                   10
```

<210> SEQ ID NO 294
<211> LENGTH: 15
<212> TYPE: PRT
<213> ORGANISM: Homo sapiens

<400> SEQUENCE: 294

```
Ser Ser Val Pro Gly Val Arg Leu Leu Gln Asp Ser Val Asp Phe
1               5                   10                  15
```

<210> SEQ ID NO 295
<211> LENGTH: 9
<212> TYPE: PRT
<213> ORGANISM: Homo sapiens

<400> SEQUENCE: 295

```
Val Ala Leu Ile Ser Pro Lys Asp Ile
1               5
```

<210> SEQ ID NO 296
<211> LENGTH: 10
<212> TYPE: PRT
<213> ORGANISM: Homo sapiens

<400> SEQUENCE: 296

```
Ser Thr Asp Lys Ala Glu Tyr Thr Phe Tyr
1               5                   10
```

```
<210> SEQ ID NO 297
<211> LENGTH: 9
<212> TYPE: PRT
<213> ORGANISM: Homo sapiens

<400> SEQUENCE: 297

Val Thr Glu Ile Phe Arg Gln Ala Phe
1               5

<210> SEQ ID NO 298
<211> LENGTH: 9
<212> TYPE: PRT
<213> ORGANISM: Homo sapiens

<400> SEQUENCE: 298

Ser Val Leu Ser Pro Leu Leu Asn Lys
1               5

<210> SEQ ID NO 299
<211> LENGTH: 10
<212> TYPE: PRT
<213> ORGANISM: Homo sapiens

<400> SEQUENCE: 299

Arg Ala Phe Ser Ser Leu Gly Leu Leu Lys
1               5                   10

<210> SEQ ID NO 300
<211> LENGTH: 10
<212> TYPE: PRT
<213> ORGANISM: Homo sapiens

<400> SEQUENCE: 300

Phe Ser Lys Leu Arg Pro Leu Ile Ser Lys
1               5                   10

<210> SEQ ID NO 301
<211> LENGTH: 9
<212> TYPE: PRT
<213> ORGANISM: Homo sapiens

<400> SEQUENCE: 301

Arg Thr Phe Thr Trp Leu Val Gly Lys
1               5

<210> SEQ ID NO 302
<211> LENGTH: 9
<212> TYPE: PRT
<213> ORGANISM: Homo sapiens

<400> SEQUENCE: 302

Lys Val Ala Asn Ile Ile Leu Ser Tyr
1               5

<210> SEQ ID NO 303
<211> LENGTH: 9
<212> TYPE: PRT
<213> ORGANISM: Homo sapiens

<400> SEQUENCE: 303

Thr Met Leu Ala Arg Leu Ala Ser Ala
1               5

<210> SEQ ID NO 304
<211> LENGTH: 9
```

```
<212> TYPE: PRT
<213> ORGANISM: Homo sapiens

<400> SEQUENCE: 304

His Glu Leu Pro Leu Pro His Ser Val
1               5

<210> SEQ ID NO 305
<211> LENGTH: 9
<212> TYPE: PRT
<213> ORGANISM: Homo sapiens

<400> SEQUENCE: 305

Ala Val Gln Arg Thr Leu Leu Glu Lys
1               5

<210> SEQ ID NO 306
<211> LENGTH: 13
<212> TYPE: PRT
<213> ORGANISM: Homo sapiens

<400> SEQUENCE: 306

Glu Thr Arg Pro Ala Gly Asp Gly Thr Phe Gln Lys Trp
1               5                   10

<210> SEQ ID NO 307
<211> LENGTH: 12
<212> TYPE: PRT
<213> ORGANISM: Homo sapiens

<400> SEQUENCE: 307

Ala Val Leu Ser Ile Leu Pro Ala Ile Phe Gln Lys
1               5                   10

<210> SEQ ID NO 308
<211> LENGTH: 9
<212> TYPE: PRT
<213> ORGANISM: Homo sapiens

<400> SEQUENCE: 308

Glu Ile Ala Gly His Ile Met Glu Phe
1               5

<210> SEQ ID NO 309
<211> LENGTH: 9
<212> TYPE: PRT
<213> ORGANISM: Homo sapiens

<400> SEQUENCE: 309

Glu Leu Ile Arg Thr Ile Met Gly Trp
1               5

<210> SEQ ID NO 310
<211> LENGTH: 10
<212> TYPE: PRT
<213> ORGANISM: Homo sapiens

<400> SEQUENCE: 310

Glu Val Phe Pro Leu Lys Val Phe Gly Tyr
1               5                   10

<210> SEQ ID NO 311
<211> LENGTH: 10
<212> TYPE: PRT
<213> ORGANISM: Homo sapiens
```

```
<400> SEQUENCE: 311

Ala Thr Pro Thr Ser Pro Ile Arg Val Lys
1               5                   10

<210> SEQ ID NO 312
<211> LENGTH: 10
<212> TYPE: PRT
<213> ORGANISM: Homo sapiens

<400> SEQUENCE: 312

Ala Val Leu Tyr Gln Pro Leu Phe Asp Lys
1               5                   10

<210> SEQ ID NO 313
<211> LENGTH: 10
<212> TYPE: PRT
<213> ORGANISM: Homo sapiens

<400> SEQUENCE: 313

Glu Val Val Asp Phe Ile Gln Ser Lys Ile
1               5                   10

<210> SEQ ID NO 314
<211> LENGTH: 11
<212> TYPE: PRT
<213> ORGANISM: Homo sapiens

<400> SEQUENCE: 314

Ala Val Gln Glu Phe Gly Leu Ala Arg Phe Lys
1               5                   10

<210> SEQ ID NO 315
<211> LENGTH: 9
<212> TYPE: PRT
<213> ORGANISM: Homo sapiens

<400> SEQUENCE: 315

Glu Ala Ile Gln Asp Leu Trp Gln Trp
1               5

<210> SEQ ID NO 316
<211> LENGTH: 9
<212> TYPE: PRT
<213> ORGANISM: Homo sapiens

<400> SEQUENCE: 316

Gly Val Ile Arg Ser Leu Met Ala Phe
1               5

<210> SEQ ID NO 317
<211> LENGTH: 10
<212> TYPE: PRT
<213> ORGANISM: Homo sapiens

<400> SEQUENCE: 317

His Ile Ile Ser Gly Thr Cys Ala Ser Trp
1               5                   10

<210> SEQ ID NO 318
<211> LENGTH: 10
<212> TYPE: PRT
<213> ORGANISM: Homo sapiens

<400> SEQUENCE: 318

Gly Val Ile Asp Val Ile Thr Lys Thr Trp
```

-continued

```
<210> SEQ ID NO 319
<211> LENGTH: 9
<212> TYPE: PRT
<213> ORGANISM: Homo sapiens

<400> SEQUENCE: 319

Gly Val Ile Asp Leu Ile Phe Glu Lys
1               5

<210> SEQ ID NO 320
<211> LENGTH: 9
<212> TYPE: PRT
<213> ORGANISM: Homo sapiens

<400> SEQUENCE: 320

Gly Val Cys His Ile Phe Ala Ser Phe
1               5

<210> SEQ ID NO 321
<211> LENGTH: 9
<212> TYPE: PRT
<213> ORGANISM: Homo sapiens

<400> SEQUENCE: 321

Gly Thr Tyr Val Ser Ser Val Pro Arg
1               5

<210> SEQ ID NO 322
<211> LENGTH: 11
<212> TYPE: PRT
<213> ORGANISM: Homo sapiens

<400> SEQUENCE: 322

Gly Thr Ala Gly Leu Leu Glu Gln Trp Leu Lys
1               5                   10

<210> SEQ ID NO 323
<211> LENGTH: 10
<212> TYPE: PRT
<213> ORGANISM: Homo sapiens

<400> SEQUENCE: 323

His Val Ile Thr Gly Leu Leu Glu His Tyr
1               5                   10

<210> SEQ ID NO 324
<211> LENGTH: 11
<212> TYPE: PRT
<213> ORGANISM: Homo sapiens

<400> SEQUENCE: 324

Gly Thr Ala Asp Glu Leu Val Leu His Ser Trp
1               5                   10

<210> SEQ ID NO 325
<211> LENGTH: 9
<212> TYPE: PRT
<213> ORGANISM: Homo sapiens

<400> SEQUENCE: 325

Glu Ile Lys Glu Val Ile Leu Glu Phe
1               5
```

```
<210> SEQ ID NO 326
<211> LENGTH: 9
<212> TYPE: PRT
<213> ORGANISM: Homo sapiens

<400> SEQUENCE: 326

Glu Glu Ala Ser Leu Leu His Gln Phe
1               5

<210> SEQ ID NO 327
<211> LENGTH: 9
<212> TYPE: PRT
<213> ORGANISM: Homo sapiens

<400> SEQUENCE: 327

Lys Leu Phe Ile Gly Gly Leu Ser Phe
1               5

<210> SEQ ID NO 328
<211> LENGTH: 9
<212> TYPE: PRT
<213> ORGANISM: Homo sapiens

<400> SEQUENCE: 328

Asp Val Val Pro Ala Val Arg Lys Trp
1               5

<210> SEQ ID NO 329
<211> LENGTH: 9
<212> TYPE: PRT
<213> ORGANISM: Homo sapiens

<400> SEQUENCE: 329

Asp Val Thr Gly Val Val Arg Gln Trp
1               5

<210> SEQ ID NO 330
<211> LENGTH: 9
<212> TYPE: PRT
<213> ORGANISM: Homo sapiens

<400> SEQUENCE: 330

Asp Val Lys Asp Tyr Ile Gln Glu Tyr
1               5

<210> SEQ ID NO 331
<211> LENGTH: 11
<212> TYPE: PRT
<213> ORGANISM: Homo sapiens

<400> SEQUENCE: 331

Asp Val Ile Asp Asn Asp Ser Trp Arg Leu Trp
1               5                   10

<210> SEQ ID NO 332
<211> LENGTH: 11
<212> TYPE: PRT
<213> ORGANISM: Homo sapiens

<400> SEQUENCE: 332

Asp Val Phe Ser Ser Lys Gly Met Thr Arg Trp
1               5                   10

<210> SEQ ID NO 333
<211> LENGTH: 9
<212> TYPE: PRT
```

-continued

<213> ORGANISM: Homo sapiens

<400> SEQUENCE: 333

Asp Thr Val Lys Lys Ile Glu Ser Phe
1               5

<210> SEQ ID NO 334
<211> LENGTH: 11
<212> TYPE: PRT
<213> ORGANISM: Homo sapiens

<400> SEQUENCE: 334

Asp Leu Pro Ser Asn His Val Ile Asp Arg Trp
1               5                   10

<210> SEQ ID NO 335
<211> LENGTH: 9
<212> TYPE: PRT
<213> ORGANISM: Homo sapiens

<400> SEQUENCE: 335

Asp Leu Ile Gly His Ile Val Glu Phe
1               5

<210> SEQ ID NO 336
<211> LENGTH: 9
<212> TYPE: PRT
<213> ORGANISM: Homo sapiens

<400> SEQUENCE: 336

Asp Lys Glu Ser Gln Leu Glu Ala Tyr
1               5

<210> SEQ ID NO 337
<211> LENGTH: 11
<212> TYPE: PRT
<213> ORGANISM: Homo sapiens

<400> SEQUENCE: 337

Glu Val Ile Lys Leu Lys Gly Tyr Thr Ser Trp
1               5                   10

<210> SEQ ID NO 338
<211> LENGTH: 9
<212> TYPE: PRT
<213> ORGANISM: Homo sapiens

<400> SEQUENCE: 338

Gly Ser Ser Asp Val Ile Ile His Arg
1               5

<210> SEQ ID NO 339
<211> LENGTH: 9
<212> TYPE: PRT
<213> ORGANISM: Homo sapiens

<400> SEQUENCE: 339

Gly Thr Leu Asp Tyr Ile Leu Gln Arg
1               5

<210> SEQ ID NO 340
<211> LENGTH: 10
<212> TYPE: PRT
<213> ORGANISM: Homo sapiens

<400> SEQUENCE: 340

Glu Val Asp Lys Arg Val His Met Thr Trp
1               5                   10

<210> SEQ ID NO 341
<211> LENGTH: 10
<212> TYPE: PRT
<213> ORGANISM: Homo sapiens

<400> SEQUENCE: 341

Ser Val Pro Tyr Phe Leu Phe Gln His Trp
1               5                   10

<210> SEQ ID NO 342
<211> LENGTH: 11
<212> TYPE: PRT
<213> ORGANISM: Homo sapiens

<400> SEQUENCE: 342

Ser Val Glu Glu Ile Ser Thr Leu Val Gln Lys
1               5                   10

<210> SEQ ID NO 343
<211> LENGTH: 10
<212> TYPE: PRT
<213> ORGANISM: Homo sapiens

<400> SEQUENCE: 343

Ser Thr Phe Gln Gln Met Trp Ile Ser Lys
1               5                   10

<210> SEQ ID NO 344
<211> LENGTH: 10
<212> TYPE: PRT
<213> ORGANISM: Homo sapiens

<400> SEQUENCE: 344

Thr Thr Ile Pro His Ala Leu Leu Thr Trp
1               5                   10

<210> SEQ ID NO 345
<211> LENGTH: 10
<212> TYPE: PRT
<213> ORGANISM: Homo sapiens

<400> SEQUENCE: 345

Ser Ala Phe Leu Leu Leu Gly Leu Phe Lys
1               5                   10

<210> SEQ ID NO 346
<211> LENGTH: 11
<212> TYPE: PRT
<213> ORGANISM: Homo sapiens

<400> SEQUENCE: 346

Asn Ile Gly Asp Glu Ala Leu Ile Gly Arg Trp
1               5                   10

<210> SEQ ID NO 347
<211> LENGTH: 10
<212> TYPE: PRT
<213> ORGANISM: Homo sapiens

<400> SEQUENCE: 347

Thr Val Ala Phe Val Pro Ile Ser Gly Trp
1               5                   10

```
<210> SEQ ID NO 348
<211> LENGTH: 10
<212> TYPE: PRT
<213> ORGANISM: Homo sapiens

<400> SEQUENCE: 348

Glu Thr Val Asn Leu Arg Ser Leu Gly Phe
1               5                   10

<210> SEQ ID NO 349
<211> LENGTH: 9
<212> TYPE: PRT
<213> ORGANISM: Homo sapiens

<400> SEQUENCE: 349

Met Pro Lys Phe Ser Met Pro Gly Phe
1               5

<210> SEQ ID NO 350
<211> LENGTH: 9
<212> TYPE: PRT
<213> ORGANISM: Homo sapiens

<400> SEQUENCE: 350

Glu Val Met Glu Ile Met Ser Arg Phe
1               5

<210> SEQ ID NO 351
<211> LENGTH: 9
<212> TYPE: PRT
<213> ORGANISM: Homo sapiens

<400> SEQUENCE: 351

Glu Val Met Asp Val Phe Leu Arg Phe
1               5

<210> SEQ ID NO 352
<211> LENGTH: 9
<212> TYPE: PRT
<213> ORGANISM: Homo sapiens

<400> SEQUENCE: 352

Arg Leu Gln Glu Ala Leu Asn Leu Phe
1               5

<210> SEQ ID NO 353
<211> LENGTH: 11
<212> TYPE: PRT
<213> ORGANISM: Homo sapiens

<400> SEQUENCE: 353

Glu Thr Ile Asp Trp Lys Val Phe Glu Ser Trp
1               5                   10

<210> SEQ ID NO 354
<211> LENGTH: 10
<212> TYPE: PRT
<213> ORGANISM: Homo sapiens

<400> SEQUENCE: 354

Glu Leu Met Glu His Gly Val Val Ser Trp
1               5                   10

<210> SEQ ID NO 355
```

```
<211> LENGTH: 9
<212> TYPE: PRT
<213> ORGANISM: Homo sapiens

<400> SEQUENCE: 355

Ala Ser Val Ala Trp Ala Val Leu Lys
1               5

<210> SEQ ID NO 356
<211> LENGTH: 9
<212> TYPE: PRT
<213> ORGANISM: Homo sapiens

<400> SEQUENCE: 356

Ser Val Ser Pro Val Val His Val Arg
1               5

<210> SEQ ID NO 357
<211> LENGTH: 10
<212> TYPE: PRT
<213> ORGANISM: Homo sapiens

<400> SEQUENCE: 357

His Val Val Asp Arg Asp Thr Glu Ala Trp
1               5                   10

<210> SEQ ID NO 358
<211> LENGTH: 9
<212> TYPE: PRT
<213> ORGANISM: Homo sapiens

<400> SEQUENCE: 358

Glu Thr Ile Thr Gly Leu Arg Val Trp
1               5

<210> SEQ ID NO 359
<211> LENGTH: 10
<212> TYPE: PRT
<213> ORGANISM: Homo sapiens

<400> SEQUENCE: 359

Arg Gln Leu Glu Asp Ile Leu Ser Thr Tyr
1               5                   10

<210> SEQ ID NO 360
<211> LENGTH: 11
<212> TYPE: PRT
<213> ORGANISM: Homo sapiens

<400> SEQUENCE: 360

Ala Ile Ala Gln Ala Glu Ser Leu Arg Tyr Lys
1               5                   10

<210> SEQ ID NO 361
<211> LENGTH: 11
<212> TYPE: PRT
<213> ORGANISM: Homo sapiens

<400> SEQUENCE: 361

Gly Val Leu Gln Leu Gly Asn Ile Val Phe Lys
1               5                   10

<210> SEQ ID NO 362
<211> LENGTH: 10
<212> TYPE: PRT
<213> ORGANISM: Homo sapiens
```

```
<400> SEQUENCE: 362

Glu Val Ile Asn Ala Leu Lys Gln Thr Trp
1               5                   10

<210> SEQ ID NO 363
<211> LENGTH: 9
<212> TYPE: PRT
<213> ORGANISM: Homo sapiens

<400> SEQUENCE: 363

Ser Thr Ala Ala Phe Phe Leu Leu Arg
1               5

<210> SEQ ID NO 364
<211> LENGTH: 10
<212> TYPE: PRT
<213> ORGANISM: Homo sapiens

<400> SEQUENCE: 364

Asp Ile Tyr Asn Phe Pro Ile His Ala Phe
1               5                   10

<210> SEQ ID NO 365
<211> LENGTH: 10
<212> TYPE: PRT
<213> ORGANISM: Homo sapiens

<400> SEQUENCE: 365

Thr Val Val Glu Arg Met Leu Ser Asn Trp
1               5                   10

<210> SEQ ID NO 366
<211> LENGTH: 11
<212> TYPE: PRT
<213> ORGANISM: Homo sapiens

<400> SEQUENCE: 366

Thr Lys Pro Trp Phe Ala Ser Gln Ile Pro Phe
1               5                   10

<210> SEQ ID NO 367
<211> LENGTH: 9
<212> TYPE: PRT
<213> ORGANISM: Homo sapiens

<400> SEQUENCE: 367

Gly Arg Val Asp Phe Ala Tyr Lys Phe
1               5

<210> SEQ ID NO 368
<211> LENGTH: 9
<212> TYPE: PRT
<213> ORGANISM: Homo sapiens

<400> SEQUENCE: 368

Gly Arg Asp Leu Thr Asp Tyr Leu Met
1               5

<210> SEQ ID NO 369
<211> LENGTH: 10
<212> TYPE: PRT
<213> ORGANISM: Homo sapiens

<400> SEQUENCE: 369
```

```
Gly Arg Ile Ser Ile Thr Gly Val Gly Phe
1               5                   10

<210> SEQ ID NO 370
<211> LENGTH: 9
<212> TYPE: PRT
<213> ORGANISM: Homo sapiens

<400> SEQUENCE: 370

Gly Arg Ile Val Thr Leu Ile Ser Phe
1               5

<210> SEQ ID NO 371
<211> LENGTH: 10
<212> TYPE: PRT
<213> ORGANISM: Homo sapiens

<400> SEQUENCE: 371

Gly Arg Leu Asp Leu Gln Tyr Ala Lys Leu
1               5                   10

<210> SEQ ID NO 372
<211> LENGTH: 9
<212> TYPE: PRT
<213> ORGANISM: Homo sapiens

<400> SEQUENCE: 372

Gly Arg Thr Asn Leu Ile Val Asn Tyr
1               5

<210> SEQ ID NO 373
<211> LENGTH: 9
<212> TYPE: PRT
<213> ORGANISM: Homo sapiens

<400> SEQUENCE: 373

Arg Tyr Phe Asp Thr Ala Val Ser Arg
1               5

<210> SEQ ID NO 374
<211> LENGTH: 9
<212> TYPE: PRT
<213> ORGANISM: Homo sapiens

<400> SEQUENCE: 374

Gly Arg Met Val Gln Val His Glu Leu
1               5

<210> SEQ ID NO 375
<211> LENGTH: 11
<212> TYPE: PRT
<213> ORGANISM: Homo sapiens

<400> SEQUENCE: 375

Phe Leu Asp Ala Ser Gly Ala Lys Leu Asp Tyr
1               5                   10

<210> SEQ ID NO 376
<211> LENGTH: 9
<212> TYPE: PRT
<213> ORGANISM: Homo sapiens

<400> SEQUENCE: 376

Ala Thr Asp Tyr His Val Arg Val Tyr
1               5
```

```
<210> SEQ ID NO 377
<211> LENGTH: 9
<212> TYPE: PRT
<213> ORGANISM: Homo sapiens

<400> SEQUENCE: 377

Ala Arg Leu Pro Trp Ala Gly Gln Leu
1               5

<210> SEQ ID NO 378
<211> LENGTH: 8
<212> TYPE: PRT
<213> ORGANISM: Homo sapiens

<400> SEQUENCE: 378

Tyr Gly Met Pro Arg Gln Ile Leu
1               5

<210> SEQ ID NO 379
<211> LENGTH: 9
<212> TYPE: PRT
<213> ORGANISM: Homo sapiens

<400> SEQUENCE: 379

Gly Arg Leu Leu Val Ala Thr Thr Phe
1               5

<210> SEQ ID NO 380
<211> LENGTH: 9
<212> TYPE: PRT
<213> ORGANISM: Homo sapiens

<400> SEQUENCE: 380

Ala Gly Gly Asp Trp Phe Thr Ser Arg
1               5

<210> SEQ ID NO 381
<211> LENGTH: 10
<212> TYPE: PRT
<213> ORGANISM: Homo sapiens

<400> SEQUENCE: 381

Gly Arg Ala Pro Ile Ser Asn Pro Gly Met
1               5                   10

<210> SEQ ID NO 382
<211> LENGTH: 10
<212> TYPE: PRT
<213> ORGANISM: Homo sapiens

<400> SEQUENCE: 382

Gly Arg Met Glu Asn Leu Ala Ser Tyr Arg
1               5                   10

<210> SEQ ID NO 383
<211> LENGTH: 9
<212> TYPE: PRT
<213> ORGANISM: Homo sapiens

<400> SEQUENCE: 383

Val Leu Pro Lys Ser Arg Val Glu Leu
1               5

<210> SEQ ID NO 384
<211> LENGTH: 9
```

```
<212> TYPE: PRT
<213> ORGANISM: Homo sapiens

<400> SEQUENCE: 384

Asp Ala Lys Ile Arg Ile Phe Asp Leu
1               5

<210> SEQ ID NO 385
<211> LENGTH: 10
<212> TYPE: PRT
<213> ORGANISM: Homo sapiens

<400> SEQUENCE: 385

Gly Arg Ala Met Val Ala Arg Leu Gly Leu
1               5                   10

<210> SEQ ID NO 386
<211> LENGTH: 9
<212> TYPE: PRT
<213> ORGANISM: Homo sapiens

<400> SEQUENCE: 386

Phe Ile Asp Ala Ser Arg Leu Val Tyr
1               5

<210> SEQ ID NO 387
<211> LENGTH: 9
<212> TYPE: PRT
<213> ORGANISM: Homo sapiens

<400> SEQUENCE: 387

Asp Pro Met Lys Ala Arg Val Val Leu
1               5

<210> SEQ ID NO 388
<211> LENGTH: 9
<212> TYPE: PRT
<213> ORGANISM: Homo sapiens

<400> SEQUENCE: 388

Phe Arg Phe Asp Pro Gln Phe Ala Leu
1               5

<210> SEQ ID NO 389
<211> LENGTH: 9
<212> TYPE: PRT
<213> ORGANISM: Homo sapiens

<400> SEQUENCE: 389

Asp Thr Asp His Tyr Phe Leu Arg Tyr
1               5

<210> SEQ ID NO 390
<211> LENGTH: 9
<212> TYPE: PRT
<213> ORGANISM: Homo sapiens

<400> SEQUENCE: 390

Glu Leu Leu Ile Arg Lys Leu Pro Phe
1               5

<210> SEQ ID NO 391
<211> LENGTH: 8
<212> TYPE: PRT
<213> ORGANISM: Homo sapiens
```

```
<400> SEQUENCE: 391

Glu Ala Phe Val Arg His Ile Leu
1               5

<210> SEQ ID NO 392
<211> LENGTH: 9
<212> TYPE: PRT
<213> ORGANISM: Homo sapiens

<400> SEQUENCE: 392

Arg Tyr Phe Asp Thr Ala Met Ser Arg
1               5

<210> SEQ ID NO 393
<211> LENGTH: 9
<212> TYPE: PRT
<213> ORGANISM: Homo sapiens

<400> SEQUENCE: 393

Gly Arg Val Phe Ile Ile Ser Lys Tyr
1               5

<210> SEQ ID NO 394
<211> LENGTH: 11
<212> TYPE: PRT
<213> ORGANISM: Homo sapiens

<400> SEQUENCE: 394

Thr Phe Arg Pro Ala Ala Met Leu Val Glu Arg
1               5                   10

<210> SEQ ID NO 395
<211> LENGTH: 9
<212> TYPE: PRT
<213> ORGANISM: Homo sapiens

<400> SEQUENCE: 395

Tyr Leu Leu Glu Lys Ser Arg Ala Ile
1               5

<210> SEQ ID NO 396
<211> LENGTH: 9
<212> TYPE: PRT
<213> ORGANISM: Homo sapiens

<400> SEQUENCE: 396

Leu Ser Asp Leu Gly Lys Leu Ser Tyr
1               5

<210> SEQ ID NO 397
<211> LENGTH: 9
<212> TYPE: PRT
<213> ORGANISM: Homo sapiens

<400> SEQUENCE: 397

Val Thr Asp Ser Ile Arg Asp Glu Tyr
1               5

<210> SEQ ID NO 398
<211> LENGTH: 9
<212> TYPE: PRT
<213> ORGANISM: Homo sapiens

<400> SEQUENCE: 398

Leu Thr Asp Arg Glu Leu Glu Glu Tyr
```

<210> SEQ ID NO 399
<211> LENGTH: 9
<212> TYPE: PRT
<213> ORGANISM: Homo sapiens

<400> SEQUENCE: 399

Leu Thr Asp Arg Gly Val Met Ser Tyr
1               5

<210> SEQ ID NO 400
<211> LENGTH: 9
<212> TYPE: PRT
<213> ORGANISM: Homo sapiens

<400> SEQUENCE: 400

Lys Gly Leu Ser Val Phe Leu Asn Arg
1               5

<210> SEQ ID NO 401
<211> LENGTH: 9
<212> TYPE: PRT
<213> ORGANISM: Homo sapiens

<400> SEQUENCE: 401

Val Thr Asp Asn Arg Ala Phe Gly Tyr
1               5

<210> SEQ ID NO 402
<211> LENGTH: 11
<212> TYPE: PRT
<213> ORGANISM: Homo sapiens

<400> SEQUENCE: 402

Ser Thr Asp Val Ser Asp Leu Leu His Gln Tyr
1               5                   10

<210> SEQ ID NO 403
<211> LENGTH: 9
<212> TYPE: PRT
<213> ORGANISM: Homo sapiens

<400> SEQUENCE: 403

Arg Ser Leu Pro Phe Phe Ser Ala Arg
1               5

<210> SEQ ID NO 404
<211> LENGTH: 9
<212> TYPE: PRT
<213> ORGANISM: Homo sapiens

<400> SEQUENCE: 404

Tyr Arg Phe Met Gly Thr Glu Ala Tyr
1               5

<210> SEQ ID NO 405
<211> LENGTH: 9
<212> TYPE: PRT
<213> ORGANISM: Homo sapiens

<400> SEQUENCE: 405

Met Pro Leu Leu Arg Gln Glu Glu Leu
1               5

```
<210> SEQ ID NO 406
<211> LENGTH: 9
<212> TYPE: PRT
<213> ORGANISM: Homo sapiens

<400> SEQUENCE: 406

Val Thr Glu Ile Asp Gln Asp Lys Tyr
1               5

<210> SEQ ID NO 407
<211> LENGTH: 9
<212> TYPE: PRT
<213> ORGANISM: Homo sapiens

<400> SEQUENCE: 407

Met Arg His Leu Gly Ala Phe Leu Phe
1               5

<210> SEQ ID NO 408
<211> LENGTH: 10
<212> TYPE: PRT
<213> ORGANISM: Homo sapiens

<400> SEQUENCE: 408

Thr Thr Glu Glu Ser Leu Arg Asn Tyr Tyr
1               5                   10

<210> SEQ ID NO 409
<211> LENGTH: 9
<212> TYPE: PRT
<213> ORGANISM: Homo sapiens

<400> SEQUENCE: 409

Met Arg Thr Ser Tyr Leu Leu Leu Phe
1               5

<210> SEQ ID NO 410
<211> LENGTH: 9
<212> TYPE: PRT
<213> ORGANISM: Homo sapiens

<400> SEQUENCE: 410

Thr Val Asp Gln Val Lys Asp Leu Tyr
1               5

<210> SEQ ID NO 411
<211> LENGTH: 9
<212> TYPE: PRT
<213> ORGANISM: Homo sapiens

<400> SEQUENCE: 411

Met Arg Tyr Val Ala Ser Tyr Leu Leu
1               5

<210> SEQ ID NO 412
<211> LENGTH: 9
<212> TYPE: PRT
<213> ORGANISM: Homo sapiens

<400> SEQUENCE: 412

Val Gly Leu Ile Arg Asn Leu Ala Leu
1               5

<210> SEQ ID NO 413
<211> LENGTH: 9
<212> TYPE: PRT
```

-continued

<213> ORGANISM: Homo sapiens

<400> SEQUENCE: 413

Gly Arg Leu Asp Ala Val Leu Gln Arg
1               5

<210> SEQ ID NO 414
<211> LENGTH: 10
<212> TYPE: PRT
<213> ORGANISM: Homo sapiens

<400> SEQUENCE: 414

Leu Leu Asp Gln Gly Gln Leu Asn Lys Tyr
1               5                   10

<210> SEQ ID NO 415
<211> LENGTH: 10
<212> TYPE: PRT
<213> ORGANISM: Homo sapiens

<400> SEQUENCE: 415

Asn Arg Phe Ala Gly Phe Gly Ile Gly Leu
1               5                   10

<210> SEQ ID NO 416
<211> LENGTH: 10
<212> TYPE: PRT
<213> ORGANISM: Homo sapiens

<400> SEQUENCE: 416

Lys Arg Leu Gly Thr Leu Val Val Thr Tyr
1               5                   10

<210> SEQ ID NO 417
<211> LENGTH: 9
<212> TYPE: PRT
<213> ORGANISM: Homo sapiens

<400> SEQUENCE: 417

Lys Arg Gly Asp Val Ile Tyr Ile Leu
1               5

<210> SEQ ID NO 418
<211> LENGTH: 9
<212> TYPE: PRT
<213> ORGANISM: Homo sapiens

<400> SEQUENCE: 418

Ser Arg Phe Asp Ile Pro Leu Gly Leu
1               5

<210> SEQ ID NO 419
<211> LENGTH: 10
<212> TYPE: PRT
<213> ORGANISM: Homo sapiens

<400> SEQUENCE: 419

Ser Thr Asp Pro Ser Val Leu Gly Lys Tyr
1               5                   10

<210> SEQ ID NO 420
<211> LENGTH: 9
<212> TYPE: PRT
<213> ORGANISM: Homo sapiens

<400> SEQUENCE: 420

Ser Arg Phe Leu Lys Ser Asp Leu Phe
1               5

<210> SEQ ID NO 421
<211> LENGTH: 9
<212> TYPE: PRT
<213> ORGANISM: Homo sapiens

<400> SEQUENCE: 421

Val Gln Lys Pro Ser Tyr Tyr Val Arg
1               5

<210> SEQ ID NO 422
<211> LENGTH: 10
<212> TYPE: PRT
<213> ORGANISM: Homo sapiens

<400> SEQUENCE: 422

Ser Arg Ile Ser Leu Pro Leu Pro Asn Phe
1               5                   10

<210> SEQ ID NO 423
<211> LENGTH: 9
<212> TYPE: PRT
<213> ORGANISM: Homo sapiens

<400> SEQUENCE: 423

Leu Arg Ser Gly Leu Pro Leu Leu Leu
1               5

<210> SEQ ID NO 424
<211> LENGTH: 9
<212> TYPE: PRT
<213> ORGANISM: Homo sapiens

<400> SEQUENCE: 424

Ser Phe Lys Asp Tyr Ile Gln Glu Arg
1               5

<210> SEQ ID NO 425
<211> LENGTH: 11
<212> TYPE: PRT
<213> ORGANISM: Homo sapiens

<400> SEQUENCE: 425

His Thr Gln Gly Pro Val Asp Gly Ser Leu Tyr
1               5                   10

<210> SEQ ID NO 426
<211> LENGTH: 10
<212> TYPE: PRT
<213> ORGANISM: Homo sapiens

<400> SEQUENCE: 426

Ser Thr Asp Lys Phe Lys Thr Asp Phe Tyr
1               5                   10

<210> SEQ ID NO 427
<211> LENGTH: 9
<212> TYPE: PRT
<213> ORGANISM: Homo sapiens

<400> SEQUENCE: 427

Gly Ser His Ser Met Arg Tyr Phe Phe
1               5

```
<210> SEQ ID NO 428
<211> LENGTH: 10
<212> TYPE: PRT
<213> ORGANISM: Homo sapiens

<400> SEQUENCE: 428

Gly Ser His Ser Met Arg Tyr Phe Phe Thr
1               5                   10

<210> SEQ ID NO 429
<211> LENGTH: 9
<212> TYPE: PRT
<213> ORGANISM: Homo sapiens

<400> SEQUENCE: 429

Gly Ser His Ser Met Arg Tyr Phe His
1               5

<210> SEQ ID NO 430
<211> LENGTH: 9
<212> TYPE: PRT
<213> ORGANISM: Homo sapiens

<400> SEQUENCE: 430

Ala Ala Ile Leu Gly Met His Asn Leu
1               5

<210> SEQ ID NO 431
<211> LENGTH: 9
<212> TYPE: PRT
<213> ORGANISM: Homo sapiens

<400> SEQUENCE: 431

Lys Leu Asp Pro Thr Lys Thr Thr Leu
1               5

<210> SEQ ID NO 432
<211> LENGTH: 9
<212> TYPE: PRT
<213> ORGANISM: Homo sapiens

<400> SEQUENCE: 432

Phe Val His Asp Leu Val Leu Tyr Leu
1               5

<210> SEQ ID NO 433
<211> LENGTH: 7
<212> TYPE: PRT
<213> ORGANISM: Homo sapiens

<400> SEQUENCE: 433

Phe Val His Asp Leu Val Leu
1               5

<210> SEQ ID NO 434
<211> LENGTH: 9
<212> TYPE: PRT
<213> ORGANISM: Homo sapiens

<400> SEQUENCE: 434

Val Leu Ile Pro Lys Leu Pro Gln Leu
1               5

<210> SEQ ID NO 435
```

```
<211> LENGTH: 9
<212> TYPE: PRT
<213> ORGANISM: Homo sapiens

<400> SEQUENCE: 435

Asn Glu Ile Thr Ile Pro Val Thr Phe
1               5

<210> SEQ ID NO 436
<211> LENGTH: 9
<212> TYPE: PRT
<213> ORGANISM: Homo sapiens

<400> SEQUENCE: 436

Tyr Leu Ala Asp Phe Leu Leu Thr Lys
1               5

<210> SEQ ID NO 437
<211> LENGTH: 9
<212> TYPE: PRT
<213> ORGANISM: Homo sapiens

<400> SEQUENCE: 437

Tyr Leu Ile Pro Leu Leu Glu Arg Leu
1               5

<210> SEQ ID NO 438
<211> LENGTH: 8
<212> TYPE: PRT
<213> ORGANISM: Homo sapiens

<400> SEQUENCE: 438

Asn Glu Val Val Thr Arg Glu Tyr
1               5

<210> SEQ ID NO 439
<211> LENGTH: 9
<212> TYPE: PRT
<213> ORGANISM: Homo sapiens

<400> SEQUENCE: 439

Asp Glu Phe Lys Ile Gly Glu Leu Phe
1               5

<210> SEQ ID NO 440
<211> LENGTH: 11
<212> TYPE: PRT
<213> ORGANISM: Homo sapiens

<400> SEQUENCE: 440

Ile Gln Arg Thr Pro Lys Ile Gln Val Tyr Ser
1               5                   10

<210> SEQ ID NO 441
<211> LENGTH: 9
<212> TYPE: PRT
<213> ORGANISM: Homo sapiens

<400> SEQUENCE: 441

Leu Thr Gly Pro Val Met Pro Val Arg
1               5

<210> SEQ ID NO 442
<211> LENGTH: 9
<212> TYPE: PRT
<213> ORGANISM: Homo sapiens
```

```
<400> SEQUENCE: 442

Ala Val Ala Ile Lys Ala Met Ala Lys
1               5

<210> SEQ ID NO 443
<211> LENGTH: 8
<212> TYPE: PRT
<213> ORGANISM: Homo sapiens

<400> SEQUENCE: 443

Phe Val Gln Met Met Thr Ala Lys
1               5

<210> SEQ ID NO 444
<211> LENGTH: 9
<212> TYPE: PRT
<213> ORGANISM: Homo sapiens

<400> SEQUENCE: 444

Ala Thr Asp Pro Asn Ile Leu Gly Arg
1               5

<210> SEQ ID NO 445
<211> LENGTH: 9
<212> TYPE: PRT
<213> ORGANISM: Homo sapiens

<400> SEQUENCE: 445

Leu Leu Leu Leu Ser Ile Val Ile Leu
1               5

<210> SEQ ID NO 446
<211> LENGTH: 10
<212> TYPE: PRT
<213> ORGANISM: Homo sapiens

<400> SEQUENCE: 446

Lys Leu Pro Asn Phe Gly Phe Val Val Phe
1               5                   10

<210> SEQ ID NO 447
<211> LENGTH: 9
<212> TYPE: PRT
<213> ORGANISM: Homo sapiens

<400> SEQUENCE: 447

Lys Leu Ser Glu Ile Asp Val Ala Leu
1               5

<210> SEQ ID NO 448
<211> LENGTH: 9
<212> TYPE: PRT
<213> ORGANISM: Homo sapiens

<400> SEQUENCE: 448

Leu Ala Ala Leu Pro His Ser Cys Leu
1               5

<210> SEQ ID NO 449
<211> LENGTH: 11
<212> TYPE: PRT
<213> ORGANISM: Homo sapiens

<400> SEQUENCE: 449
```

```
Tyr Ser Ile Ile Thr Pro Asn Ile Leu Arg Leu
1               5                   10

<210> SEQ ID NO 450
<211> LENGTH: 10
<212> TYPE: PRT
<213> ORGANISM: Homo sapiens

<400> SEQUENCE: 450

Ala Leu Pro Ser Arg Ile Leu Leu Trp Lys
1               5                   10

<210> SEQ ID NO 451
<211> LENGTH: 12
<212> TYPE: PRT
<213> ORGANISM: Homo sapiens

<400> SEQUENCE: 451

Val Lys Gly Phe Tyr Pro Ser Asp Ile Ala Val Glu
1               5                   10

<210> SEQ ID NO 452
<211> LENGTH: 9
<212> TYPE: PRT
<213> ORGANISM: Homo sapiens

<400> SEQUENCE: 452

Phe Leu Leu Asp Leu Ser Arg Ser Val
1               5

<210> SEQ ID NO 453
<211> LENGTH: 9
<212> TYPE: PRT
<213> ORGANISM: Homo sapiens

<400> SEQUENCE: 453

Ile Ile Tyr Lys Gly Gly Thr Ser Arg
1               5

<210> SEQ ID NO 454
<211> LENGTH: 9
<212> TYPE: PRT
<213> ORGANISM: Homo sapiens

<400> SEQUENCE: 454

Ile Val Ala Asp His Val Ala Ser Tyr
1               5

<210> SEQ ID NO 455
<211> LENGTH: 11
<212> TYPE: PRT
<213> ORGANISM: Homo sapiens

<400> SEQUENCE: 455

Glu Val Gly Gly Glu Ala Leu Gly Arg Leu Leu
1               5                   10

<210> SEQ ID NO 456
<211> LENGTH: 10
<212> TYPE: PRT
<213> ORGANISM: Homo sapiens

<400> SEQUENCE: 456

Arg Thr Gly Pro Pro Met Gly Ser Arg Phe
1               5                   10
```

```
<210> SEQ ID NO 457
<211> LENGTH: 9
<212> TYPE: PRT
<213> ORGANISM: Homo sapiens

<400> SEQUENCE: 457

Arg Gln Ile Gln Glu Ser Val Thr Phe
1               5

<210> SEQ ID NO 458
<211> LENGTH: 9
<212> TYPE: PRT
<213> ORGANISM: Homo sapiens

<400> SEQUENCE: 458

Arg Val Ala Pro Glu Glu His Pro Val
1               5

<210> SEQ ID NO 459
<211> LENGTH: 9
<212> TYPE: PRT
<213> ORGANISM: Homo sapiens

<400> SEQUENCE: 459

Thr Leu Ala Asp Leu Leu Ala Leu Arg
1               5

<210> SEQ ID NO 460
<211> LENGTH: 12
<212> TYPE: PRT
<213> ORGANISM: Homo sapiens

<400> SEQUENCE: 460

Arg Val Ala Pro Glu Glu His Pro Val Leu Leu Thr
1               5                   10

<210> SEQ ID NO 461
<211> LENGTH: 9
<212> TYPE: PRT
<213> ORGANISM: Homo sapiens

<400> SEQUENCE: 461

Thr Leu Ala Asp Ile Ile Ala Arg Leu
1               5

<210> SEQ ID NO 462
<211> LENGTH: 10
<212> TYPE: PRT
<213> ORGANISM: Homo sapiens

<400> SEQUENCE: 462

Arg Trp Glu Asp Gly Ser Pro Leu Asn Phe
1               5                   10

<210> SEQ ID NO 463
<211> LENGTH: 8
<212> TYPE: PRT
<213> ORGANISM: Homo sapiens

<400> SEQUENCE: 463

Tyr Glu Val Ser Gln Leu Lys Asp
1               5

<210> SEQ ID NO 464
<211> LENGTH: 10
```

```
<212> TYPE: PRT
<213> ORGANISM: Homo sapiens

<400> SEQUENCE: 464

Tyr Arg Asp Ile Pro Glu Leu Gln Gly Phe
1               5                   10

<210> SEQ ID NO 465
<211> LENGTH: 10
<212> TYPE: PRT
<213> ORGANISM: Homo sapiens

<400> SEQUENCE: 465

Tyr Val Asp Gly Thr Gln Phe Val Arg Phe
1               5                   10

<210> SEQ ID NO 466
<211> LENGTH: 9
<212> TYPE: PRT
<213> ORGANISM: Homo sapiens

<400> SEQUENCE: 466

Ser Leu Leu Asp Glu Phe Tyr Lys Leu
1               5

<210> SEQ ID NO 467
<211> LENGTH: 9
<212> TYPE: PRT
<213> ORGANISM: Homo sapiens

<400> SEQUENCE: 467

His Gly Ile Asp Pro Thr Gly Thr Tyr
1               5

<210> SEQ ID NO 468
<211> LENGTH: 13
<212> TYPE: PRT
<213> ORGANISM: Homo sapiens

<400> SEQUENCE: 468

Ser Leu Asp Lys Phe Leu Ala Ser Val Ser Thr Val Leu
1               5                   10

<210> SEQ ID NO 469
<211> LENGTH: 10
<212> TYPE: PRT
<213> ORGANISM: Homo sapiens

<400> SEQUENCE: 469

Ser Ile Gly Glu Arg Asp Leu Ile Phe His
1               5                   10

<210> SEQ ID NO 470
<211> LENGTH: 9
<212> TYPE: PRT
<213> ORGANISM: Homo sapiens

<400> SEQUENCE: 470

Ser Ile Thr Ser Val Phe Ile Thr Lys
1               5

<210> SEQ ID NO 471
<211> LENGTH: 11
<212> TYPE: PRT
<213> ORGANISM: Homo sapiens
```

```
<400> SEQUENCE: 471

Phe Gly Glu His Leu Leu Glu Ser Asp Leu Phe
1               5                   10

<210> SEQ ID NO 472
<211> LENGTH: 9
<212> TYPE: PRT
<213> ORGANISM: Homo sapiens

<400> SEQUENCE: 472

Phe Leu Asp Pro Ile Lys Ala Tyr Leu
1               5

<210> SEQ ID NO 473
<211> LENGTH: 11
<212> TYPE: PRT
<213> ORGANISM: Homo sapiens

<400> SEQUENCE: 473

Phe Leu Ala Asp Pro Ser Ala Phe Val Ala Ala
1               5                   10

<210> SEQ ID NO 474
<211> LENGTH: 9
<212> TYPE: PRT
<213> ORGANISM: Homo sapiens

<400> SEQUENCE: 474

Ile Thr Ala Pro Pro Ser Arg Val Leu
1               5

<210> SEQ ID NO 475
<211> LENGTH: 10
<212> TYPE: PRT
<213> ORGANISM: Homo sapiens

<400> SEQUENCE: 475

Val Leu Asp Glu Leu Lys Asn Met Lys Cys
1               5                   10

<210> SEQ ID NO 476
<211> LENGTH: 9
<212> TYPE: PRT
<213> ORGANISM: Homo sapiens

<400> SEQUENCE: 476

Leu Leu Gly Pro Arg Leu Val Leu Ala
1               5

<210> SEQ ID NO 477
<211> LENGTH: 9
<212> TYPE: PRT
<213> ORGANISM: Homo sapiens

<400> SEQUENCE: 477

Ile Ile Met Pro His Asn Ile Tyr Leu
1               5

<210> SEQ ID NO 478
<211> LENGTH: 8
<212> TYPE: PRT
<213> ORGANISM: Homo sapiens

<400> SEQUENCE: 478

Leu Val Arg Met Val Leu Asn Gly
```

<210> SEQ ID NO 479
<211> LENGTH: 10
<212> TYPE: PRT
<213> ORGANISM: Homo sapiens

<400> SEQUENCE: 479

Arg Leu Tyr Gly Pro Ser Ser Val Ser Phe
1               5                   10

<210> SEQ ID NO 480
<211> LENGTH: 9
<212> TYPE: PRT
<213> ORGANISM: Homo sapiens

<400> SEQUENCE: 480

Phe Glu Ala Pro Ile Lys Leu Val Phe
1               5

<210> SEQ ID NO 481
<211> LENGTH: 9
<212> TYPE: PRT
<213> ORGANISM: Homo sapiens

<400> SEQUENCE: 481

Ile Gln Pro Gly Ala Val Lys Val Tyr
1               5

<210> SEQ ID NO 482
<211> LENGTH: 9
<212> TYPE: PRT
<213> ORGANISM: Homo sapiens

<400> SEQUENCE: 482

Val Leu Ala Glu Val Pro Thr Gln Leu
1               5

<210> SEQ ID NO 483
<211> LENGTH: 9
<212> TYPE: PRT
<213> ORGANISM: Homo sapiens

<400> SEQUENCE: 483

Ile Met Arg Ala Gly Met Ser Ser Leu
1               5

<210> SEQ ID NO 484
<211> LENGTH: 12
<212> TYPE: PRT
<213> ORGANISM: Homo sapiens

<400> SEQUENCE: 484

Val Glu Phe Ser Ser Gly Leu Lys Gly Met Ser Leu
1               5                   10

<210> SEQ ID NO 485
<211> LENGTH: 11
<212> TYPE: PRT
<213> ORGANISM: Homo sapiens

<400> SEQUENCE: 485

Ile Leu Asn Pro Asp Asn Ser Phe Glu Ile Leu
1               5                   10

```
<210> SEQ ID NO 486
<211> LENGTH: 9
<212> TYPE: PRT
<213> ORGANISM: Homo sapiens

<400> SEQUENCE: 486

Val Ala Leu Glu Phe Ala Leu His Leu
1               5

<210> SEQ ID NO 487
<211> LENGTH: 9
<212> TYPE: PRT
<213> ORGANISM: Homo sapiens

<400> SEQUENCE: 487

Thr Val Ala Val Pro Leu Val Gly Lys
1               5

<210> SEQ ID NO 488
<211> LENGTH: 9
<212> TYPE: PRT
<213> ORGANISM: Homo sapiens

<400> SEQUENCE: 488

Thr Leu Ser Asp Leu Arg Val Tyr Leu
1               5

<210> SEQ ID NO 489
<211> LENGTH: 9
<212> TYPE: PRT
<213> ORGANISM: Homo sapiens

<400> SEQUENCE: 489

Thr Leu Ile Asp Ile Met Thr Arg Phe
1               5

<210> SEQ ID NO 490
<211> LENGTH: 9
<212> TYPE: PRT
<213> ORGANISM: Homo sapiens

<400> SEQUENCE: 490

His Asp Phe Pro Arg Ala Leu Ile Phe
1               5

<210> SEQ ID NO 491
<211> LENGTH: 8
<212> TYPE: PRT
<213> ORGANISM: Homo sapiens

<400> SEQUENCE: 491

Gly Ser His Ser Met Arg Tyr Phe
1               5

<210> SEQ ID NO 492
<211> LENGTH: 10
<212> TYPE: PRT
<213> ORGANISM: Homo sapiens

<400> SEQUENCE: 492

Ser Leu Met Asp His Thr Ile Pro Glu Val
1               5                   10

<210> SEQ ID NO 493
<211> LENGTH: 11
<212> TYPE: PRT
```

```
<213> ORGANISM: Homo sapiens

<400> SEQUENCE: 493

Ser Gly Val His Thr Phe Pro Ala Val Leu Gln
1               5                   10

<210> SEQ ID NO 494
<211> LENGTH: 9
<212> TYPE: PRT
<213> ORGANISM: Homo sapiens

<400> SEQUENCE: 494

Phe Leu Val Thr Val Ile His Thr Leu
1               5

<210> SEQ ID NO 495
<211> LENGTH: 8
<212> TYPE: PRT
<213> ORGANISM: Homo sapiens

<400> SEQUENCE: 495

Thr Asp Gly Lys Val Phe Gln Phe
1               5

<210> SEQ ID NO 496
<211> LENGTH: 9
<212> TYPE: PRT
<213> ORGANISM: Homo sapiens

<400> SEQUENCE: 496

Tyr Asp Leu Leu Arg Asn Thr Asn Phe
1               5

<210> SEQ ID NO 497
<211> LENGTH: 9
<212> TYPE: PRT
<213> ORGANISM: Homo sapiens

<400> SEQUENCE: 497

Ile Leu Tyr Pro Lys Thr Leu Phe Leu
1               5

<210> SEQ ID NO 498
<211> LENGTH: 8
<212> TYPE: PRT
<213> ORGANISM: Homo sapiens

<400> SEQUENCE: 498

Met Arg Tyr Val Ala Ser Tyr Leu
1               5

<210> SEQ ID NO 499
<211> LENGTH: 9
<212> TYPE: PRT
<213> ORGANISM: Homo sapiens

<400> SEQUENCE: 499

Phe Ile Trp Glu Asn Ile His Thr Leu
1               5

<210> SEQ ID NO 500
<211> LENGTH: 9
<212> TYPE: PRT
<213> ORGANISM: Homo sapiens

<400> SEQUENCE: 500
```

Arg Glu Leu Pro Ala Trp Val Ser Phe
1               5

<210> SEQ ID NO 501
<211> LENGTH: 9
<212> TYPE: PRT
<213> ORGANISM: Homo sapiens

<400> SEQUENCE: 501

Gln Asp Leu Asn Arg Ile Phe Pro Leu
1               5

<210> SEQ ID NO 502
<211> LENGTH: 8
<212> TYPE: PRT
<213> ORGANISM: Homo sapiens

<400> SEQUENCE: 502

Arg Asp Ser Ile Val Ala Glu Leu
1               5

<210> SEQ ID NO 503
<211> LENGTH: 9
<212> TYPE: PRT
<213> ORGANISM: Homo sapiens

<400> SEQUENCE: 503

Ala Asp Val Leu Lys Val Glu Val Phe
1               5

<210> SEQ ID NO 504
<211> LENGTH: 8
<212> TYPE: PRT
<213> ORGANISM: Homo sapiens

<400> SEQUENCE: 504

Tyr Asp Ser Ile Ile Tyr Arg Met
1               5

<210> SEQ ID NO 505
<211> LENGTH: 9
<212> TYPE: PRT
<213> ORGANISM: Homo sapiens

<400> SEQUENCE: 505

Ala Met Asn Pro Val Glu His Pro Phe
1               5

<210> SEQ ID NO 506
<211> LENGTH: 9
<212> TYPE: PRT
<213> ORGANISM: Homo sapiens

<400> SEQUENCE: 506

Ser Glu Leu Ile Arg Asn Val Thr Leu
1               5

<210> SEQ ID NO 507
<211> LENGTH: 9
<212> TYPE: PRT
<213> ORGANISM: Homo sapiens

<400> SEQUENCE: 507

Gln Asp Val Ala Arg Val Leu Gly Phe
1               5

<210> SEQ ID NO 508
<211> LENGTH: 9
<212> TYPE: PRT
<213> ORGANISM: Homo sapiens

<400> SEQUENCE: 508

Ser Asp His Ile His Ile Ile Ala Leu
1               5

<210> SEQ ID NO 509
<211> LENGTH: 9
<212> TYPE: PRT
<213> ORGANISM: Homo sapiens

<400> SEQUENCE: 509

Ala Asp Ser Leu Arg Leu Gln Gln Leu
1               5

<210> SEQ ID NO 510
<211> LENGTH: 8
<212> TYPE: PRT
<213> ORGANISM: Homo sapiens

<400> SEQUENCE: 510

Leu Leu Asp Ile Arg Ser Glu Tyr
1               5

<210> SEQ ID NO 511
<211> LENGTH: 9
<212> TYPE: PRT
<213> ORGANISM: Homo sapiens

<400> SEQUENCE: 511

Val Leu Phe Gly Leu Leu Arg Glu Val
1               5

<210> SEQ ID NO 512
<211> LENGTH: 9
<212> TYPE: PRT
<213> ORGANISM: Homo sapiens

<400> SEQUENCE: 512

Val Ala Val Gly Arg Ala Leu Tyr Tyr
1               5

<210> SEQ ID NO 513
<211> LENGTH: 9
<212> TYPE: PRT
<213> ORGANISM: Homo sapiens

<400> SEQUENCE: 513

Met Arg Phe Leu Ala Ala Thr Phe Leu
1               5

<210> SEQ ID NO 514
<211> LENGTH: 9
<212> TYPE: PRT
<213> ORGANISM: Homo sapiens

<400> SEQUENCE: 514

Tyr Thr Asp Pro Glu Val Phe Lys Tyr
1               5

<210> SEQ ID NO 515

```
<211> LENGTH: 9
<212> TYPE: PRT
<213> ORGANISM: Homo sapiens

<400> SEQUENCE: 515

His Asp Phe Leu Lys Tyr Asp Phe Phe
1               5

<210> SEQ ID NO 516
<211> LENGTH: 9
<212> TYPE: PRT
<213> ORGANISM: Homo sapiens

<400> SEQUENCE: 516

Ala Ile Asp Gln Leu His Leu Glu Tyr
1               5

<210> SEQ ID NO 517
<211> LENGTH: 9
<212> TYPE: PRT
<213> ORGANISM: Homo sapiens

<400> SEQUENCE: 517

Ser Asp Leu Glu Arg Val Thr Ser Leu
1               5

<210> SEQ ID NO 518
<211> LENGTH: 9
<212> TYPE: PRT
<213> ORGANISM: Homo sapiens

<400> SEQUENCE: 518

Thr Leu Leu Pro Leu Arg Val Phe Leu
1               5

<210> SEQ ID NO 519
<211> LENGTH: 10
<212> TYPE: PRT
<213> ORGANISM: Homo sapiens

<400> SEQUENCE: 519

Tyr Ser Ile Ile Thr Pro Asn Ile Leu Arg
1               5                   10

<210> SEQ ID NO 520
<211> LENGTH: 9
<212> TYPE: PRT
<213> ORGANISM: Homo sapiens

<400> SEQUENCE: 520

Phe Glu Leu Gln Arg Asn Phe Gln Leu
1               5

<210> SEQ ID NO 521
<211> LENGTH: 9
<212> TYPE: PRT
<213> ORGANISM: Homo sapiens

<400> SEQUENCE: 521

Leu Asp Leu Gln Arg Asn Tyr Ile Phe
1               5

<210> SEQ ID NO 522
<211> LENGTH: 9
<212> TYPE: PRT
<213> ORGANISM: Homo sapiens
```

```
<400> SEQUENCE: 522

Arg Arg Leu Asp Pro Ile Pro Gln Leu
1               5

<210> SEQ ID NO 523
<211> LENGTH: 12
<212> TYPE: PRT
<213> ORGANISM: Homo sapiens

<400> SEQUENCE: 523

Ser Leu Pro Ile Lys Glu Ser Glu Ile Ile Asp Phe
1               5                   10

<210> SEQ ID NO 524
<211> LENGTH: 9
<212> TYPE: PRT
<213> ORGANISM: Homo sapiens

<400> SEQUENCE: 524

Thr Glu Leu Leu Arg Tyr Tyr Met Leu
1               5

<210> SEQ ID NO 525
<211> LENGTH: 10
<212> TYPE: PRT
<213> ORGANISM: Homo sapiens

<400> SEQUENCE: 525

Phe Ile Tyr His Gly Glu Val Pro Gln Ala
1               5                   10

<210> SEQ ID NO 526
<211> LENGTH: 9
<212> TYPE: PRT
<213> ORGANISM: Homo sapiens

<400> SEQUENCE: 526

Ala Glu Met Leu Arg Ser Ile Ser Phe
1               5

<210> SEQ ID NO 527
<211> LENGTH: 10
<212> TYPE: PRT
<213> ORGANISM: Homo sapiens

<400> SEQUENCE: 527

Arg Leu Gln Glu Asp Pro Pro Val Gly Val
1               5                   10

<210> SEQ ID NO 528
<211> LENGTH: 9
<212> TYPE: PRT
<213> ORGANISM: Homo sapiens

<400> SEQUENCE: 528

Ala Glu Leu Glu Arg Ala Ala Ala Leu
1               5

<210> SEQ ID NO 529
<211> LENGTH: 8
<212> TYPE: PRT
<213> ORGANISM: Homo sapiens

<400> SEQUENCE: 529
```

Tyr Thr Asp Lys Ile Asp Arg Tyr
1               5

<210> SEQ ID NO 530
<211> LENGTH: 9
<212> TYPE: PRT
<213> ORGANISM: Homo sapiens

<400> SEQUENCE: 530

Phe Leu Leu Pro Asp Val Ile Arg Ile
1               5

<210> SEQ ID NO 531
<211> LENGTH: 9
<212> TYPE: PRT
<213> ORGANISM: Homo sapiens

<400> SEQUENCE: 531

Val Glu Leu Pro His Ile Asn Leu Leu
1               5

<210> SEQ ID NO 532
<211> LENGTH: 9
<212> TYPE: PRT
<213> ORGANISM: Homo sapiens

<400> SEQUENCE: 532

Val Met Leu Asp Val Pro Ile Arg Leu
1               5

<210> SEQ ID NO 533
<211> LENGTH: 9
<212> TYPE: PRT
<213> ORGANISM: Homo sapiens

<400> SEQUENCE: 533

Ser Leu Leu Glu Asn Leu Glu Lys Ile
1               5

<210> SEQ ID NO 534
<211> LENGTH: 9
<212> TYPE: PRT
<213> ORGANISM: Homo sapiens

<400> SEQUENCE: 534

Tyr Ala Asp Pro Val Asn Ala His Tyr
1               5

<210> SEQ ID NO 535
<211> LENGTH: 9
<212> TYPE: PRT
<213> ORGANISM: Homo sapiens

<400> SEQUENCE: 535

Ala Glu Leu Leu Arg Gly Leu Ser Leu
1               5

<210> SEQ ID NO 536
<211> LENGTH: 9
<212> TYPE: PRT
<213> ORGANISM: Homo sapiens

<400> SEQUENCE: 536

Thr Thr Glu Val His Pro Glu Leu Tyr
1               5

```
<210> SEQ ID NO 537
<211> LENGTH: 9
<212> TYPE: PRT
<213> ORGANISM: Homo sapiens

<400> SEQUENCE: 537

Arg Glu Thr Asn Leu Asp Ser Leu Pro
1               5

<210> SEQ ID NO 538
<211> LENGTH: 9
<212> TYPE: PRT
<213> ORGANISM: Homo sapiens

<400> SEQUENCE: 538

Glu Leu Glu Asp Ser Thr Leu Arg Tyr
1               5

<210> SEQ ID NO 539
<211> LENGTH: 8
<212> TYPE: PRT
<213> ORGANISM: Homo sapiens

<400> SEQUENCE: 539

Phe Leu Asp Ile Tyr Ile Phe Leu
1               5

<210> SEQ ID NO 540
<211> LENGTH: 9
<212> TYPE: PRT
<213> ORGANISM: Homo sapiens

<400> SEQUENCE: 540

Thr Tyr Thr Asp Arg Val Phe Phe Leu
1               5

<210> SEQ ID NO 541
<211> LENGTH: 10
<212> TYPE: PRT
<213> ORGANISM: Homo sapiens

<400> SEQUENCE: 541

Ser Pro His Leu Ala Asn Tyr Phe Tyr Phe
1               5                   10

<210> SEQ ID NO 542
<211> LENGTH: 9
<212> TYPE: PRT
<213> ORGANISM: Homo sapiens

<400> SEQUENCE: 542

Ser Pro Arg Leu Pro Val Gly Gly Phe
1               5

<210> SEQ ID NO 543
<211> LENGTH: 10
<212> TYPE: PRT
<213> ORGANISM: Homo sapiens

<400> SEQUENCE: 543

Lys Leu Leu Asp Lys Val Gln Ala Tyr Ser
1               5                   10

<210> SEQ ID NO 544
<211> LENGTH: 9
```

```
<212> TYPE: PRT
<213> ORGANISM: Homo sapiens

<400> SEQUENCE: 544

Ala Tyr Gln His Leu Phe Tyr Leu Leu
1               5

<210> SEQ ID NO 545
<211> LENGTH: 10
<212> TYPE: PRT
<213> ORGANISM: Homo sapiens

<400> SEQUENCE: 545

Lys Tyr Ile Leu Leu Met Asp Ile Ile Ala
1               5                   10

<210> SEQ ID NO 546
<211> LENGTH: 9
<212> TYPE: PRT
<213> ORGANISM: Homo sapiens

<400> SEQUENCE: 546

Arg Tyr Ser Ser Met Ala Ala Ser Phe
1               5

<210> SEQ ID NO 547
<211> LENGTH: 10
<212> TYPE: PRT
<213> ORGANISM: Homo sapiens

<400> SEQUENCE: 547

Ser Pro Arg Ala Ala Glu Pro Val Gln Leu
1               5                   10

<210> SEQ ID NO 548
<211> LENGTH: 9
<212> TYPE: PRT
<213> ORGANISM: Homo sapiens

<400> SEQUENCE: 548

Ile Tyr Thr Ser Ser Val Asn Arg Leu
1               5

<210> SEQ ID NO 549
<211> LENGTH: 9
<212> TYPE: PRT
<213> ORGANISM: Homo sapiens

<400> SEQUENCE: 549

Leu Tyr Pro Gln Phe Met Phe His Leu
1               5

<210> SEQ ID NO 550
<211> LENGTH: 9
<212> TYPE: PRT
<213> ORGANISM: Homo sapiens

<400> SEQUENCE: 550

Arg Tyr Ile Pro Thr Ala Ala Ala Phe
1               5

<210> SEQ ID NO 551
<211> LENGTH: 9
<212> TYPE: PRT
<213> ORGANISM: Homo sapiens
```

```
<400> SEQUENCE: 551

Glu Tyr Ile Val Lys Lys Ile Pro Val
1               5

<210> SEQ ID NO 552
<211> LENGTH: 9
<212> TYPE: PRT
<213> ORGANISM: Homo sapiens

<400> SEQUENCE: 552

Ser Arg Val Glu Ala Val Tyr Val Leu
1               5

<210> SEQ ID NO 553
<211> LENGTH: 9
<212> TYPE: PRT
<213> ORGANISM: Homo sapiens

<400> SEQUENCE: 553

Met Pro Arg Gly Val Val Val Thr Leu
1               5

<210> SEQ ID NO 554
<211> LENGTH: 9
<212> TYPE: PRT
<213> ORGANISM: Homo sapiens

<400> SEQUENCE: 554

Leu Pro Lys Pro Pro Gly Arg Gly Val
1               5

<210> SEQ ID NO 555
<211> LENGTH: 9
<212> TYPE: PRT
<213> ORGANISM: Homo sapiens

<400> SEQUENCE: 555

Arg Leu Trp Gly Glu Pro Val Asn Leu
1               5

<210> SEQ ID NO 556
<211> LENGTH: 9
<212> TYPE: PRT
<213> ORGANISM: Homo sapiens

<400> SEQUENCE: 556

Arg Leu Leu Asp Val Leu Ala Pro Leu
1               5

<210> SEQ ID NO 557
<211> LENGTH: 9
<212> TYPE: PRT
<213> ORGANISM: Homo sapiens

<400> SEQUENCE: 557

Leu Tyr Ile Leu Ser Ser His Asp Ile
1               5

<210> SEQ ID NO 558
<211> LENGTH: 9
<212> TYPE: PRT
<213> ORGANISM: Homo sapiens

<400> SEQUENCE: 558

Thr Pro Met Gly Pro Gly Arg Thr Val
```

-continued

<210> SEQ ID NO 559
<211> LENGTH: 14
<212> TYPE: PRT
<213> ORGANISM: Homo sapiens

<400> SEQUENCE: 559

Gly Pro Pro Gly Thr Gly Lys Thr Asp Val Ala Val Gln Ile
1               5                   10

<210> SEQ ID NO 560
<211> LENGTH: 10
<212> TYPE: PRT
<213> ORGANISM: Homo sapiens

<400> SEQUENCE: 560

Asn Glu Ile Glu Asp Thr Phe Arg Gln Phe
1               5                   10

<210> SEQ ID NO 561
<211> LENGTH: 10
<212> TYPE: PRT
<213> ORGANISM: Homo sapiens

<400> SEQUENCE: 561

Glu Glu Ile Asp Leu Arg Ser Val Gly Trp
1               5                   10

<210> SEQ ID NO 562
<211> LENGTH: 9
<212> TYPE: PRT
<213> ORGANISM: Homo sapiens

<400> SEQUENCE: 562

Lys Tyr Gln Lys Gly Phe Ser Leu Trp
1               5

<210> SEQ ID NO 563
<211> LENGTH: 9
<212> TYPE: PRT
<213> ORGANISM: Homo sapiens

<400> SEQUENCE: 563

Val Tyr Pro Asp Gly Ile Arg His Ile
1               5

<210> SEQ ID NO 564
<211> LENGTH: 9
<212> TYPE: PRT
<213> ORGANISM: Homo sapiens

<400> SEQUENCE: 564

Lys Phe Ile Asp Thr Thr Ser Lys Phe
1               5

<210> SEQ ID NO 565
<211> LENGTH: 9
<212> TYPE: PRT
<213> ORGANISM: Homo sapiens

<400> SEQUENCE: 565

Phe Leu Asp Ile Leu Asn Thr Leu Ile
1               5

<210> SEQ ID NO 566
<211> LENGTH: 11
<212> TYPE: PRT
<213> ORGANISM: Homo sapiens

<400> SEQUENCE: 566

Lys Tyr Ile Thr Gln Gly Gln Leu Leu Gln Phe
1               5                   10

<210> SEQ ID NO 567
<211> LENGTH: 10
<212> TYPE: PRT
<213> ORGANISM: Homo sapiens

<400> SEQUENCE: 567

Lys Tyr Leu Ser Val Gln Gly Gln Leu Phe
1               5                   10

<210> SEQ ID NO 568
<211> LENGTH: 9
<212> TYPE: PRT
<213> ORGANISM: Homo sapiens

<400> SEQUENCE: 568

Arg Tyr Phe Asp Glu Pro Val Glu Leu
1               5

<210> SEQ ID NO 569
<211> LENGTH: 9
<212> TYPE: PRT
<213> ORGANISM: Homo sapiens

<400> SEQUENCE: 569

Lys Tyr Asp Glu Ile Phe Tyr Asn Leu
1               5

<210> SEQ ID NO 570
<211> LENGTH: 9
<212> TYPE: PRT
<213> ORGANISM: Homo sapiens

<400> SEQUENCE: 570

Ser Tyr Ile Glu His Ile Phe Glu Ile
1               5

<210> SEQ ID NO 571
<211> LENGTH: 10
<212> TYPE: PRT
<213> ORGANISM: Homo sapiens

<400> SEQUENCE: 571

Lys Phe Ile Asp Pro Ile Tyr Gln Val Trp
1               5                   10

<210> SEQ ID NO 572
<211> LENGTH: 11
<212> TYPE: PRT
<213> ORGANISM: Homo sapiens

<400> SEQUENCE: 572

Leu Gly Tyr Thr Glu Gly Ala Leu Leu Ala Leu
1               5                   10

<210> SEQ ID NO 573
<211> LENGTH: 9
<212> TYPE: PRT

```
<213> ORGANISM: Homo sapiens

<400> SEQUENCE: 573

Lys Tyr Pro Ser Pro Phe Phe Val Phe
1               5

<210> SEQ ID NO 574
<211> LENGTH: 10
<212> TYPE: PRT
<213> ORGANISM: Homo sapiens

<400> SEQUENCE: 574

Glu Tyr Pro Asp Arg Ile Met Asn Thr Phe
1               5                   10

<210> SEQ ID NO 575
<211> LENGTH: 9
<212> TYPE: PRT
<213> ORGANISM: Homo sapiens

<400> SEQUENCE: 575

Val Tyr Ile Ser Glu His Glu His Phe
1               5

<210> SEQ ID NO 576
<211> LENGTH: 9
<212> TYPE: PRT
<213> ORGANISM: Homo sapiens

<400> SEQUENCE: 576

Lys Tyr Phe Leu Lys Pro Glu Val Leu
1               5

<210> SEQ ID NO 577
<211> LENGTH: 9
<212> TYPE: PRT
<213> ORGANISM: Homo sapiens

<400> SEQUENCE: 577

Gly Pro Ala Leu Gly Arg Ser Phe Leu
1               5

<210> SEQ ID NO 578
<211> LENGTH: 10
<212> TYPE: PRT
<213> ORGANISM: Artificial
<220> FEATURE:
<223> OTHER INFORMATION: Description of Artificial Sequence: Synthetic
      peptide

<400> SEQUENCE: 578

Glu Leu Ala Gly Ile Gly Ile Leu Thr Val
1               5                   10

<210> SEQ ID NO 579
<211> LENGTH: 9
<212> TYPE: PRT
<213> ORGANISM: Human immunodeficiency virus type 1

<400> SEQUENCE: 579

Ile Leu Lys Glu Pro Val His Gly Val
1               5

<210> SEQ ID NO 580
<211> LENGTH: 9
<212> TYPE: PRT
```

-continued

```
<213> ORGANISM: Influenza virus

<400> SEQUENCE: 580

Gly Ile Leu Gly Phe Val Phe Thr Leu
1               5

<210> SEQ ID NO 581
<211> LENGTH: 9
<212> TYPE: PRT
<213> ORGANISM: Human cytomegalovirus

<400> SEQUENCE: 581

Asn Leu Val Pro Met Val Ala Thr Val
1               5

<210> SEQ ID NO 582
<211> LENGTH: 10
<212> TYPE: PRT
<213> ORGANISM: Human herpesvirus 4

<400> SEQUENCE: 582

Leu Leu Asp Phe Val Arg Phe Met Gly Val
1               5                   10

<210> SEQ ID NO 583
<211> LENGTH: 9
<212> TYPE: PRT
<213> ORGANISM: Human herpesvirus 4

<400> SEQUENCE: 583

Gly Leu Cys Thr Leu Val Ala Met Leu
1               5

<210> SEQ ID NO 584
<211> LENGTH: 9
<212> TYPE: PRT
<213> ORGANISM: Human herpesvirus 4

<400> SEQUENCE: 584

Cys Leu Gly Gly Leu Leu Thr Met Val
1               5
```